United States Patent
Kunimatsu et al.

[19]

[11] Patent Number: 6,106,692
[45] Date of Patent: Aug. 22, 2000

[54] MEASURING CONCENTRATIONS OF PLURAL TARGET SUBSTANCES BY USE OF DIAMOND ELECTRODE

[75] Inventors: Keiji Kunimatsu; Toshihide Nakata; Toshiya Saito; Mayumi Kazuta, all of Hokkaido; Akira Fujishima, 710-5, Nakamaruko,Nakahara-ku, Kawasaki-shi, Kanagawa-ken; Kazuhito Hashimoto, 2073-2-D213, Iijima-cho,Sakae-ku, Yokohama-shi,Kanagawa-ken; Kohei Uosaki, Atsubetsu Higashi,1-5-3-27, Atsubetsu-ku, Sapporo-shi,Hokkaido, all of Japan

[73] Assignees: Imra Japan Kabushikikaisha; Akira Fujishima; Kazuhito Hashimoto; Kohei Uosaki, all of, Japan

[21] Appl. No.: 09/114,176

[22] Filed: Jul. 13, 1998

[30] Foreign Application Priority Data

Jul. 14, 1997 [JP] Japan ................................... 9-203811
Apr. 22, 1998 [JP] Japan ................................... 10-111811

[51] Int. Cl.⁷ ........................................................ G01N 27/26
[52] U.S. Cl. ..................... 205/775; 204/294; 204/400; 204/412; 205/782; 205/786; 205/787; 205/792; 205/794.5

[58] Field of Search .................................... 204/400, 403, 204/412, 431, 294; 205/775, 782, 787, 792, 794.5, 786

[56] References Cited

U.S. PATENT DOCUMENTS

| | | |
|---|---|---|
| 3,902,970 | 9/1975 | Levin . |
| 5,399,247 | 3/1995 | Carey et al. ............................ 204/294 |
| 5,777,372 | 7/1998 | Kobashi .................................. 257/414 |

*Primary Examiner*—T. Tung
*Attorney, Agent, or Firm*—Lorusso & Loud

[57] ABSTRACT

There is provided a concentration sensor for measurement of concentrations of one or plural target substances in a system, with a detection electrode of conductive diamond. The measuring method with the concentration sensor involves measuring the reaction potentials of plural target substances in a sample containing and determining the concentrations of the plural substances by use of the difference between the resulting reaction potentials of the respective substances. The measuring method can also determine the concentration of a single substance in a sample containing one kind of target substance.

11 Claims, 44 Drawing Sheets

POTENTIAL AT DETECTION ELECTRODE

CONCENTRATION OF TARGET SUBSTANCE A

POTENTIAL AT DETECTION ELECTRODE

CONCENTRATION OF TARGET SUBSTANCE B

CONCENTRATION OF TARGET SUBSTANCE B

POTENTIAL AT Pt DETECTION ELECTRODE

CONCENTRATION OF TARGET SUBSTANCE B

CONCENTRATION OF TARGET SUBSTANCE A

CONCENTRATION OF TARGET SUBSTANCE B

MEASURING CONCENTRATIONS OF PLURAL TARGET SUBSTANCES BY USE OF DIAMOND ELECTRODE

BACKGROUND OF THE INVENTION

1. Field of the Invention

The present invention relates to measurement of plural target substances by use of a diamond electrode, and more particularly to a method of measuring concentrations of plural target substances in a sample from a change in a response electric current obtained by changing a potential in the interface of a diamond electrode. The present invention also relates to a concentration sensor to be used for that purpose.

2. Prior Art

Concentration sensors that electrochemically measure concentrations of various substances such as ions, inorganic compounds, organic compounds, polymeric compounds, living body-related substances etc. have been known. Such concentration sensors use an electrode for detecting changes in electric currents or potentials occurring in the interface of the electrode. Carbon-based materials, metal oxides, metals, semiconductors etc. are used as electrode materials in the electrodes in such concentration sensors. Sensor performance depends on the characteristics of the electrode materials used therein.

One of the prior art concentration sensors uses a platinum electrode. This sensor measures the oxidation current of hydrogen peroxide occurring on the platinum electrode to electrochemically determine the concentration of hydrogen peroxide ("Electrochemical Measuring Method, Volume 1", written by Fujishima, et al., and published by Gihodo Shuppan K.K., Nov. 15, 1984, pp. 238–239).

Another type prior art concentration sensor employs an electrode material for measuring the hydrogen peroxide concentration, and a molecule-recognizing substance such as enzyme, microorganism etc. Such concentration sensor is referred to by a biosensor, more specifically by a glucose sensor for use in measuring the blood sugar level or urine sugar level in blood or urine ("Advanced Sensor Handbook" written by Takahashi, et al., and published by K.K. Bifukan on May 20, 1994, pp. 335–339).

It is to be noted that each of these prior art concentration sensors aims at measuring a concentration of a single target substance and is not capable of measuring concentrations of plural target substance at the same time. Accordingly, the concentration of each target substance cannot be determined with one sensor where plural target substances are present in a system.

Further, in accordance with the prior art concentration measuring sensors and methods, a target substance would be influenced by other substances, resulting in a substantial decrease of accuracy of measurement. For example, the above-mentioned prior art hydrogen peroxide sensors determine hydrogen peroxide concentrations from oxidation current values of hydrogen peroxide when potentials of about +0.9 V (i.e. potential toward a reversible hydrogen electrode; every potential hereinafter described is referred to as a value toward a reversible hydrogen electrode) are applied to platinum electrodes. However, organic acids such as ascorbic acid, uric acid etc. would be oxidized at potentials of about +0.9 V, as well as hydrogen peroxide, so that the resulting oxidation current includes the oxidation currents of not only hydrogen peroxide but also of such organic acids. Accordingly, when this prior art concentration sensor is used for measuring hydrogen peroxide in a system containing organic acids such as ascorbic acid and uric acid, there would be a significant error in measurement.

For the same reason, there is a similar problem where blood glucose is measured by the above-described glucose sensor. When the glucose sensor is used, the following reaction (A) proceeds with a glucose oxidase catalyst:

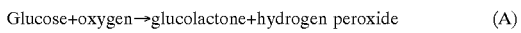

Glucose+oxygen→glucolactone+hydrogen peroxide        (A)

The amount of generated hydrogen peroxide is determined, and from the equivalent ratio, the glucose concentration is determined. Accordingly, the measurement of glucose in samples such as blood, urine etc. with the prior art glucose sensor is greatly influenced by ascorbic acid and uric acid present in blood or urine, so glucose concentrations cannot be accurately determined., similar to the above-described cases where hydrogen peroxide concentrations are determined in the system containing organic acids such as ascorbic acid, uric acid etc.

Further, molecular-recognizing substances such as glucose oxidase used in the glucose sensor are usually immobilized onto a film of substrates such as polymeric molecules etc. However, this has a poor stability and therefore could not used for a long time because of the elution of molecular-recognizing substances from the substrate, and reduction in the catalytic activity of the substances themselves.

Sensors using diamond as the electrode have also been known. For example, Japanese Patent Publication No. 2-22900 discloses an electrochemical test/analytical electrode consisting of diamond to which electrical conductivity has been added by ion injection. This publication also describes that such diamond electrode is favorably used as an electrochemical test/analytical indicator electrode because it has a wide potential region (potential window) free of hydrogen generation and oxygen generation (or metal elution) caused by electrolysis, and a low residual current (base current regarded as noise) in the potential window.

In Japanese Patent Laid-Open Publication No. 2-266253, it is disclosed that a conductive diamond layer, with impurities, is etched on a substrate by a gas phase method to produce an electrode, which is then coated with an enzyme-containing conductive resin to produce an enzyme sensor.

Japanese Patent Laid-Open Publication No. 8-240555 discloses a diamond film biosensor comprising a molecule-recognizing living body-related substance coated or immobilized on the surface of a transducer of a semiconductor diamond film.

Either of the sensors in the above-referenced two Japanese Patent Laid-Open Publications have a layer of a molecule-recognizing substance such as enzyme, microorganism etc. In fact, such molecule-recognizing substance layer adversely affects anti-corrosion and durability inherent in diamond itself. Further, each sensor merely measures a single substance. It is not at all suggested therein that concentrations of plural substances may be measured with a single sensor where there are plural substances in a system.

Studies on diamond electrodes have been rapidly increasing for the last few years. Among them, Swain et al. have used a diamond electrode to examine oxidoreduction characteristics of $Fe(CN)_6^{3-/4-}$, $Ru(NH3)_6^{3+/2+}$, $IrCl6^{2-/3-}$, 4-methylcathecol, dopamine, methyl viologen, ferrocene, hydroquinone, ascorbic acid etc., and made a conclusion that the diamond electrode is promising as a sensor [G. M. Swain et al., Anal. Chem., 67, (1995), 2812–2821; G. M. Swain et al., Electrochem. Soc. Proceedings, 96–9, (1996), 138–148]. In their report, however, a response is observed where a single substance is present in a system. No measurement of plural substances in a multi-component system is suggested therein.

Zhu et al. show the relationship between hydrogen peroxide concentrations and response electric currents when diamond electrodes were used [J. Z. Zhu et al., Fresenius J. Anal. Chem., 352, (1995), 389–392], but measurement of plural substances in a multi-component system is not suggested.

Measurement of a specific substance in a multi-component system by using an electrode other than the diamond electrode has been reported by Kita et al. They conducted-electrolytic oxidation of glucose by modifying the surface of a platinum electrode with a Nafion membrane [H. Kita et al., J. Electroanal. Chem., 382, (1995), 103–110]. They reported that glucose could be measured solely under no influence of ascorbic acid etc. by using Nafion membrane. However, the target substance measured by this method is glucose only. Other substances, such as ascorbic acid, can not be measured. Because the platinum electrode has a narrow potential window, measurable substances in this method must be limited. Accordingly, this method is not applicable to measurement of concentrations of plural target substances in a multi-component system. In addition, Nafion membrane has a poor durability.

Polarography having a mercury electrode has been used for measurement of a specific substance in a multi-component system, by utilizing superior charateristics of the mercury electrode, that is, a high hydrogen overvoltage and an extremely large potential window at the reduction region ("Electrochemical Measuring Method, Volume 1", written by Fujishima, et al., and published by Gihodo Shuppan K.K., Nov. 15, 1984, pp. 197–203). However, mercury is dissolved in an oxidization area so that application of polarography using the mercury electrode is limited to a reduction area and, therefore, measurable substances are limited. Further, unlike the conductive diamond electrode proposed in the present invention, selective measurement of substances by use of a difference in reaction potential cannot be conducted.

SUMMARY OF THE INVENTION

Under these circumstances, an object of the present invention is to provide a concentration sensor and a concentration measuring method in which concentrations of plural target substances can be accurately measured in a system where the plural target substances are present.

Another object of the present invention is to provide a novel concentration sensor that does not require any problematic layer such as a layer of molecular recognizing substance and a Nafion membrane on the surface of the electrode, to provide an improved durability.

Still another object of the present invention is to provide a concentration measurement technique applicable to a wider measurable area including both an oxidation area and a reduction area, and to a greater number of measurable substances.

The present invention has been completed based on the inventors' finding that a potential at which oxidation or reduction initiates (i.e., a reaction potential) of a substance in electrochemical reaction using a detection electrode of conductive diamond is often significantly different from the reaction potential of the same substance by use of an electrode of materials other than diamond.

Therefore, In accordance with an aspect of the present invention there is provided a method of measuring a concentration of a target substance in a sample, comprising the steps of preparing a concentration sensor with a detection electrode of conductive diamond; contacting said sample with said diamond detection electrode at a specific potential, to thereby monitor a response electric current resulting from reaction of said target substance on said diamond detection electrode; and determining a concentration of said target substance in reference to a predetermined relationship between an electric current and a concentration of said target substance at said specific potential.

In accordance with another aspect of the present invention there is provided a method of measuring concentrations of plural target substances in a sample, comprising the steps of preparing a concentration sensor with a detection electrode of conductive diamond; contacting said sample with the detection electrode at at least different two specific potentials, to thereby monitor response electric currents resulting from reaction of said target substances on said diamond detection electrodes at said different potentials, respectively; and determining concentrations of said target substances in reference to predetermined relationship between electric current and concentration for said first and second target substances.

The above-described method for measurement of plural target substances is applicable to the following cases:

(i) wherein at a first potential only a first one of said plural target substance provides its own response electric current, whereas at a second potential remote from said first potential only a second one of said plural target substance provides its own response electric current;

(ii) wherein at a first potential first and second ones of said plural target substance provide their own response electric currents, respectively, whereas at a second potential remote from said first potential only one of said first and second ones provides its own response electric current;

(iii) wherein at a predetermined positive potential only a first one of said plural target substance provides its own response electric current resulting from oxidation thereof, whereas at a predetermined negative potential only a second one of said plural target substance provides its own response electric current resulting from reduction thereof;

(iv) wherein at a predetermined positive potential first and second ones of said plural target substance provide their own response electric currents resulting from oxidation thereof, respectively, whereas at a predetermined negative potential only one of said first and second ones provides its own response electric current resulting from reduction thereof; and (v) wherein at a predetermined negative potential first and second ones of said plural target substance provide their own response electric currents resulting from reduction thereof, respectively, whereas at a predetermined positive potential only one of said first and second ones provides its own response electric current resulting from oxidation thereof.

In accordance with still another aspect of the present invention there is provided a method of measuring concentrations of plural target substances in a sample, comprising the steps of preparing a concentration sensor with a first detection electrode of conductive diamond and a second detection electrode of materials other than conductive diamond; contacting said sample with said first and second detection electrodes, to thereby monitor response electric currents resulting from reaction of said target substances on said first and second detection electrodes, respectively; and determining concentrations of said target substances in reference to predetermined relationship between electric current and concentration for said first and second target substances.

This method is applicable to the case wherein oxidation/reduction characteristics of said plural target substances are substantially the same on said second detection electrode but are different on said first detection electrode. In particular, said plural target substances initiate oxidation/reduction at remote potentials on said first detection electrode.

This method is also applicable to the case wherein a first one of said plural target substances provide its own response electric currents at remote potentials on said first and second detection electrode, respectively, whereas a second one of said plural target substances provides its own response electric currents at substantially the same potential on said first and second detection electrode.

In accordance with still another aspect of the present invention there is provided a concentration sensor comprising a detection electrode of conductive diamond, a counter electrode, a reference electrode, and means for applying a predetermined potential to each of said electrodes, each of said electrodes being in contact with a sample containing one or more of target substances.

In accordance with still another aspect of the present invention there is provided a concentration sensor comprising a detection electrode of conductive diamond, a counter electrode of materials other than conductive diamond, a reference electrode, and means for applying a predetermined potential to each of said electrodes, each of said electrodes being in contact with a sample containing one or more of target substances.

In accordance with still another aspect of the present invention there is provided a concentration sensor comprising a counter electrode of conductive diamond, a detection electrode of materials other than conductive diamond, a reference electrode, and means for applying a predetermined potential to each of said electrodes, each of said electrodes being in contact with a sample containing one or more of target substances.

In accordance with still another aspect of the present invention there is provided a concentration sensor comprising a first detection/counter electrode of conductive diamond, a second detection/counter electrode of materials other than conductive diamond, a reference electrode, and means for applying a predetermined potential to each of said electrodes, each of said electrodes being in contact with a sample containing one or more of target substances, said first and second detection/counter electrode being switchably operated as a detection or counter electrode in response to potential to be received from said means.

In accordance with still another aspect of the present invention there is provided a concentration sensor comprising a first detection electrode of conductive diamond, a second detection electrode of materials other than conductive diamond, a counter electrode, a reference electrode, and means for applying a predetermined potential to each of said electrodes, each of said electrodes being in contact with a sample containing one or more of target substances.

In the concentration sensor of the present invention, the detection electrode of conductive diamond may be an electrode of a rotating disk type.

Materials other than conductive diamond of the detection electrode in the concentration sensor of the present invention may be selected from the following groups (i)–(6):

(i) a group consisting of metals and alloys;

(ii) a group consisting of metal oxides;

(iii) a group consisting of semiconductors;

(iv) a group consisting of carbon-based materials;

(v) a group consisting of metal sulfides;

(vi) a group consisting of materials wherein the surface of the material in the group (i)–(v) is covered with a covering material selected from the group consisting of metals, alloys, inorganic compounds, organic compounds, ploymeric compounds and living body related substances.

The electrode using conductive diamond has a significantly broader potential window for water than electrodes made of materials other than conductive diamond. Accordingly, the concentration measuring method and concentration sensor of the present invention is capable of detecting the electrochemical reactions of various substances and determining the concentrations thereof. Furthermore, the electrode using conductive diamond has too low residual current, and thus the concentration measuring method and concentration sensor of the present invention have a good S/N ratio and high sensitivity.

BRIEF DESCRIPTION OF THE DRAWINGS

The above and other objects of the present invention will be apparent from the following description when read in conjunction with the accompanying drawings in which.

DETAILED DESCRIPTION OF THE INVENTION

Fundamental Principle for Measurement of a Single Target Substance

Concentration of a single target substance A in a sample containing only substance A is measured by the fundamental principle described hereinbelow. The fundamental principle is also applicable, with necessary modification, to measurement of concentrations of plural target substances A, B etc., as described later.

Figure 13:
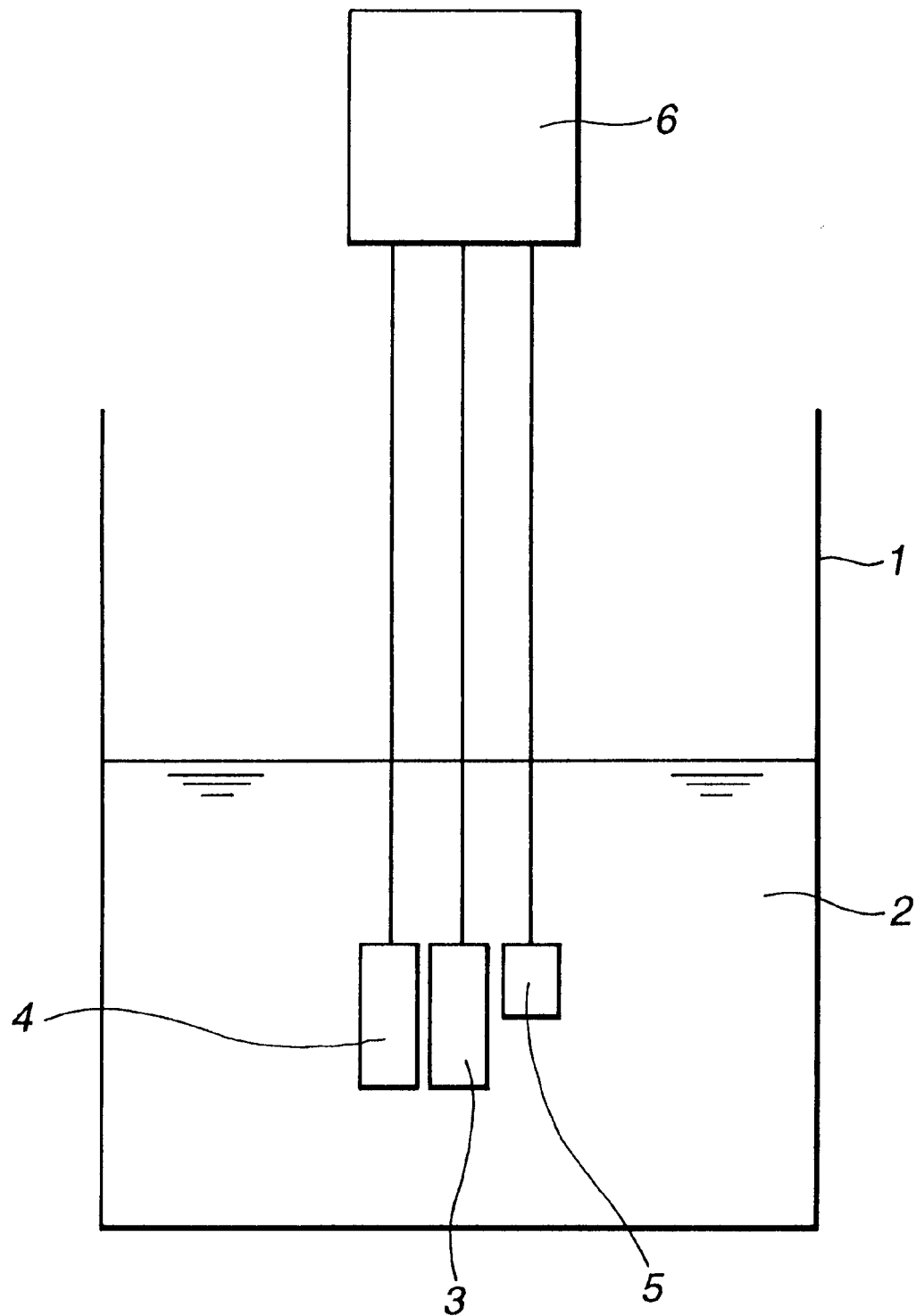
FIG. 13 diagrammatically shows a concentration sensor embodying the present invention for use in measurement in accordance with the fundamental measurement principle.

An electrochemical measuring apparatus (that is, a concentration sensor) used for conducting the electrode reaction in the fundamental measurement principle is diagrammatically shown in FIG. 13. An electrolyte chamber 1 receives an electrolyte 2 containing a target substance. A detection electrode 3 with a film of conductive diamond, a counter electrode 4 made of any desired electrode material, and a reference electrode 5 are immersed in electrolyte 2. Electrodes 3, 4, 5 are arranged such that they can be energized by a voltage applicator 6 such as a potentiostat, a dry cell, a direct current power source and any other device capable of applying voltage to the respective electrodes.

Figure 1:
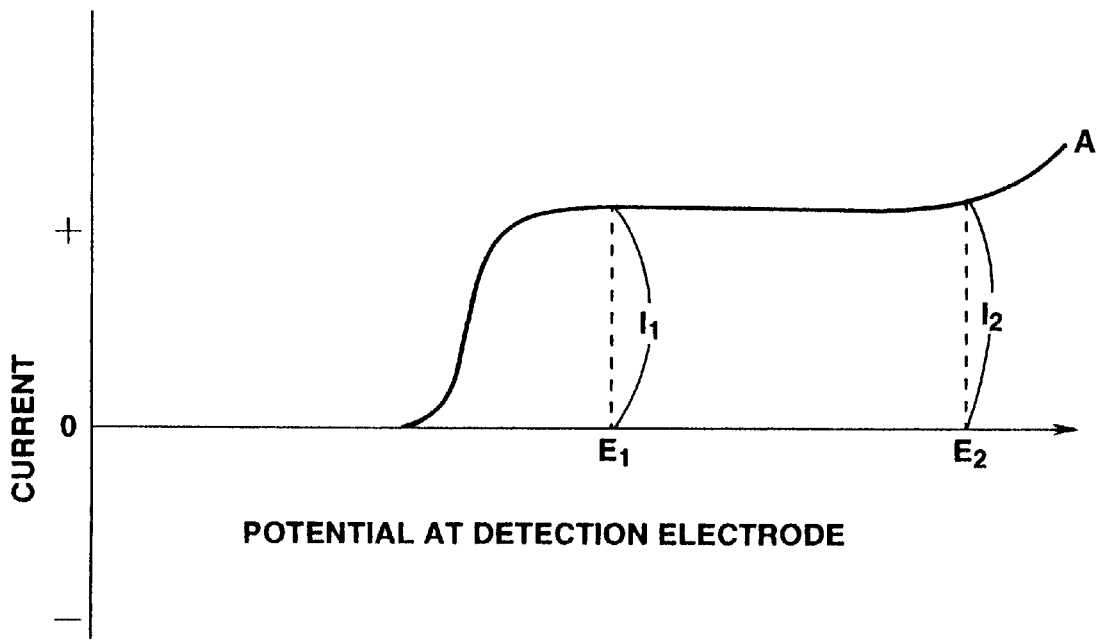
FIG. 1 is a current-potential curve showing relationship between electric current and potential at a diamond detection electrode when a sample containing only one target sbustance A is subjected to measurement.

FIG. 1 is a conceptual patterned graph of electric current-potential curve at the detection electrode where a sample containing only one target substance A was subjected to electrochemical reaction with the electrochemical measuring apparatus such as shown in FIG. 13 using conductive diamond detection electrode 3. In the electric current-potential curve in FIG. 1, an electric current value $I_1$ is substantially constant at a relatively wide potential range including a potential $E_1$. When a potential exceeds a critical point, an electric current value flowing on the surface of the diamond detection electrode begins increasing. At a potential $E_2$, an electric current value $I_2$ is obtained. A greater electric current value is obtained at a greater potential.

Figure 2:
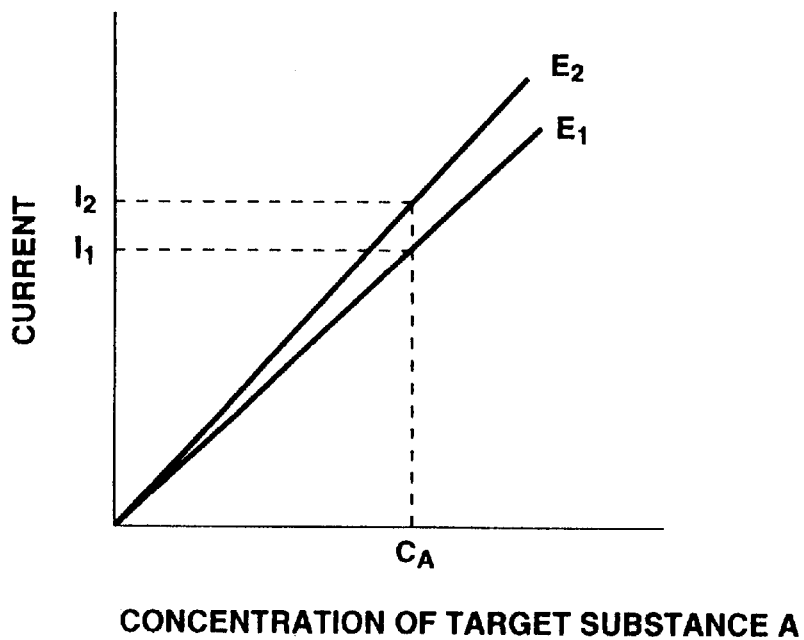
FIG. 2 shows relationship between response electric current at potentials $E_1$ and $E_2$ and concentration of the target substance A.

FIG. 2 shows a relationship between substance concentrations and response electric currents at potentials $E_1$ and $E_2$. The potential may be set at any value insofar as the target substance reacts at that potential, but it is preferabe to select a potential in the region where the diffusion of the substance onto the surface of the electrode is almost constant and, therefore, the response electric current becomes almost constant, in order to minimize measurement errors.

In FIG. 1, if the electric current value $I_1$ is actually obtained at the potential $E_1$, a concentration $C_A$ of target substance A can be obtained from the proportional relational line $E_1$ in FIG. 2. Because the set potential $E_1$ is within the region where the response electric current becomes almost constant, an experiment can be conducted to obtain a reliable graph showing the relationship between the electric current and the concentration of the target substance A. Although the electric current value $I_2$ is obtained at a potential $E_2$ in the region where the reaction of the substance on the surface of the electrode becomes more active and the response electric current is not constant, this current value also has a one-to-one relationship with a specific potential value ($E_2$), which can be used in a similar manner to determine the concentration $C_A$ from the proportional relational line $E_2$ in FIG. 2.

The diamond electrode has a wide potential window. Accordingly, the concentration measuring method of the present invention allows a significantly increased number of target substances to be measured, as compared with the conventional methods using a platinum electrode, for example. Less residual current (that is, background electric current) of the diamond electrode and its high S/N ratio provide improved measurement accuracy.

In accordance with the present invention, concentrations of plural target substances in a multi-component system can be measured. Measurement of plural target substance concentrations is hereinbelow classified roughly into measurement patterns I, II and III in which the above-described fundamental principle applicable to measurement of a single target substance concentration is modified upon demand. The method of measuring the concentrations of plural different target substances may be any combination of measurement patterns I, II and III. By combining plural measurement patterns, concentrations of three or more target substances can be determined.

Pattern I for Measurement of Plural Substance Concentrations by Single Use of a Diamond Electrode This measurement pattern I describes a method of determining concentrations of substances A and B in a system by measuring electrochemical reaction with an electrochemical measuring apparatus (i.e., a concentration sensor) using a single conductive diamond electrode as the detection electrode. This measurement pattern I is a measuring method utilizing the difference in oxidation initiating or reduction-initiating potential between the target substances, which is particularly suitable to the case where the target substances A and B have quite different potential values at which they initiate oxidation or reduction.

The electrochemical measuring apparatus shown in FIG. 13 used in the fundamental measuring principle can also be used for conducting the electrode reaction in this measurement pattern I.

Figure 3:
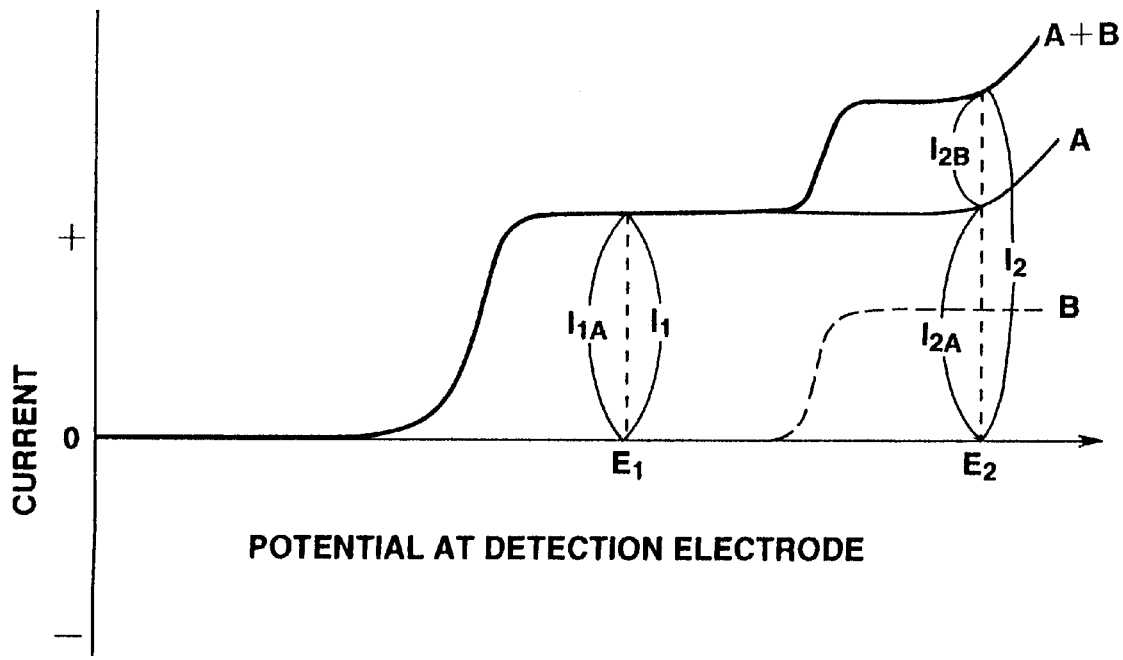
FIG. 3 is a current-potential curve showing relationship between electric current and potential at a diamond detection electrode when a sample containing two target substances A and B is subjected to measurement.

FIG. 3 is a conceptual patterned graph showing the relationship between electric currents and potentials at the detection electrode where a sample containing target substances A and B was subjected to electrochemical reaction in the above electrochemical measuring apparatus. The curve A+B in FIG. 3 represents a total sum of the electric current values, that is, an electric current obtained by the curve A for the first target substance A plus another electric current obtained by the curve B for the second target substance B. The curves A and B for the target substances A and B have been prepared by previous measurement. In FIG. 3, since the electric current value of substance B at potential $E_1$ is zero, the resulting electric current value at this potential $E_1$ merely represents the reaction result of the target substance A on the surface of the electrode. The resulting electric current value at potential $E_2$ represents the sum of the reaction results of the target substances A and B on the surface of the electrode.

A straight line showing the proportional relationship between electric currents and concentrations of the target substance A at potential $E_1$ was prepared in advance. Likewise, a straight line showing the proportional relationship between electric currents and concentrations of the target substance A concentration at potential $E_2$ is prepared in advance. The diamond electrode is make operative in a system where the target substances A and B are present. If the electric current value $I_1$ is obtained at potential $E_1$, since the current value $I_1$ is identical to the current value $I_{1A}$ resulting from oxidation of the target substance A as shown in FIG. 3, concentration $C_A$ of the target substance A can be measured from the relational line of FIG. 2 showing the proportional relationship between the oxidation current value and the concentration. This is substantially the same manner measurement as in the previous case where the fundamental measurement principle is applied for measurement of a single substance concentration.

Figure 4:
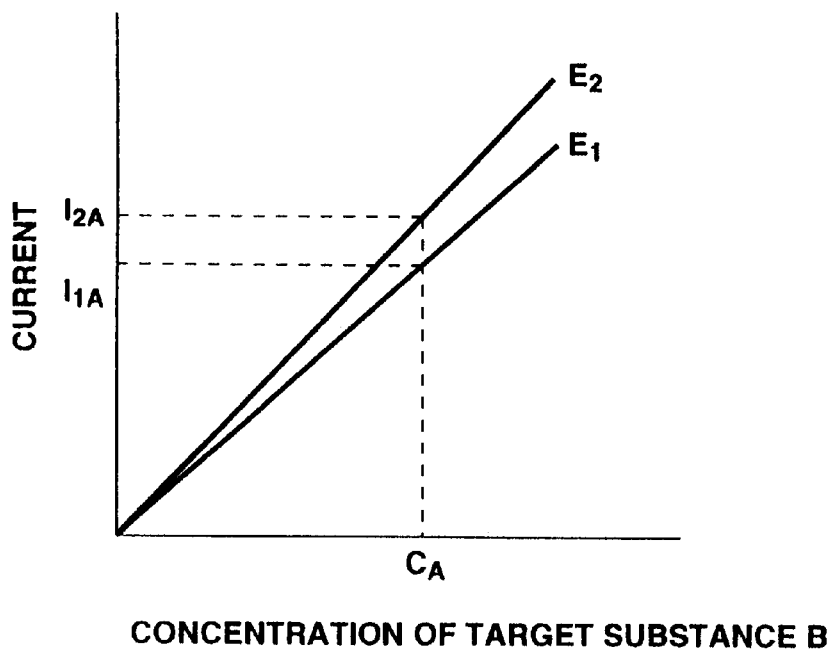
FIG. 4 shows relationship between response electric current at oxidation potentials $E_1$ and $E_2$ and concentration of the target substance A.
Figure 5:
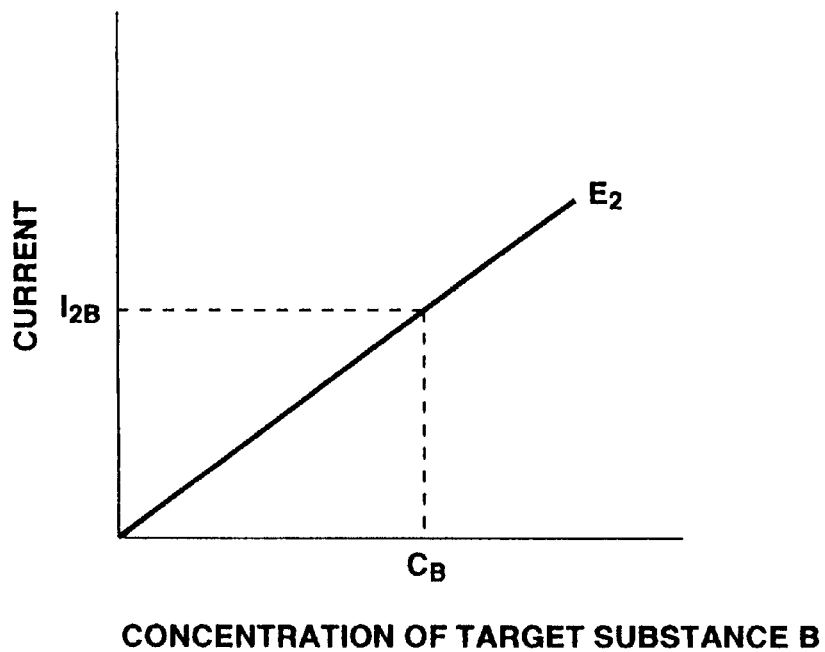
FIG. 5 shows relationship between response electric current at an oxidation potential $E_2$ and concentration of the target substance B.

Since it has been confirmed that the target substance A is present in the A+B system at a concentration $C_A$, the electric current value at potential $E_2$ of the target substance A can be determined as $I_{2A}$ from the relational line of FIG. 4. Then, the electric current value $I_{2B}$ of the target substance B at potential $E_2$ is determined by subtracting the previously obtained electric current value $I_{2A}$ of the target substance A from the total electric current value $I_2$. Then, the concentration $C_A$ of the target substance B is determined from the already prepared relational line of FIG. 5 showing the proportional relationship between oxidation electric currents and concentrations of the target substance B at potential $E_2$.

Pattern II for Measurement of Plural Substance Concentrations by Use of a Diamond Electrode in combination with Another Material Electrode This measurement pattern II is a method of measuring concentrations of target substances A and B respectively, for example, by measuring the electrochemical reaction of these target substances A and B in the electrochemical measuring apparatus in which a detection electrode made of conductive diamond and another detection electrode made of materials other than conductive diamond are used in combination. This measurement pattern II is particularly suitable to measurement where the oxidation potentials of the target substances A and B are apart from each other at the diamond electrode or only one of them is oxidized thereat, while the target substances A and B have almost equal oxidation characteristics at the electrode made of materials other than conductive diamond, e.g. platinum.

Figure 14:
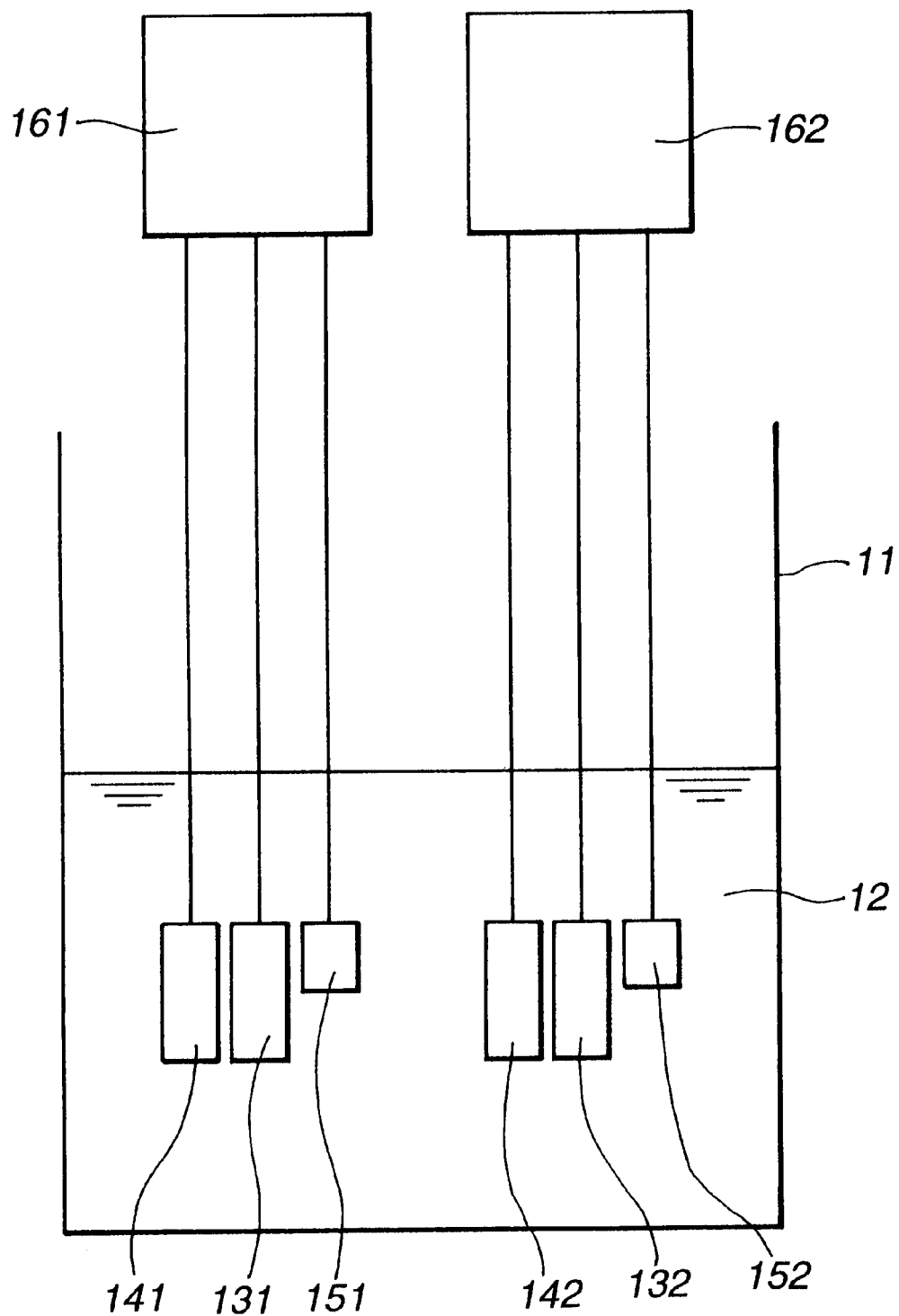
FIG. 14 diagrammatically shows a concentration sensor embodying the present invention for use in measurement in accordance with the measurement pattern I.

FIG. 14 illustrates an electrochemical measuring apparatus (a concentration sensor) embodyig the present invention which can be used for measuring concentrations of plural target substances in accordance with the measuriement pattern II. As shown in FIG. 14, a first electrode group (i) and a second electrode group (ii) are immersed in an electrolyte chamber 11 receiving electrolyte 12 containing target substances A and B. The first electrode group (i) consists of a first detection electrode 131 made of conductive diamond, a first counter electrode 141 and a first reference electrode 151. Each of the electrodes 131, 141, 151 is connected to a first voltage applicator 161. Likewise, the second electrode group (ii) consists of a second detection electrode 132 made of materials other than conductive diamond, which is typically a platinum electrode, a second reference electrode 142 and a second reference electrode 152, each electrodes being connected to a second voltage applicator 162.

Figure 6:
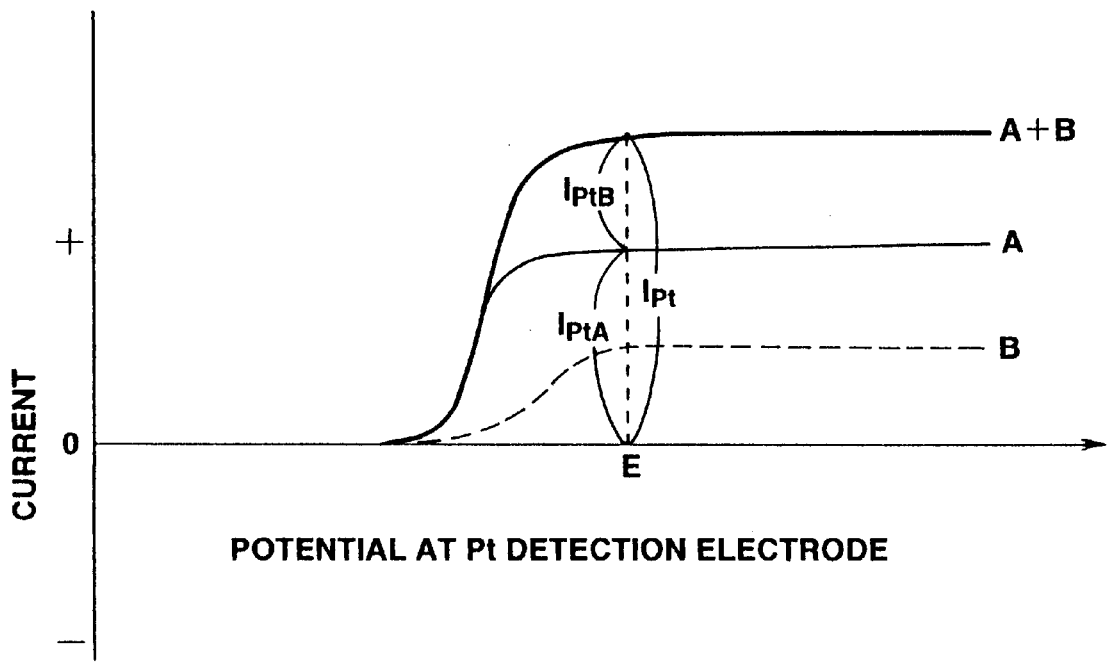
FIG. 6 is a current-potential curve showing relationship between electric current and potential at a platinum detection electrode when a sample containing two target sbustances A and B is subjected to measurement.

Suppose the first and second electrode groups (i) and (ii) are both in operation with the electrochemical measuring apparatus of FIG. 14. There is a current-potential relationship curve A+B as shown in FIG. 6 at the second detection electrode 132 of platinum of the second electrode group (ii), which represents the sum of the current-potential curves of the target substances A and B. In this case, the target substances A and B show similar oxidation characteristics and therefore similar current-potential curves as far as the detection electrode (132) is made of platinum or other material but not conductive diamond.

Figure 7:
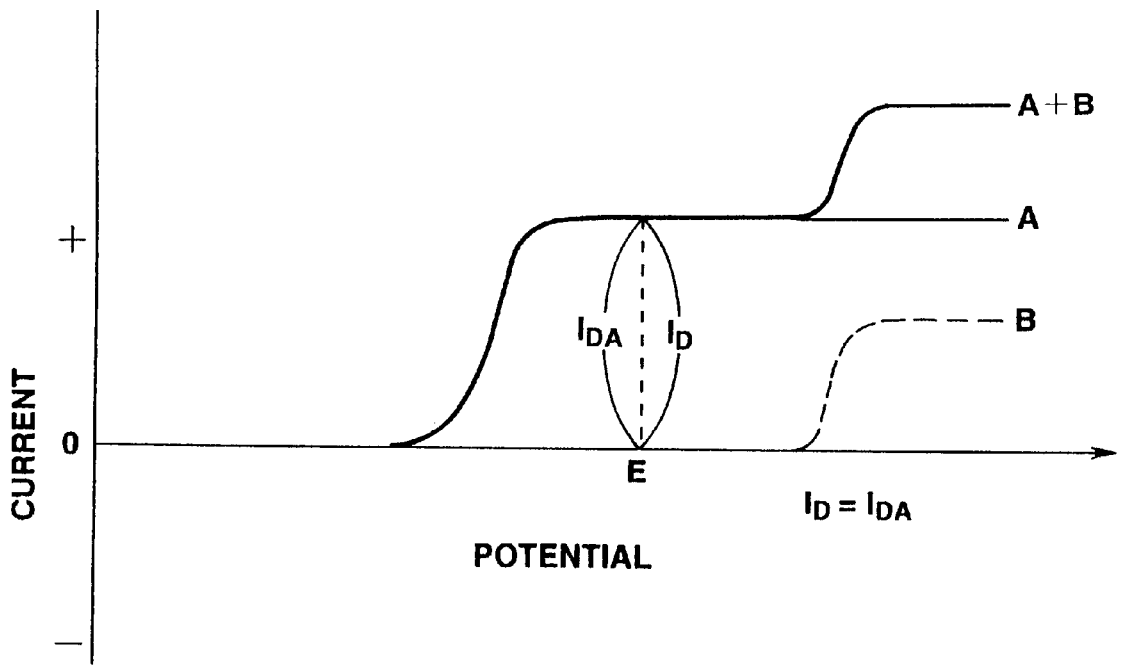
FIG. 7 is a current-potential curve showing relationship between electric current and potential at a diamond detection electrode when a sample containing two target sbustances A and B is subjected to measurement.

However, the target substances A and B has quite different oxidation characteristics at the detection electrode of the first electrode group (i) which is made of conductive diamond, as demonstrated by current-potential relationship curves of the target substances A and B at the diamond electrode 131 in FIG. 7. FIG. 7 also depicts a current-potential curve A+B representing the sum of the curves of the target substances A and B. These curves in FIG. 7 are similar to those in FIG. 3. The measurement pattern II is suitably applicable where the target substances A and B have the above-described characteristics.

Figure 8:
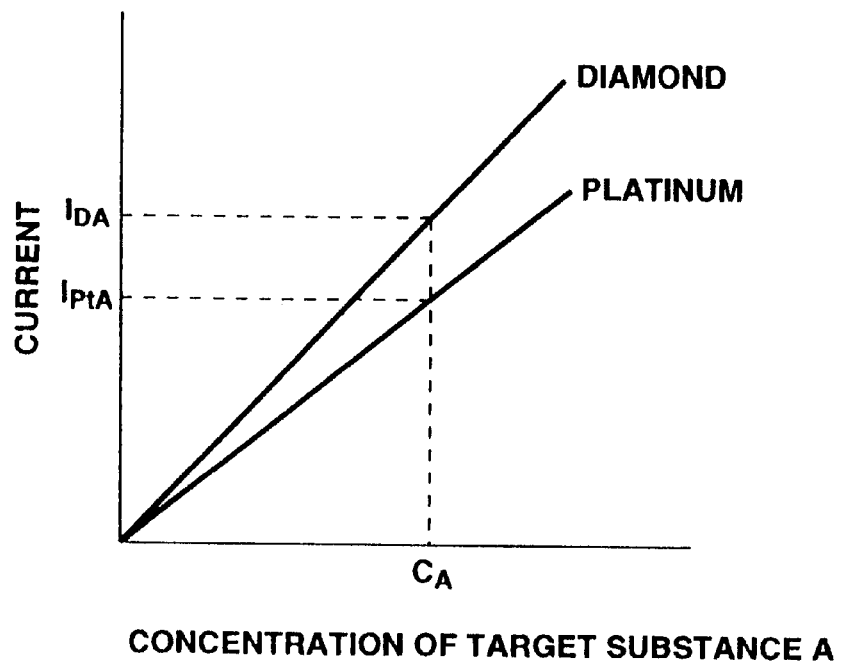
FIG. 8 shows relationship between response electric current on the platinum and diamond electrodes and concentration of the target substance A.

When the same potential E was applied to the electrode groups (i) and (ii), an oxidation current value $I_{Pt}$ is measured at the second detection electrode or platinum electrode 132 as shown in FIG. 6, while an oxidation current value $I_D$ is measured at the first detection electrode or diamond electrode 131 as shown in FIG. 7. Because the oxidation current value $I_D$ is equal to the oxidation current value $I_{DA}$ of the target substance A, the concentration $C_A$ of the target substance A can be determined from the relational line of FIG. 8 which has been prepared to represent the relationship between the response electric current values at the platinum electrode and the diamond electrode and the concentration of the target substance A. From the determined concentration $C_A$ of the target substance A, its oxidation current value $I_{PtA}$ at the platinum electrode can be determined in reference to the relationship for the platinum electrode in FIG. 8.

Figure 9:
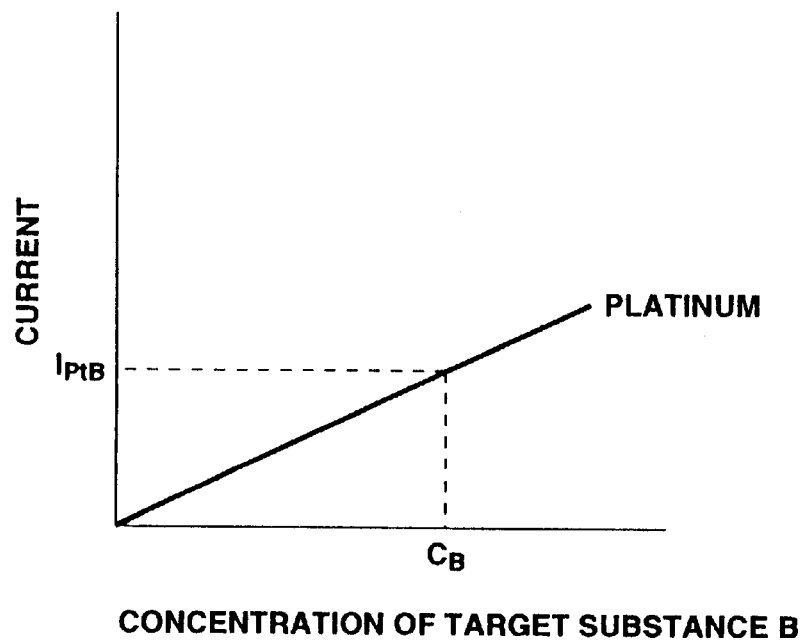
FIG. 9 shows relationship between response electric current on the platinum electrode and concentration of the target substance B.

The oxidation current value $I_{Pt}$ measured at the potential E on the platinum electrode is the sum of the oxidation current value $I_{PtA}$ of the target substance A and the oxidation current value $I_{PtB}$ of the target substance B. Accordingly, by subtracting from the oxidation current value IPt the oxidation current value IPtA of the target substance A at the potential E, an oxidation current value IPtB of the target substance B can be determined (see FIG. 6). From the determined oxidation current value IPtB of the target substance B, its concentration CB can be determined in reference to the line showing the relationship between the response electric current at the platinum electrode and the concentration of the target substance B in FIG. 9, which has been prepared in advance.

The measurement pattern II utilizes the target substances A and B have quite different oxidation potentials at the diamond electrode. In this sense, this measurement pattern II is similar to the measurement pattern I. However, this measurement pattern II allows application of only one, and relatively low potential, and therefore is particularly useful when it is not recommended, by some reason, to apply a high potential to a system to be measured.

Figure 15:
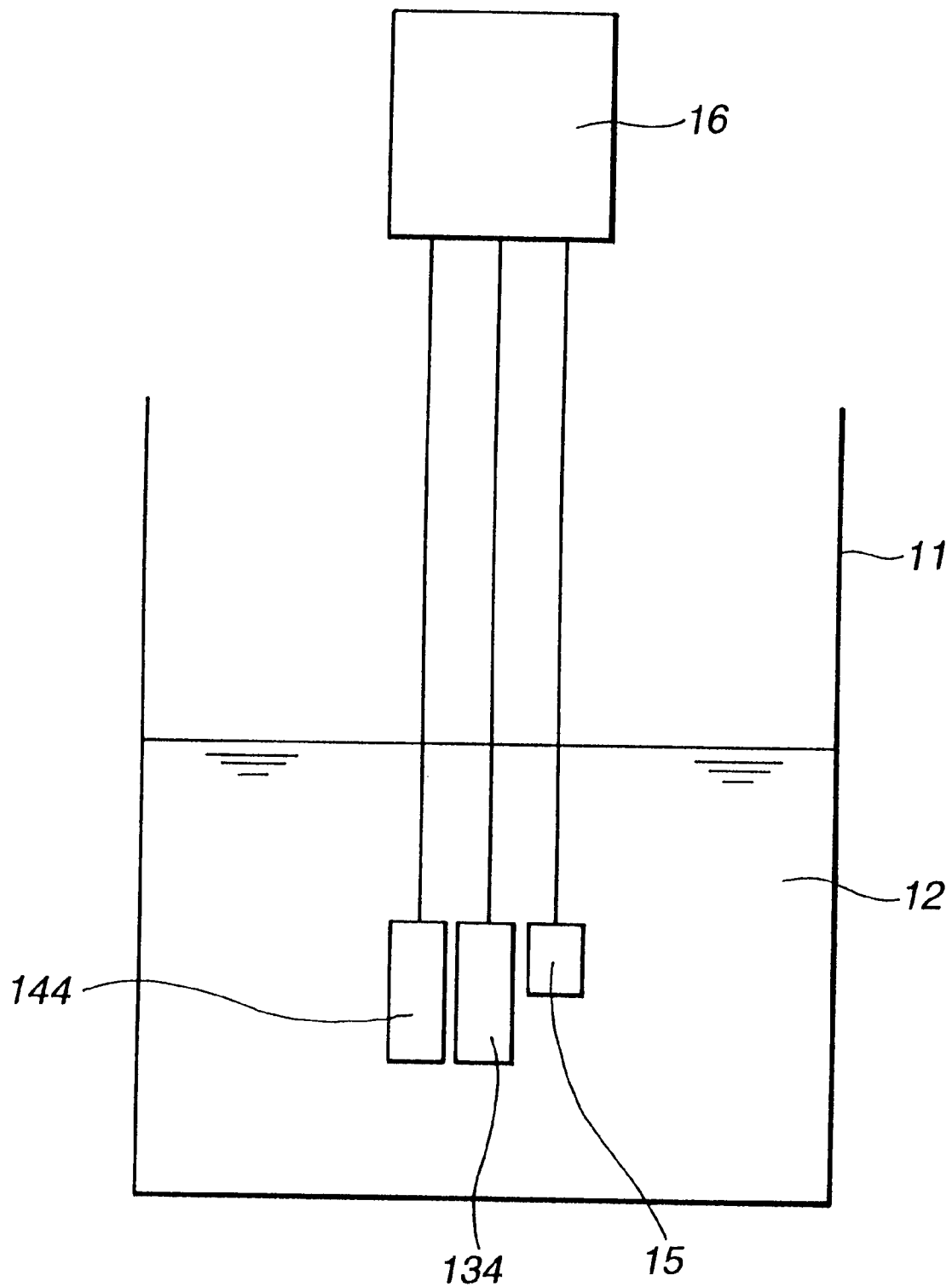
FIG. 15 diagrammatically shows another embodiment of the concentration sensor for use in measurement in accordance with the measurement pattern II.

Although the apparatus for use in this measurement pattern II is shown by way of example in FIG. 14, another electrochemical measuring apparatus (i.e., concentration sensor) such as shown in FIG. 15 can also be used, which has a simplified construction and includes a single electrode group consisting of a detection/counter electrode 134 of conductive diamond, a counter/detection electrode 144 made of materials other than diamond, and a reference electrode 15. In this concentration sensor, both the electrodes 134 and 144 are double-functional electrodes and, when one is used as a detection electrode the other acts as a counter electrode.

Figure 16:
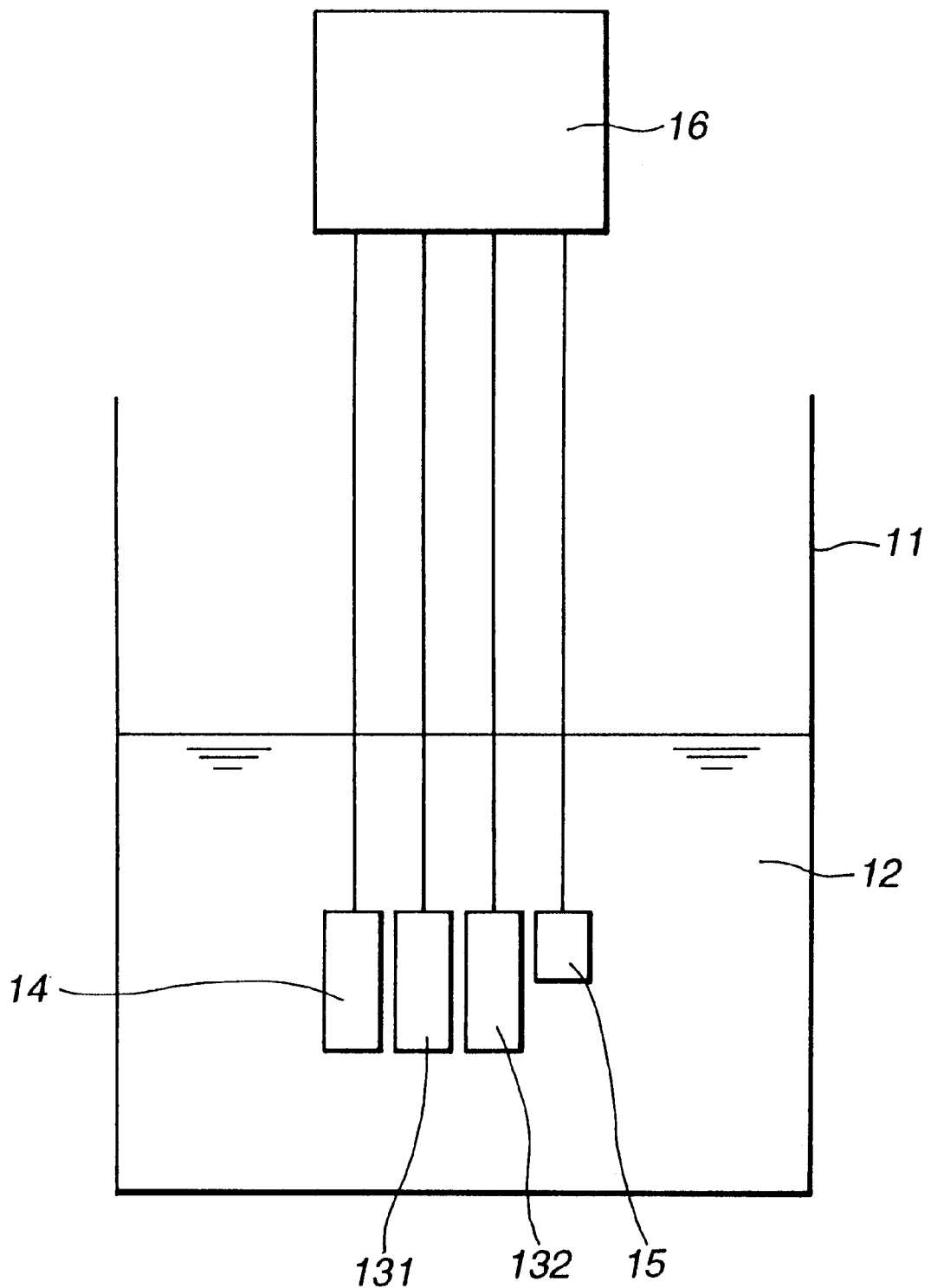
FIG. 16 diagrammatically shows still another embodiment of the concentration sensor for use in measurement in accordance with the measurement pattern II.

FIG. 16 shows another example of the apparatus for carrying out concentration measurement in accordance with the measurement pattern II. In this concentration sensor, a single electrode group consisting of a first electrode 131 of conductive diamond, a second detection electrode 132 made of materials other than conductive diamond, for example a platinum electrode, a counter electrode 14 and a reference electrode 15 is immersed in an electrolyte 12. The concentration sensor of FIG. 16 has a single counter electrode 14 and a single reference electrode 15 for two different kinds of detection electrodes 131, 132, thus achieving the reduced number of parts and space-saving merit in comparison with the embodiment shown in FIG. 16.

Figure 10:
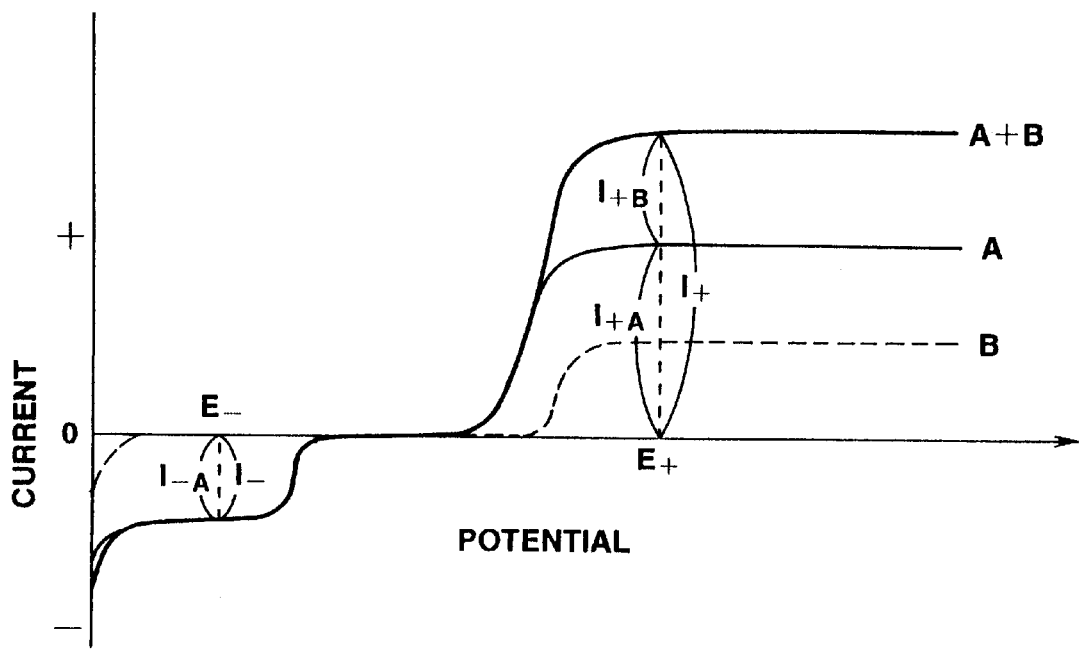
FIG. 10 is a current-potential curve showing relationship between electric current and potential at a diamond detection electrode when a sample containing two target sbustances A and B is subjected to measurement.

Pattern III for Measurement of Plural Substance Concentrations by Sole Use of a Diamond Electrode This measurement pattern III is applicable to the case where one of target substances A and B provides both of oxidation and reduction currents while the other target substance provides oxidation or reduction current, an example of which is shown in FIG. 10. In this example, a target substance A provides oxidation and reduction currents while a target substance B provides an oxidation current only. This is demonstrated by comparison between the line of FIG. 11 which represents the relationship between the response current value of the target substance A at the diamond electrode and the concentration thereof and the line of FIG. 12 which represents the relationship between the response current value of the target substance B at the diamond electrode and the concentration thereof.

Now, the conductive diamond electrode begins operation in a system where the target substances A and B are present, thereby obtaining a curve representing the relationship between the potential applied to the diamond electrode and the electric current values thereat with respect to the target substances A and B, as shown in FIG. 10. The sum of these curves is also shown in FIG. 10 as a curve A+B. As shown in FIG. 10, a reduction electric current value I− is measured at a potential E−, and an oxidation electric current value I+ is measured at a potential E+. Since the target substance B is not reduced at the potential E− (see FIG. 9), the total reduction electric current value I− is equal to the reduction electric current value I−A, which is plitted to the line of FIG. 11 to finally determine the concentration CA of the target substance A.

Figure 11:
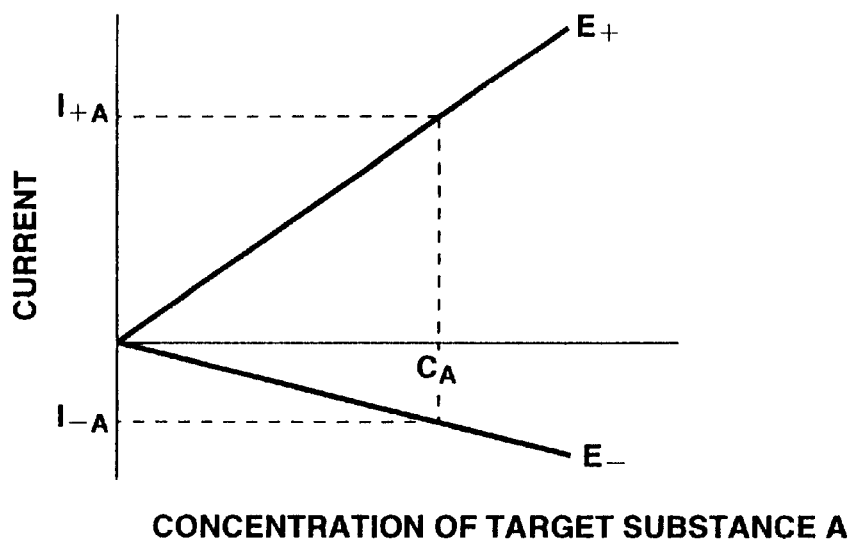
FIG. 11 shows relationship between response electric currents at an oxidation potential E+ and at a reduction potential E− and concentration of the target substance A.
Figure 12:
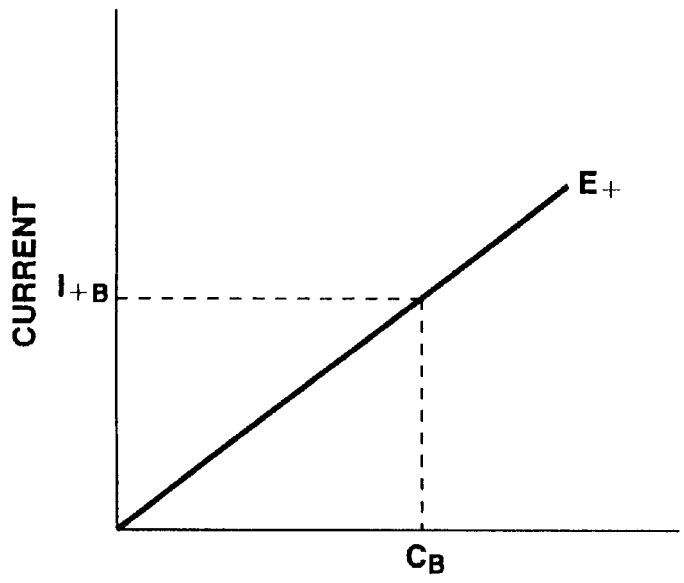
FIG. 12 shows relationship between response electric currents at an oxidation potential E+ and concentration of the target substance B.

Once the concentration CA of the target substance A is determined, its oxidation electric current value I+A can easily be determined again in reference to the line of FIG. 11. The oxidation electric current value I+B of the target substance B is determined by subtracting the determined value I+A from the total oxidation electric current value I+ of the curvee A+B shown in FIG. 10. This value I+B is plotted to the line of FIG. 12 to finally determine the concentration CB of the target substance B.

FIG. 13 shows an example of the electrochemical measuring apparatus or concentration sensor that can be used for measurement in accordance with the measurement pattern III.

Further Examples of Concentration Sensor

Figure 17:
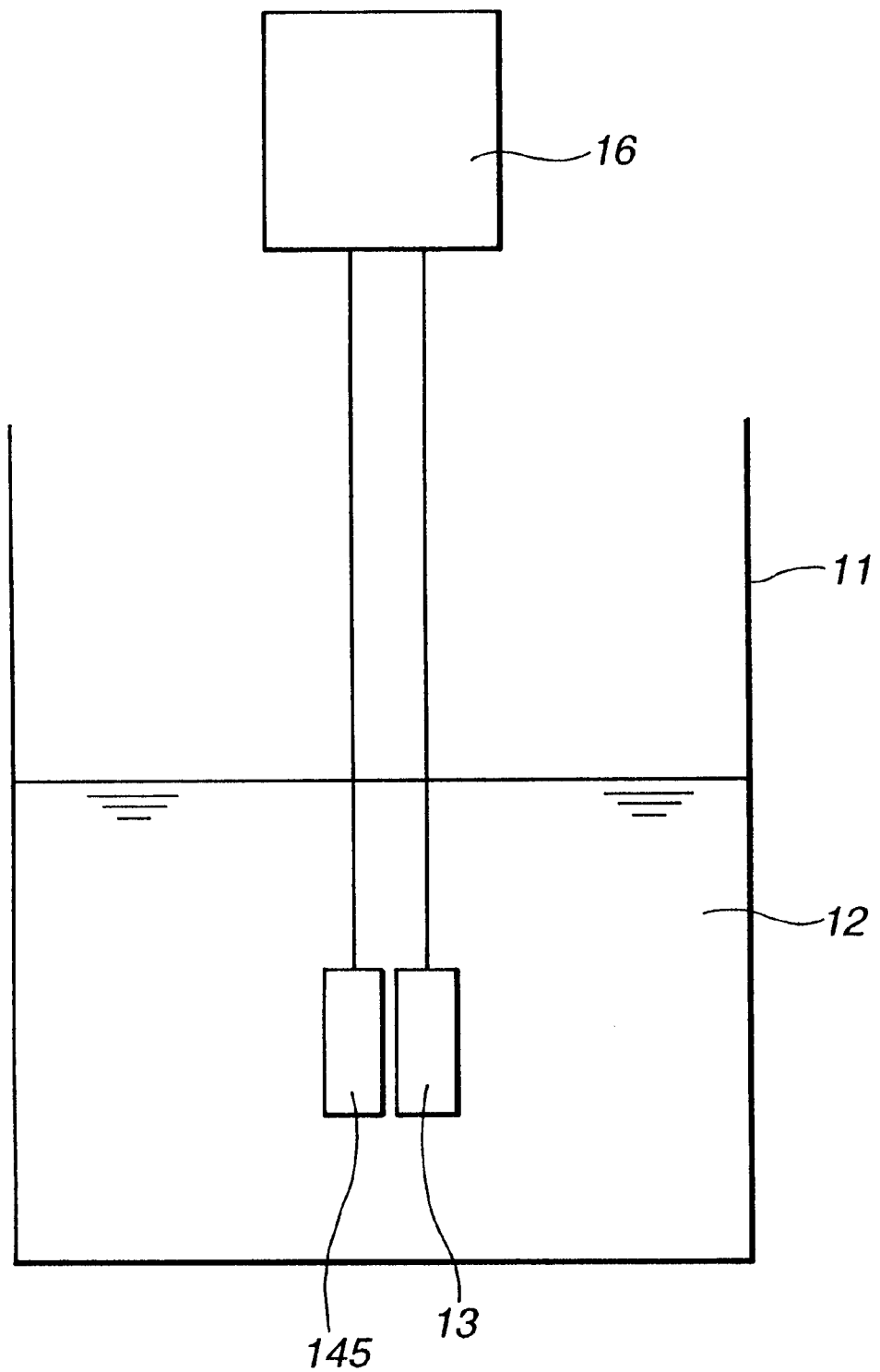
FIG. 17 diagrammatically shows an embodiment of the concentration sensor for use in measurement irrespective of the measurement patterns.
Figure 18:
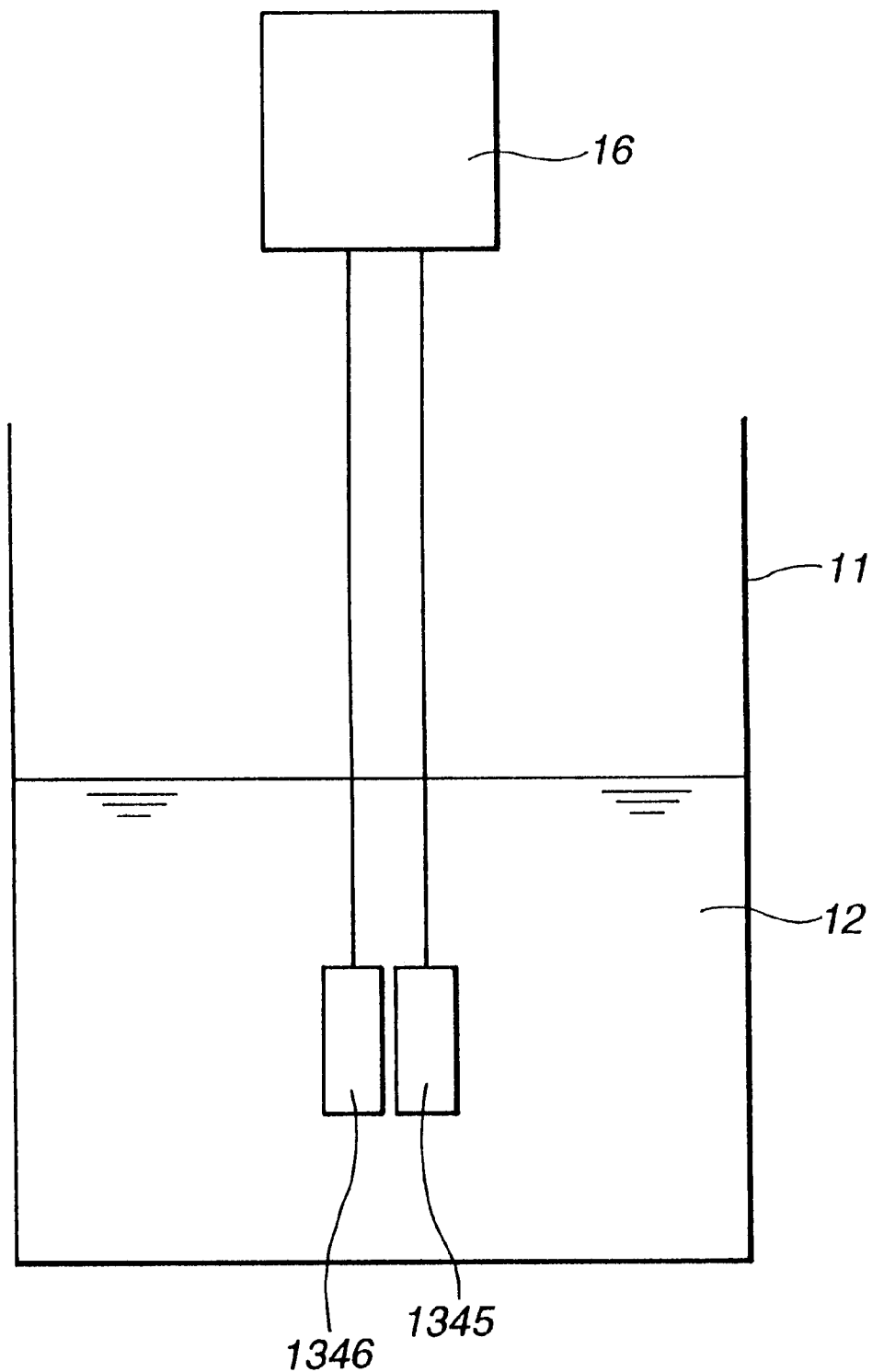
FIG. 18 diagrammatically shows another embodiment of the concentration sensor for use in measurement irrespective of the measurement patterns.

FIGS. 17 and 18 respectively show modified arrangement of the electrochemical measuring apparatus or concentration censor, which can be used for concentration measurement irrespective of measurement patterns I, II and III. These concentration sensors are characterized in that a counter electrode also acts as a reference electrode. The concentration sensor of FIG. 17 has a diamond detection electrode 13 and a counter/reference electrode 145, whereas the concentration sensor of FIG. 18 has a detection/counter/reference electrode 1345 made of diamond and a detection/counter/ reference electrode 1346 made of materials (e.g. platinum) other than diamond. These concentration sensors will be suitable for use in a system where the surface area of the counter electrode is significantly larger than that of the detection electrode, e.g. in an microelectrode.

Figure 19:
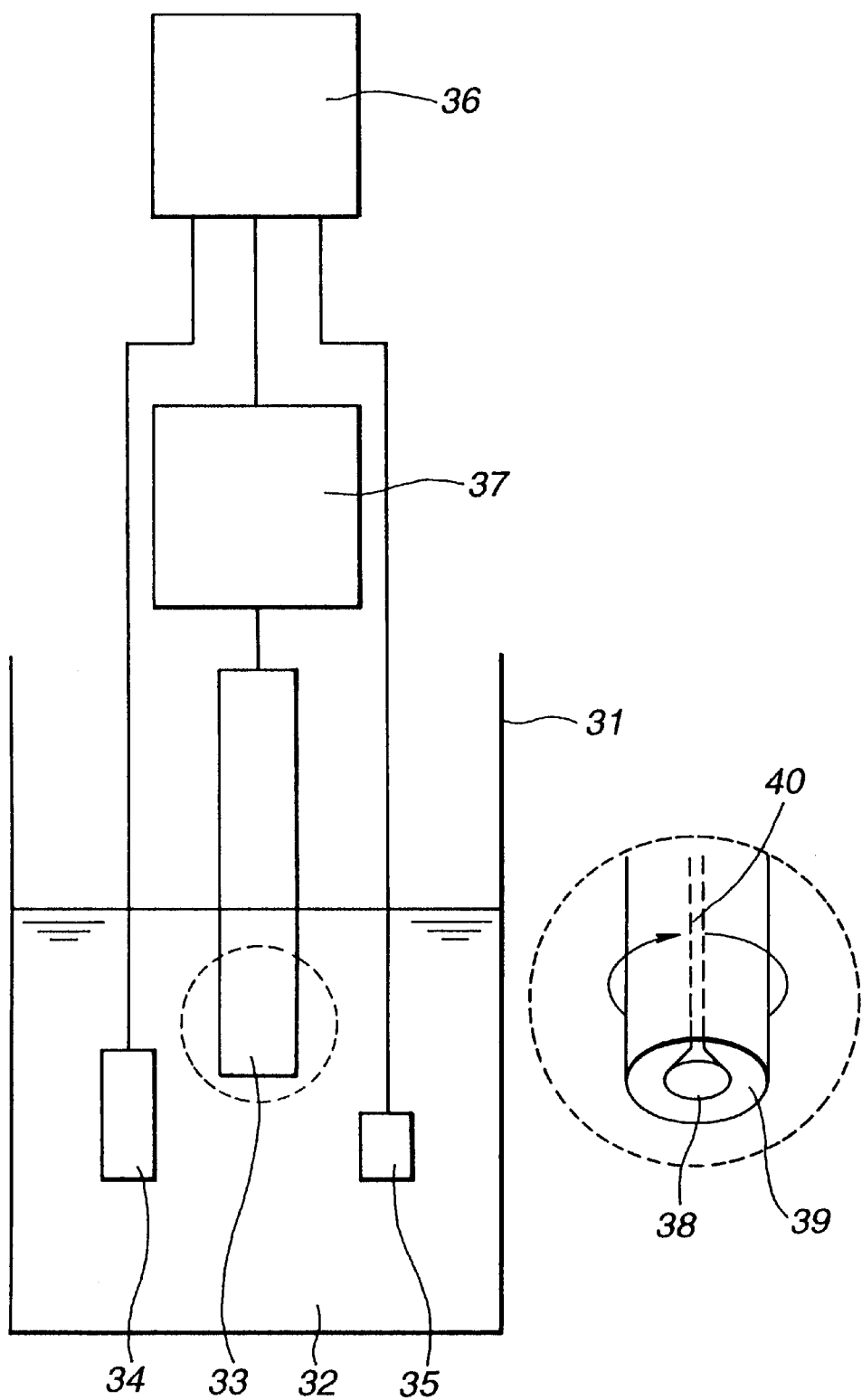
FIG. 19 diagrammatically shows an embodiment of the concentration sensor with a rotating disk diamond detection electrode.

FIG. 19 shows a concentration sensor embodying the present invention, wherein a rotational disk electrode is used as a detection electrode. An electrolysis chamber 31 receives an electrolyte 32 containing target substances. A detection electrode 33 that is a rotational disk electrode, a counter electrode 34 and a reference electrode 35 are immersed in the electrolyte 32. The detection electrode 33 is in communication with rotational driving mechanism 37 for rotating. These electrodes 33, 34, 35 are energized by a voltage applicator 36 such as a potentiostat or the like.

In the enlarged drawing in the broken circle in FIG. 19, at the bottom of the clyindrical detection electrode 33, a diamond electrode 38 consisting of a thin film of conductive diamond is surrounded by an electrically insulating layer 39. A lead 40 in communication with the rotational driving mechanism 37 is connected to the diamond electrode 38.

Figure 20:
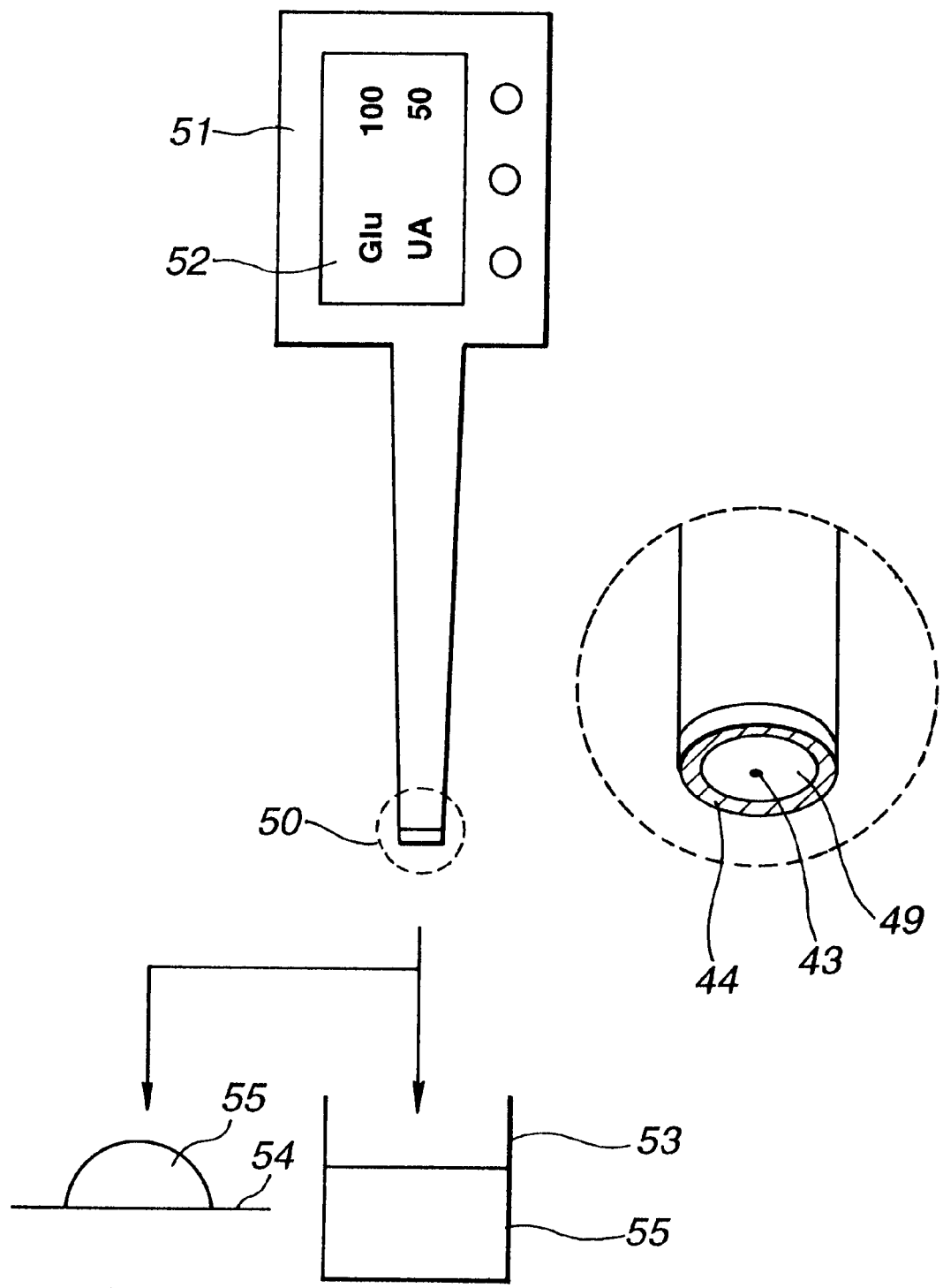
FIG. 20 diagrammatically shows an embodiment of the concentration sensor with a detection electrode of conductive diamond and a counter micro-electrode.

FIG. 20 shows another embodiment of the concentration sensor of the present invention. This is of a microelectrode type wherein a detection microelectrode consisting of conductive diamond is used. More particularly, this concentration sensor has a detection part 50 at the top, which is shown in an enlarged drawings in the broken circle in FIG. 20. The detection part 50 comprises a central detection microelectrode 43 consisting of conductive diamond, an annular counter electrode 44 such as platinum electrode having a surface area much greater than the detection electrode 43, and an electrically insulating layer 49 between the detection electrode 43 and the counter electrode.

At the opposite end of this microelectrode-type concentration sensor are mounted a power source (not shown) such as a battery etc. that energizes each electrode 43, 44 in the detection part 50, a control unit 51 that conducts arithmetic control based on measurement obtained at the detection electrode 43, and a display unit 52 that represents result of the control by the control unit 51.

With the microelectrode-type concentration sensor such as shown in FIG. 20, when the detection electrode 43 becomes operative in a stationary solution of an electrolyte 55 received in a vessel 53 or dropped on a sample plate 54, only an electric current based on three-dimensional diffusion of the target substances flows on the surface of the electrode 53, thereby providing high sensitivity and reproductivity of the sensor response.

The preceding concentration sensors are all constructed such that the electrodes are immersed in an electrolyte solution containing target substances for concentration measurement. FIGS. 21–25 show another type concentration sensors in which the reaction occuring between the electrode surface and the electrolyte solution surface is observed for concentration measurement. In other words, it is not necessary to immerse the electrode into the electrolyte. At lease one surface of the electrode is simply in contact with the electrolyte.

Figure 21:
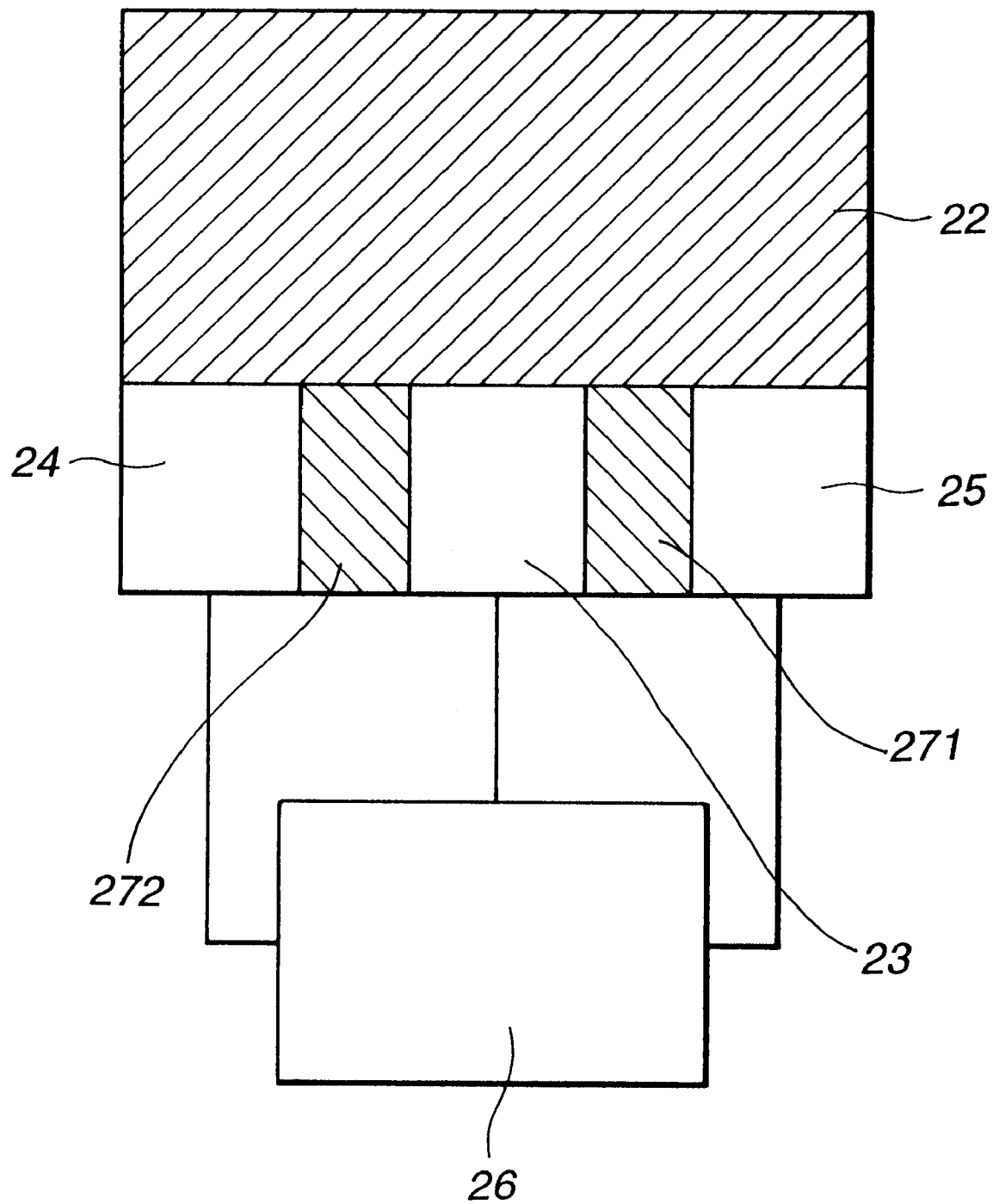
FIGS. 21–25 diagrammatically show respectivel embodiments of the concentration sensor with electrodes not immersed in an electrolyte but simply in contact therewith.

FIG. 21 shows an example of the contact type concentration sensor, wherein a reference electrode 25, a detection electrode 23 of conductive diamond and a counter electrode 24 are arranged linearly, spaced by electrically insulating layers 271 and 272. For measurement, an electrolyte 22 containing target substances is brought into contact with one face of the respective electrodes 23, 24, 25 to which is applied a predetermined potential from a voltage applicator 26.

Figure 22:
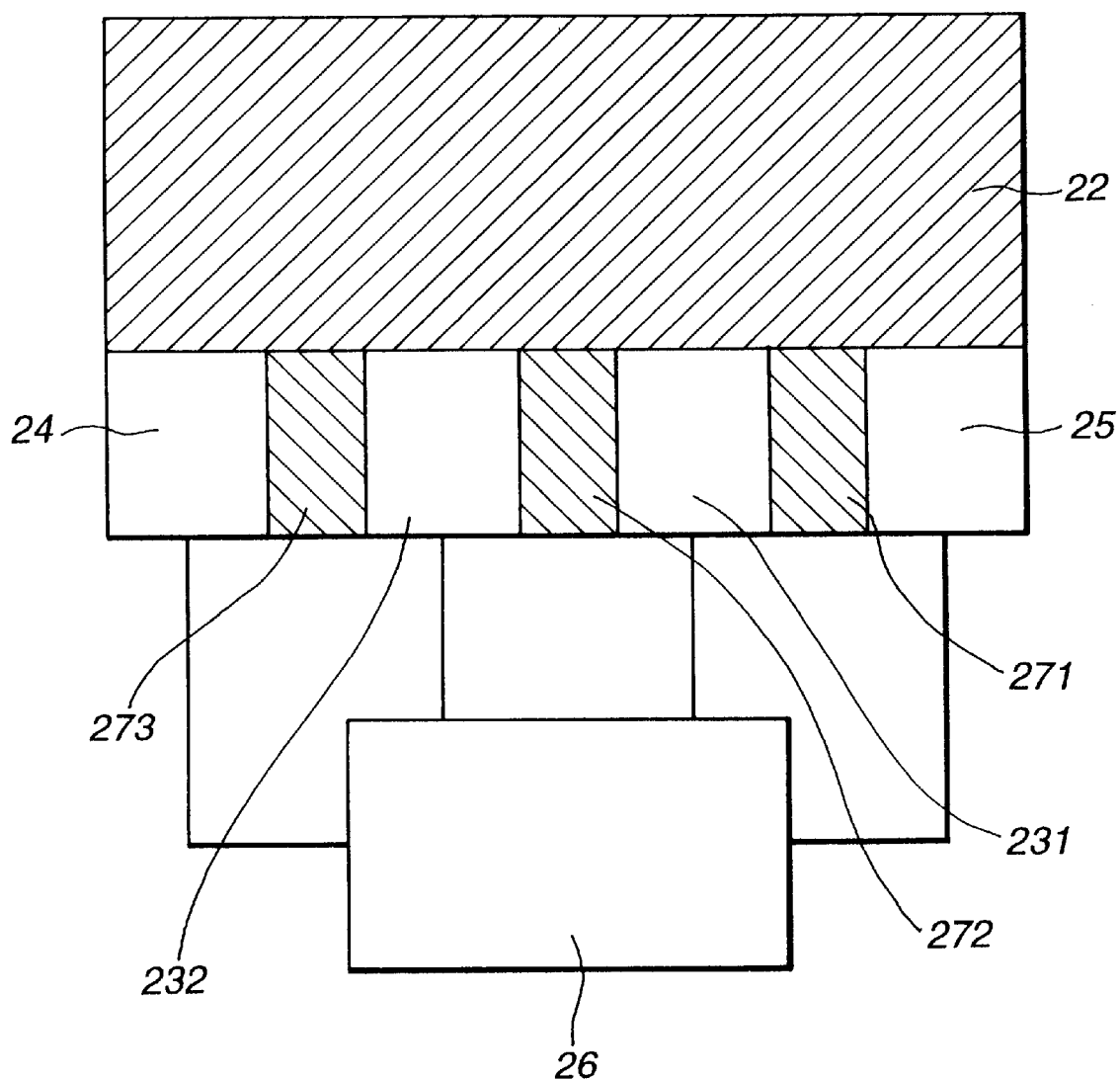

The concentration sensor of FIG. 21 may be modified as shown in FIG. 22. In the concentration sensor of FIG. 22, a single detection electrode used in FIG. 21 is replaced by two electrodes, one of which is a detection electrode 231 of conductive diamond and the other is a detection electrode 232 of materials other than conductive diamond. In accordance of increase of the number of the electrodes, an electrically insulating layers 273 is arranged in addition to the layers 271 and 272. Except the foregoing, this concentration sensor has the same arrangement as in the concentration sensor of FIG. 21.

Figure 23:
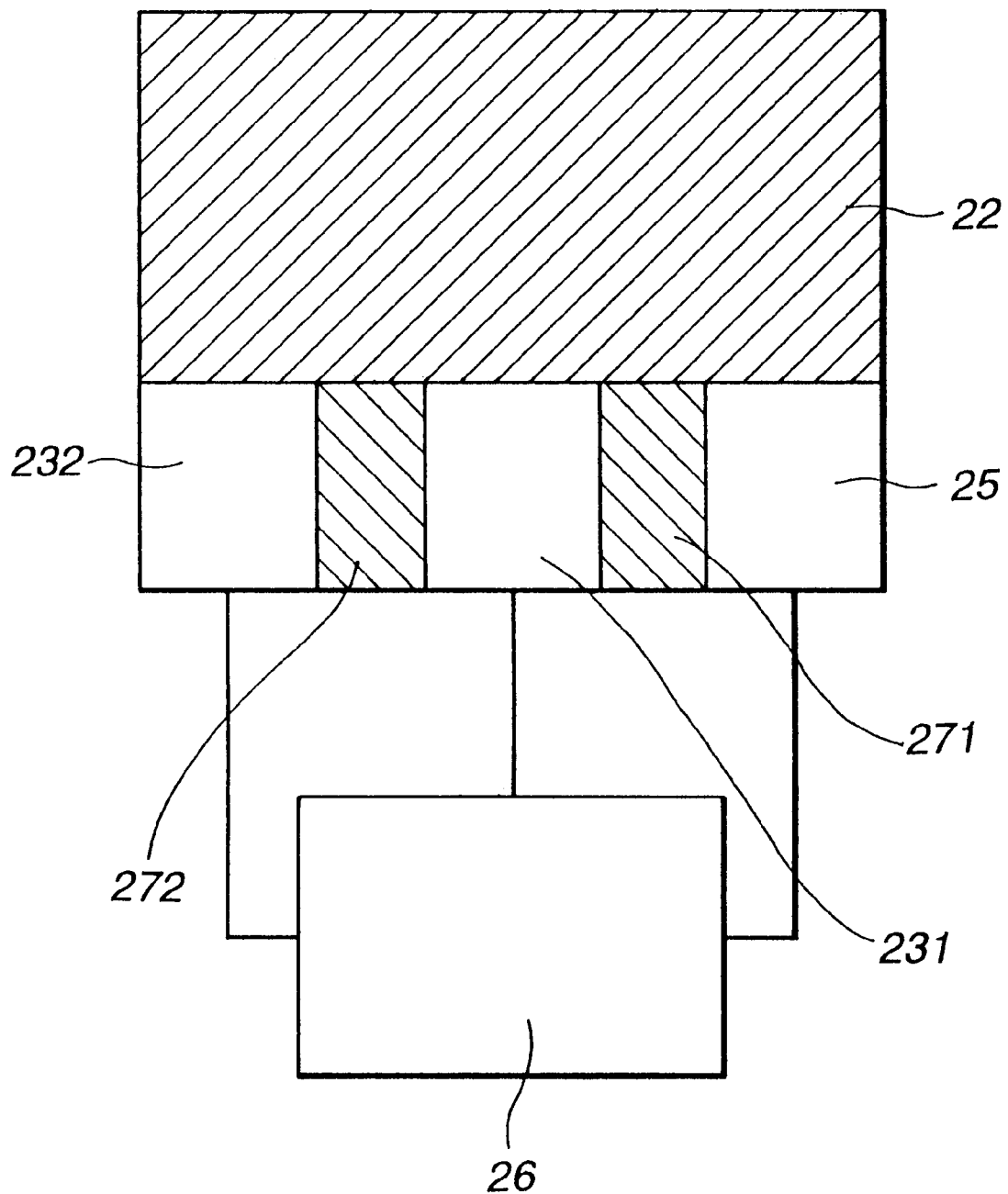

FIG. 23 shows still another example of the contact type concentration sensor, wherein, with the same electrode arrangement as in FIG. 21, an electrode 231 of conductive diamond and an electrode 232 of materials other than conductive diamond are arranged such that their signs are reversible to each other. That is, when one of the electrodes is used as a detection electrode, the other electrode acts as a counter electrode. Except the foregoing, this concentration sensor has the same arrangement as in FIG. 21.

Figure 24:
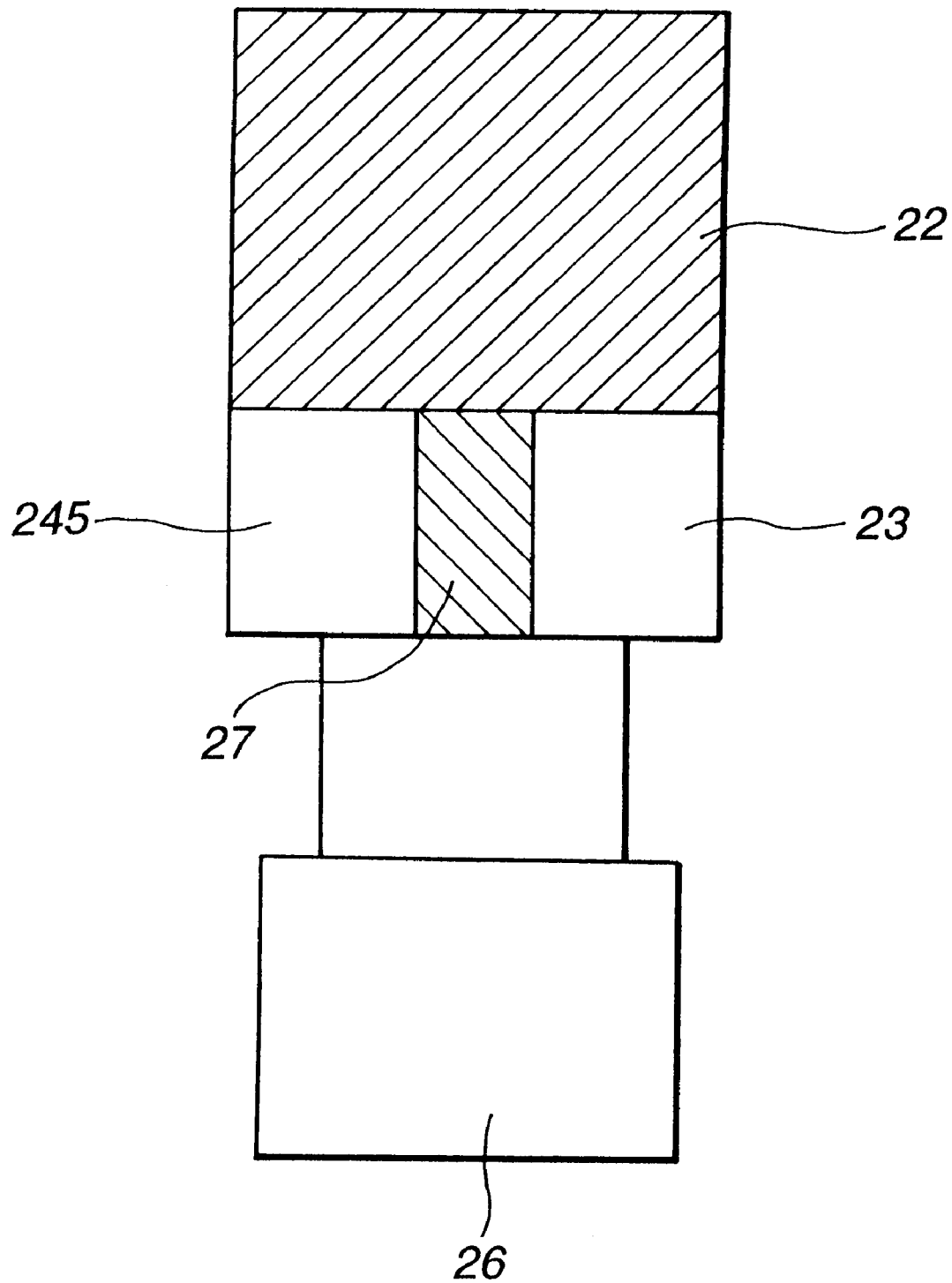

FIG. 24 shows still another example of the same type concentration sensor, which has only two electrodes, a detection electrode 23 of conductive electrode and a double-functional counter/reference electrode 245, separated by an electrically insulating layer 27. Providing such double-functional electrode will reduce the number of parts and simplify the circuit of the concentration sensor. Except the foregoing, this concentration sensor has the same arrangement as in FIG. 21.

Figure 25:
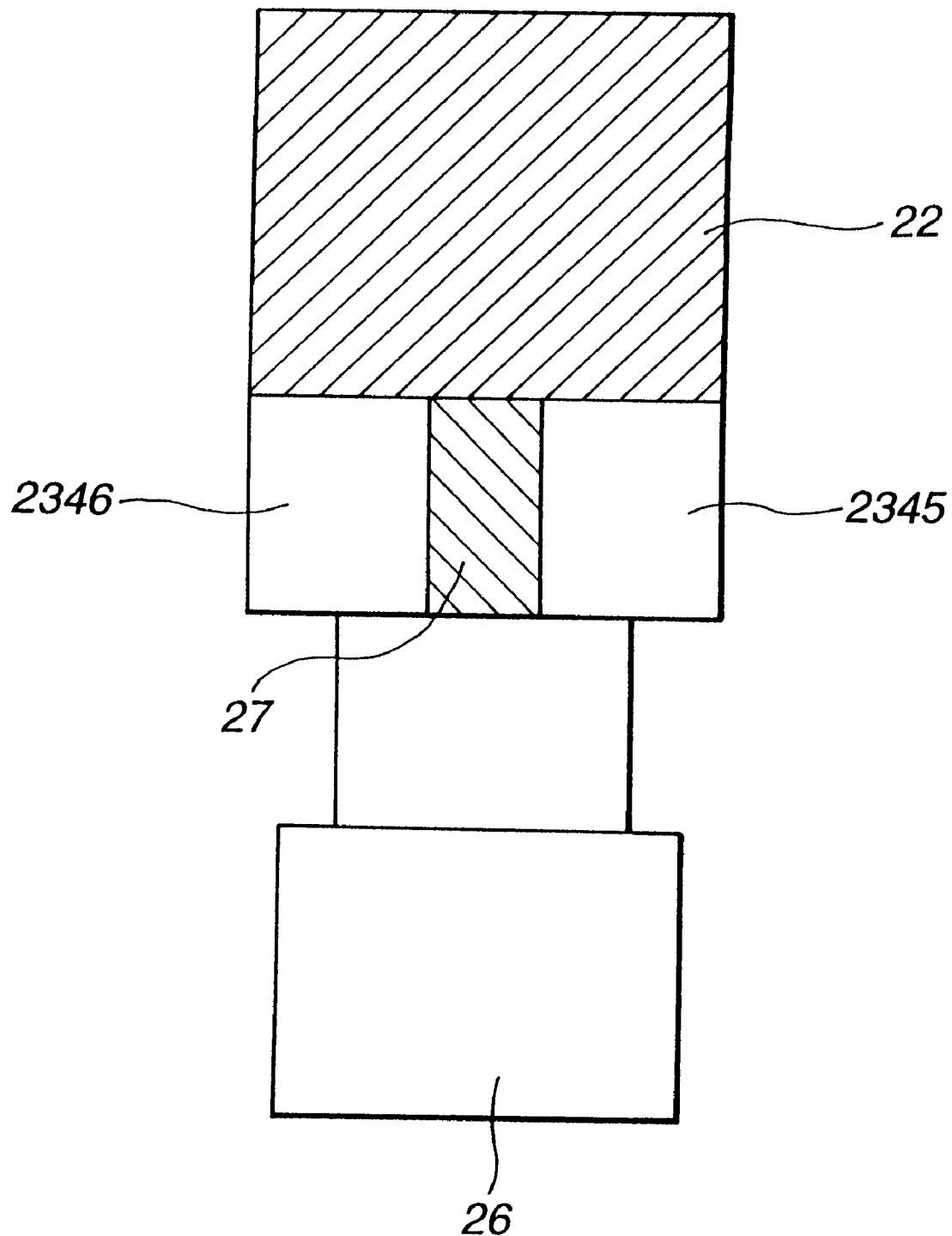

Yet another example of the same type concentration sensor shown in FIG. 25 has the same arrangement as in FIG. 21 exept that it employs a multi-functional detection// counter/reference electrode 2345 of conductive electrode and another multi-functional detection/counter/reference electrode 2346 of materials other than conductive diamond. Providing such multi-functional electrodes will, of course, greatly reduce the number of parts and simplify the circuit of the concentration sensor.

Preparation of Diamond Electrode

The substrate of the diamond electrode used for concentration measurement according to the present invention includes oxides, nitrides and carbides of metal such, as silicon, manganese, vanadium, thallium, aluminum, titanium, tungsten, molybdenum, germanium and chromium. Various cermets such as $Al_2O_3$—Fe based, TiC—Ni based, TiC—Co based and $B_4C$—Fe based cermets, as well as various ceramics can also be used as the substrate of the diamond electrode.

Impurities are necessary to impart electrical conductivity to diamond. For example, the group IIIb elements in the periodic table such as B, Al, Ca, In, Tl and the group Vb elements in the periodic table such as N, P, Sb, Bi may be favorably incorporated into diamond. B is considered as the most favorable one.

A diamond thin film electrode for use in the electrode of the concentration sensor of the present invention may be produced by any conventional production process. For example, it may be produced by the following microwave plasma CVD method.

The substrate such as n-type silicon single crystal (100) is arranged in a reaction chamber into which a predetermined amount of hydrogen is introduced as a carrier gas. Before reaching the reaction chamber, the carrier gas passes through a solution of acetone/methanol (9:1) mixture in which boron oxide is dissolved, so that the carrier gas contains carbon and boron. The acetone/methanol serves as a carbon source for diamond, and boron oxide serves as a boron source to be contained in diamond as impurities. In this state, microwaves are given under predetermined conditions to cause plasma discharge, whereby carbon radicals generate from the carbon source in the carrier gas and accumulate on the substrate while maintaining the sp3 structure, thereby forming a thin film of diamond.

The thickness of the diamond film depends on the film-forming period. By way of example, when 5 kW microwave is given for about 10 hours, diamond with a film of dozens micrometers in thickness and several centimeters at the maximum in one side can be formed. Further, by changing the ratio of boron atoms to carbon atoms in a mixed solution, the amount of boron incorporated into the diamond film can be controlled. There is correlation between the amount of incorporated boron and diamond resistance. As the amount of incorporated boron is increased, the resulting diamond has decreased resistance and therefore improved electrical conductivity. For example, when the ratio of boron atoms to carbon atoms is set at about 1%, a diamond film will be given a specific resistance of about 0.001 to 0.01Ωcm.

In accordance with another production method, the substrate is dissolved in a solution such as acid etc. to remove a diamond film. A suitable lead wire connected to the diamond film, by means of a silver paste etc., to produce a diamond electrode for use in the present invention.

Preparation of Electrode of Material other than Diamond

The electrode of material other than conductive diamond may be used in the concentration sensor of the present invention. Such material may be classified into the group consisting of single metals or alloys; the group consisting of metal oxides; the group consisting of the semiconductors; the group consisting of carbon-based materials; and the group consisting of metal sulfides.

The group consisting of single metals or alloys includes single metals such as Ti, V, Fe, Co, Ni, Cu, Zn, Ge, Nb, Ru, Rh, Pd, Ag, Cd, Sn, Ta, W, Os, Ir, Pt, Au, Hg and Pb and alloys of any combinations thereof.

The group consisting of metal oxides includes $TiO_2$, $MnO_2$, $PbO_2$, $WO_3$, perobuskite (phonetic) oxides, bronze oxides, spinel oxides and pyrochlor oxides.

The group consisting of semiconductors includes Si, Ge, ZnO, CdS, $TiO_2$ and GaAs.

The group consisting of carbon-based materials includes graphite, carbon paste, glassy carbon and HOPG (high-orientation pyrolysis graphite).

The group consisting of metal sulfites includes $RuS_2$, PdS, $PdS_2$, CdS, $In_2S_3$, $OsS_2$, $CoS_2$, PbS, $NiS_2$ and $MoS_2$.

When the electrode made of material other than diamond is used in the concentration sensor of the present invention, the surface thereof may be covered with a single layer or plural layers of single metal, alloy, inorganic compound, organic compound, polymeric compound, living body-related substances, etc, by any suitable physical process such as electrolysis plating, non-electrolysis plating, electric deposition, spattering, etc., or chemical process such as adsorption, covalent bonding, etc.

Materials of the reference electrode is not limited insofar as it stabilizes electric potential. For example, a reversible hydrogen electrode, an electrode of silver and silver chloride, a saturated calomel electrode, etc. may preferably be used as materials of the reference electrode. The counter electrode is usually made of anti-corrosive materials such as platinum, glassy carbon, diamond etc.

Measurement of Electric Current-Electric Potential Curves

The diamond electrode prepared by the above-mentioned process is used as a detection electrode to obtain its inherent current-potential curves by experiments in various reaction systems in accordance with the electric potential sweep method. For comparison, the platinum electrode is used as a detection electrode to obtain its inherent current-potential curves. Specifically, with the concentration sensor of FIG. 13 in which an electrolyte 2 consisting of a phosphate buffer (pH 7.0) containing the target substances, the electric potential of diamond toward the reference electrode is contro such that it is swept at a rate of 50 mV/sec. to monitor the response electric current, whereby the current-potential curve can be obtained. FIGS. 33–44 show the current-potential curves which have been obtained in the foregoing manner under different conditions.

Figure 33:
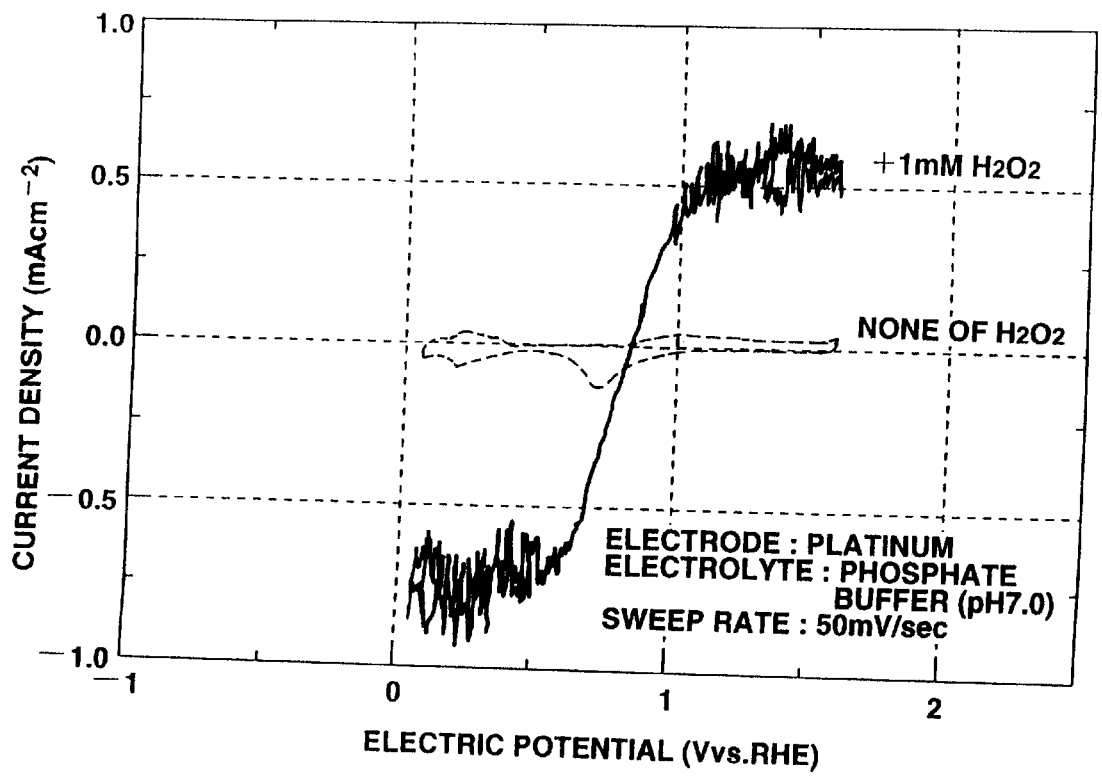
FIG. 33 is a current-potential graph showing relationship between an electric current on a platinum detection electrode and potential regarding an electrolyte containing +1 mM $H_2O_2$ and another electrolyte not containing $H_2O_2$.

FIG. 33 shows graphs showing the relationship between the electric current density and the electric potential where an electrolyte contains +1 mM $H_2O_2$ and where an electrolyte does not contain $H_2O_2$, with the platinum detection electrode.

Figure 34:
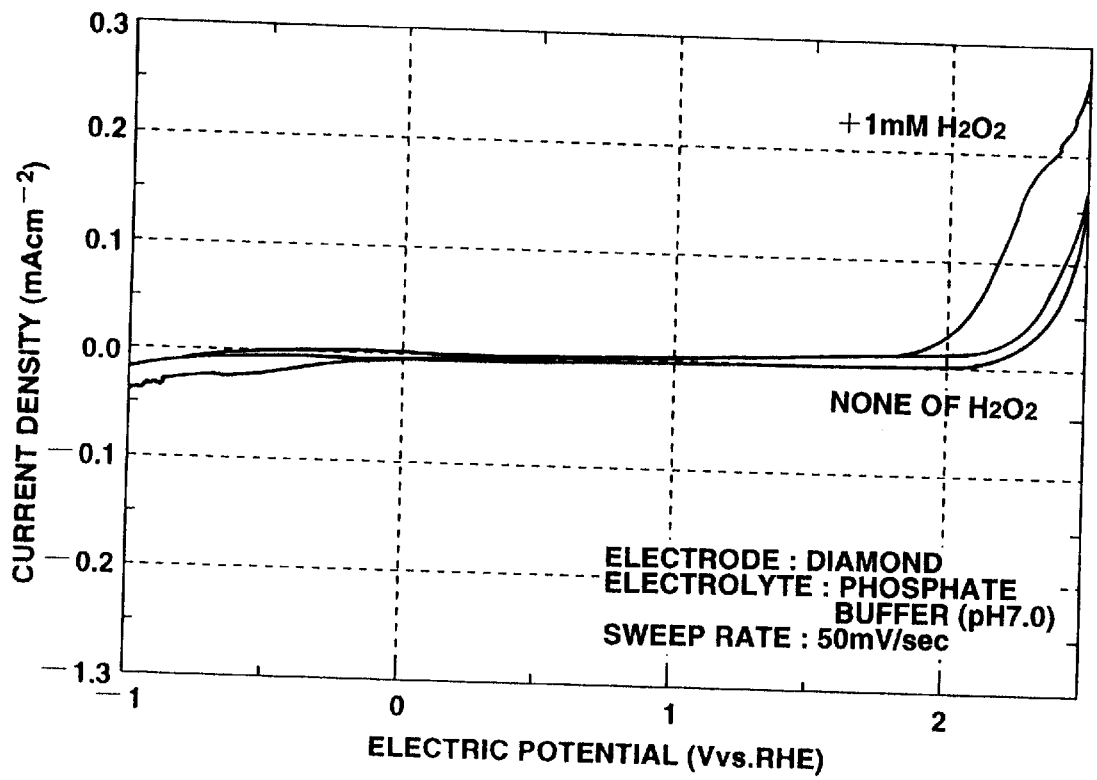
FIG. 34 is a current-potential graph showing relationship between an electric current on a diamond detection electrode and potential regarding an electrolyte containing +1 mM $H_2O_2$ and another electrolyte not containing $H_2O_2$.

FIG. 34 shows graphs showing the relationshionship between the electric current density and the electric potential where an electrolyte contains +1 mM $H_2O_2$ and where an electrolyte does not contain $H_2O_2$, with the conductive diamond detection electrode.

Figure 35:
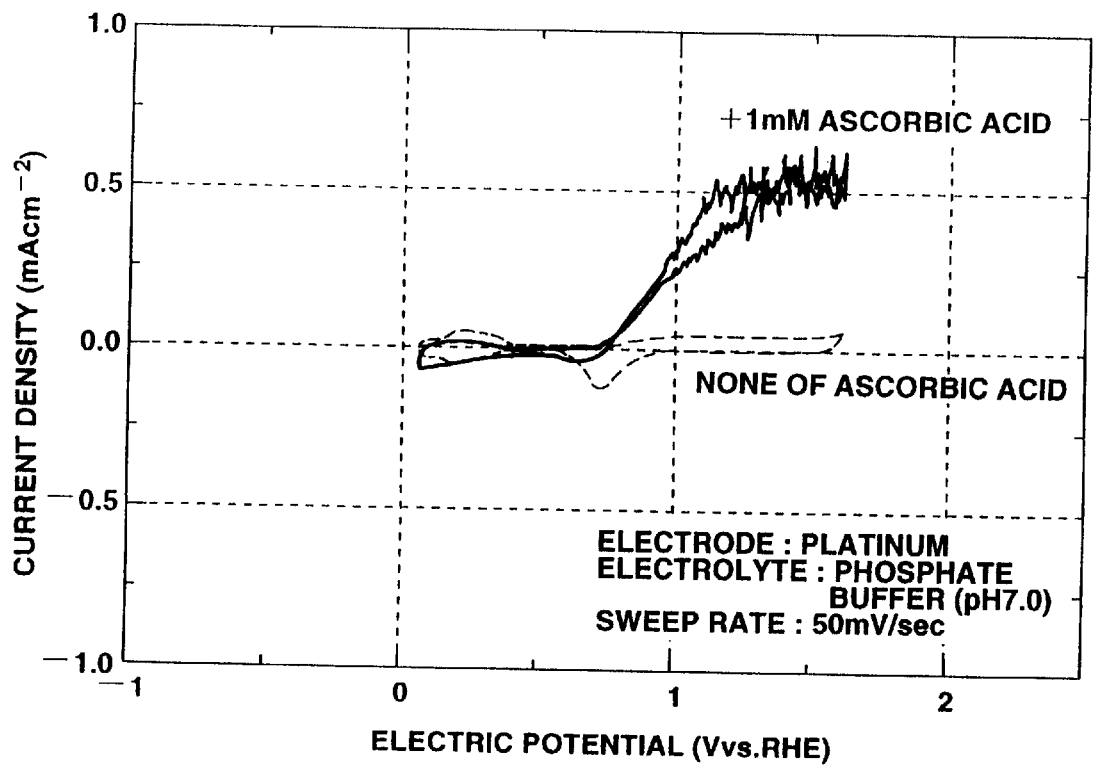
FIG. 35 is a current-potential graph showing relationship between an electric current on a platinum detection electrode and potential regarding an electrolyte containing +1 mM ascorbic acid and another electrolyte not containing ascorbic acid.

FIG. 35 shows graphs showing the relationship between the electric current density and the electric potential where an electrolyte contains +1 mM ascorbic acid and where an electrolyte does not contain ascorbic acid, with the platinum detection electrode.

Figure 36:
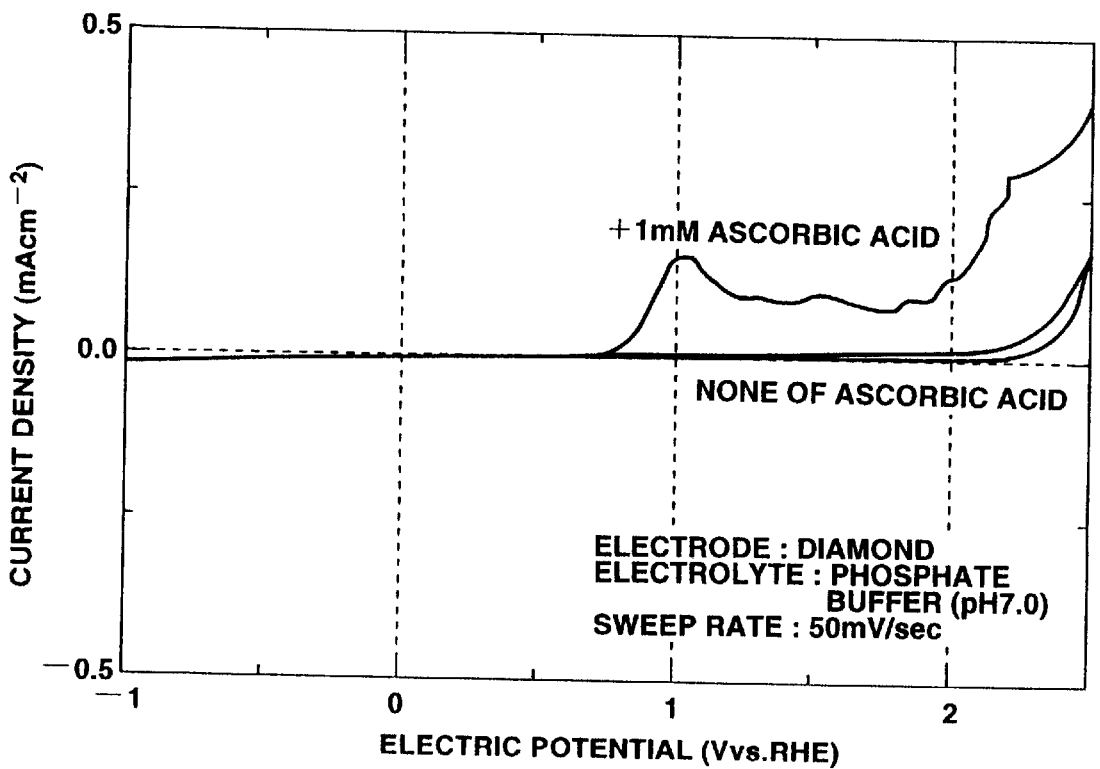
FIG. 36 is a current-potential graph showing relationship between an electric current on a diamond detection electrode and potential regarding an electrolyte containing +1 mM ascorbid acid and another electrolyte not containing ascorbic acid.

FIG. 36 shows graphs showing the relationship between the electric current density and the electric potential where an electrolyte contains +1 mM ascorbic acid and where an electrolyte does not contain ascorbic acid, with the conductive diamond detection electrode.

Figure 37:
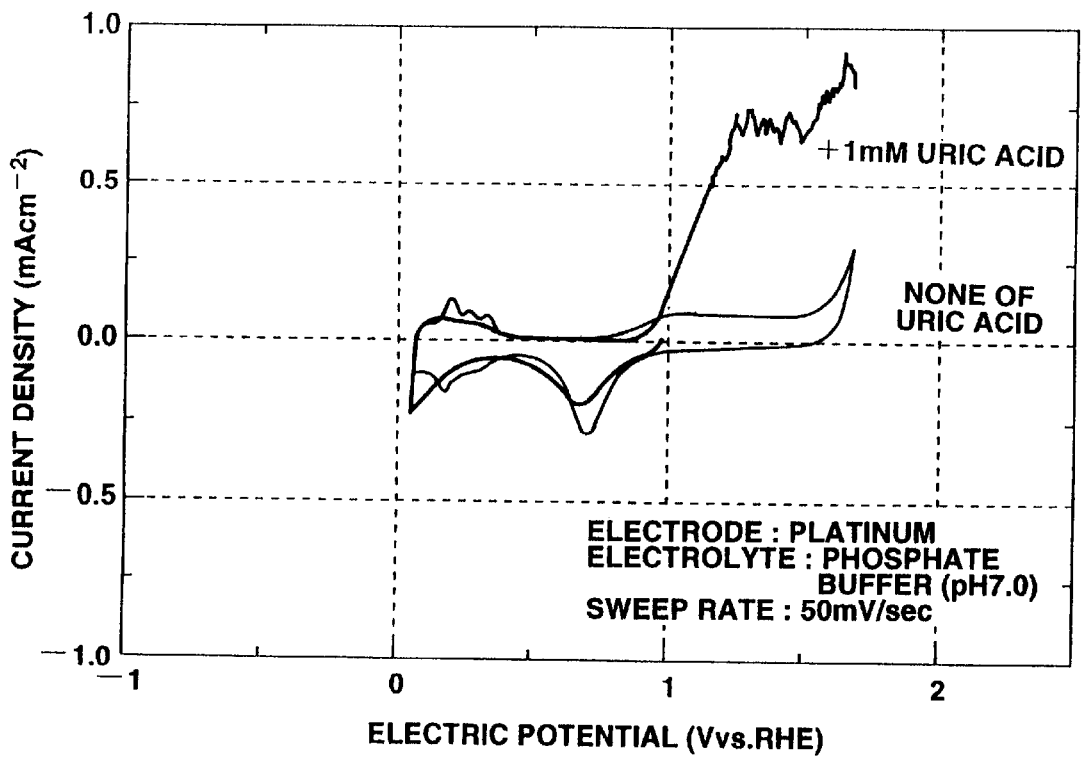
FIG. 37 is a current-potential graph showing relationship between an electric current on a platinum detection electrode and potential regarding an electrolyte containing +1 mM uric acid and another electrolyte not containing uric acid.

FIG. 37 shows graphs showing the relationship between the electric current density and the electric potential where an electrolyte contains +1 mM uric acid and where an electrolyte does not contain uric acid, with the platinum detection electrode.

Figure 38:
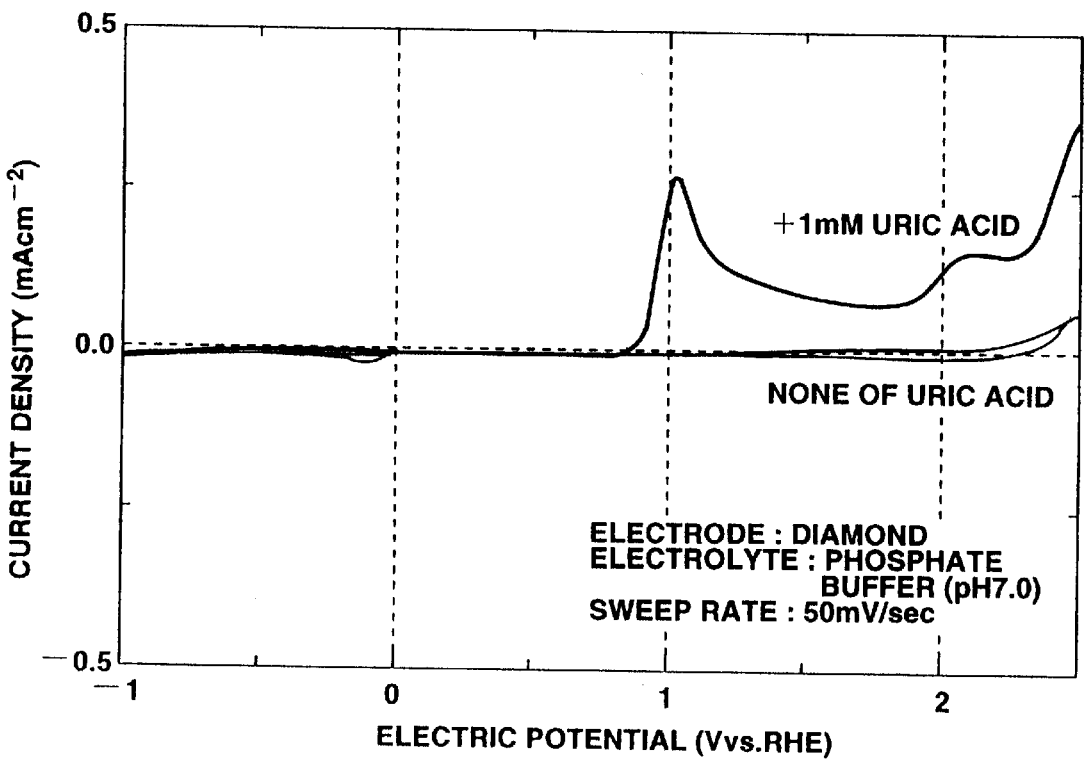
FIG. 38 is a current-potential graph showing relationship between an electric current on a diamond detection electrode and potential regarding an electrolyte containing +1 mM uric acid and another electrolyte not containing uric acid.

FIG. 38 shows graphs showing the relationshionship between the electric current density and the electric potential where an electrolyte contains +1 mM uric acid and where an electrolyte does not contain uric acid, with the conductive diamond detection electrode.

Figure 39:
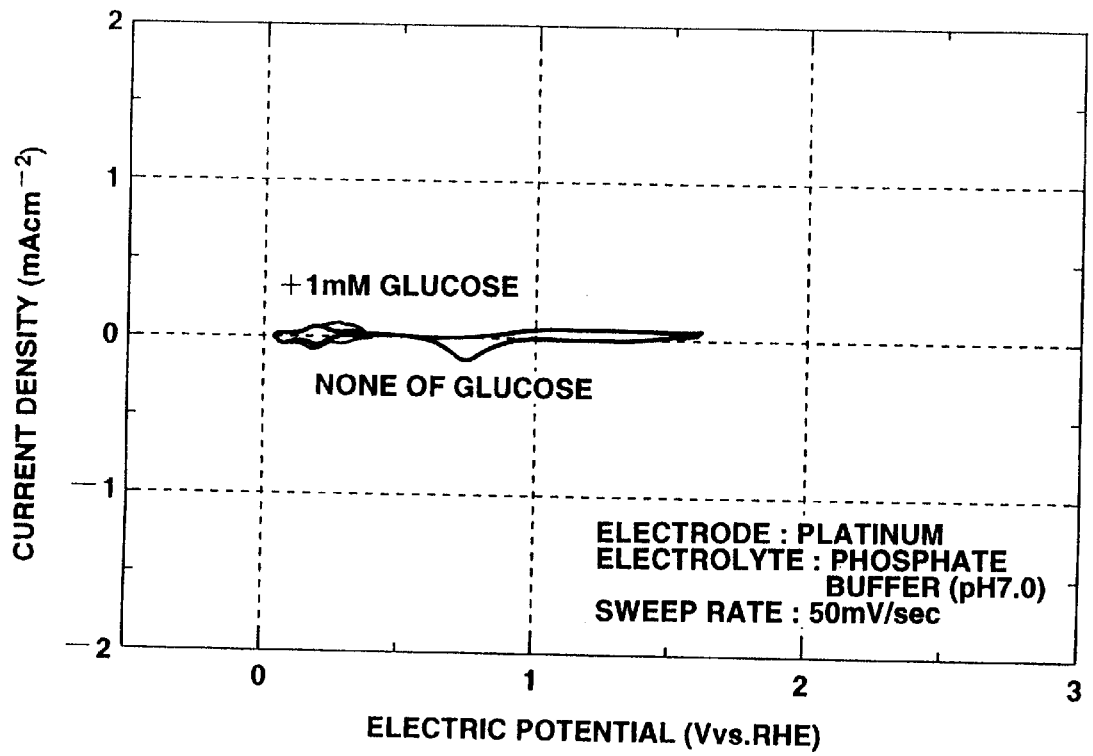
FIG. 39 is a current-potential graph showing relationship between an electric current on a platinum detection electrode and potential regarding an electrolyte containing +1 mM glucose and another electrolyte not containing glucose.

FIG. 39 shows graphs showing the relationship between the electric current density and the electric potential where an electrolyte contains +1 mM glucose and where an electrolyte does not contain glucose, with the platinum detection electrode.

Figure 40:
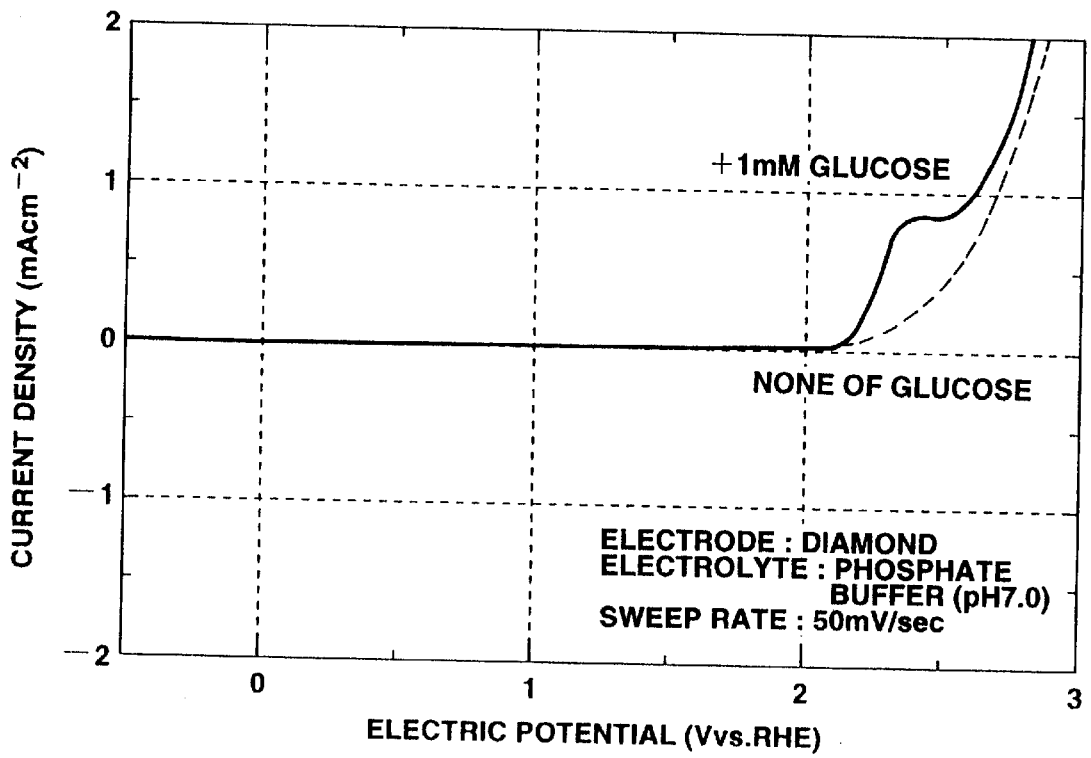
FIG. 40 is a current-potential graph showing relationship between an electric current on a diamond detection electrode and potential regarding an electrolyte containing +1 mM glucose and another electrolyte not containing glucose.

FIG. 40 shows graphs showing the relationshionship between the electric current density and the electric potential where an electrolyte contains +1 mM glucose and where an electrolyte does not contain glucose, with the conductive diamond detection electrode.

Figure 41:
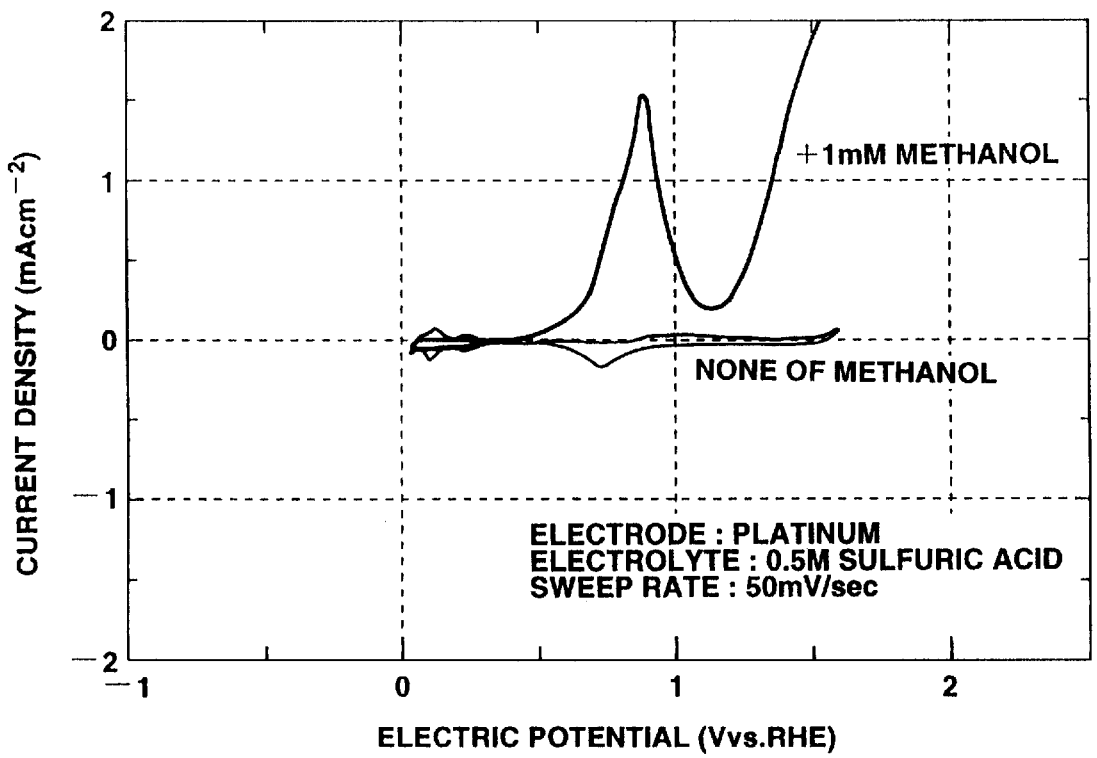
FIG. 41 is a current-potential graph showing relationship between an electric current on a platinum detection electrode and potential regarding an electrolyte containing +1 mM methanol and another electrolyte not containing methanol.

FIG. 41 shows graphs showing the relationship between the electric current density and the electric potential where an electrolyte contains +1 mM methanol and where an electrolyte does not contain methanol, with the platinum detection electrode.

Figure 42:
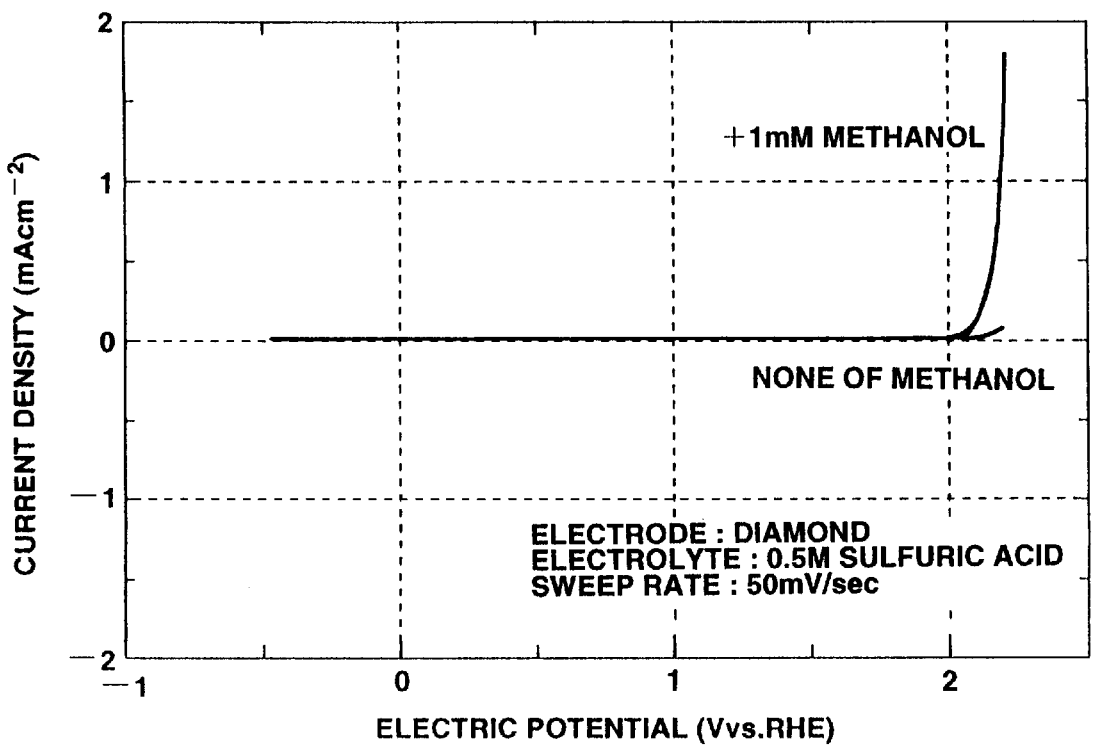
FIG. 42 is a current-potential graph showing relationship between an electric current on a diamond detection electrode and potential regarding an electrolyte containing +1 mM methanol and another electrolyte not containing methanol.

FIG. 42 shows graphs showing the relationshionship between the electric current density and the electric potential where an electrolyte contains +1 mM methanol and where an electrolyte does not contain methanol, with the conductive diamond detection electrode.

Figure 43:
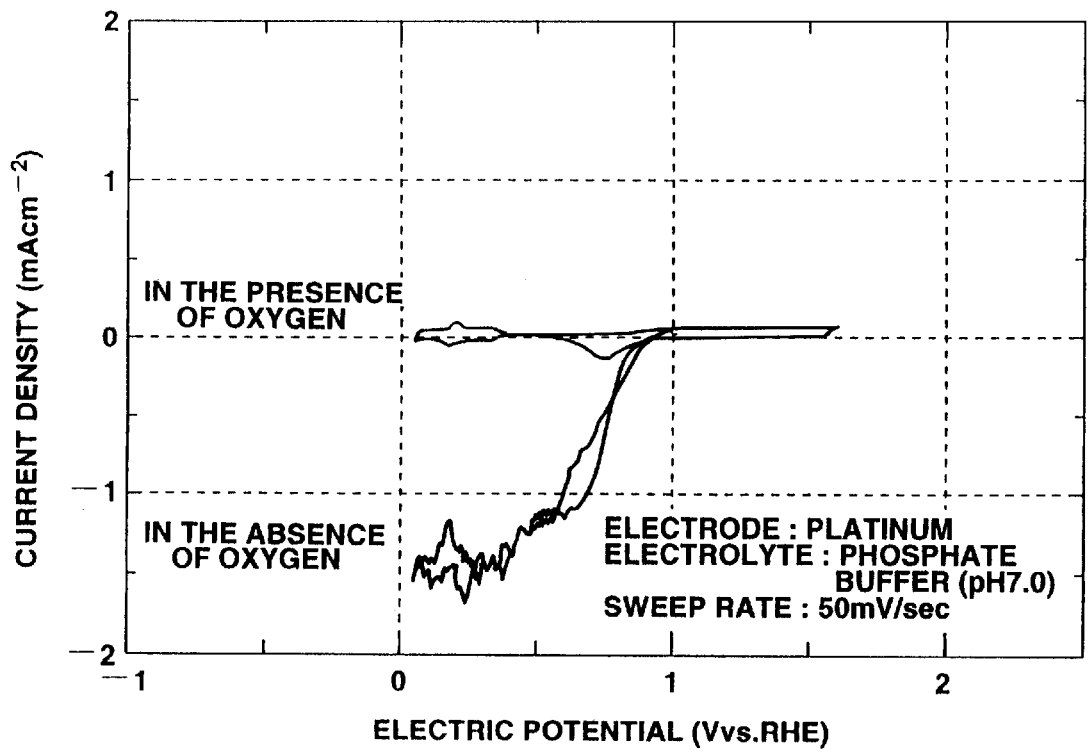
FIG. 43 is a current-potential graph showing relationship between an electric current on a platinum detection electrode and potential regarding an electrolyte containing oxygen and another electrolyte not containing oxygen.

FIG. 43 shows graphs showing the relationship between the electric current density and the electric potential where an electrolyte contains oxygen and where an electrolyte contains no oxygen, with the platinum detection electrode.

Figure 44:
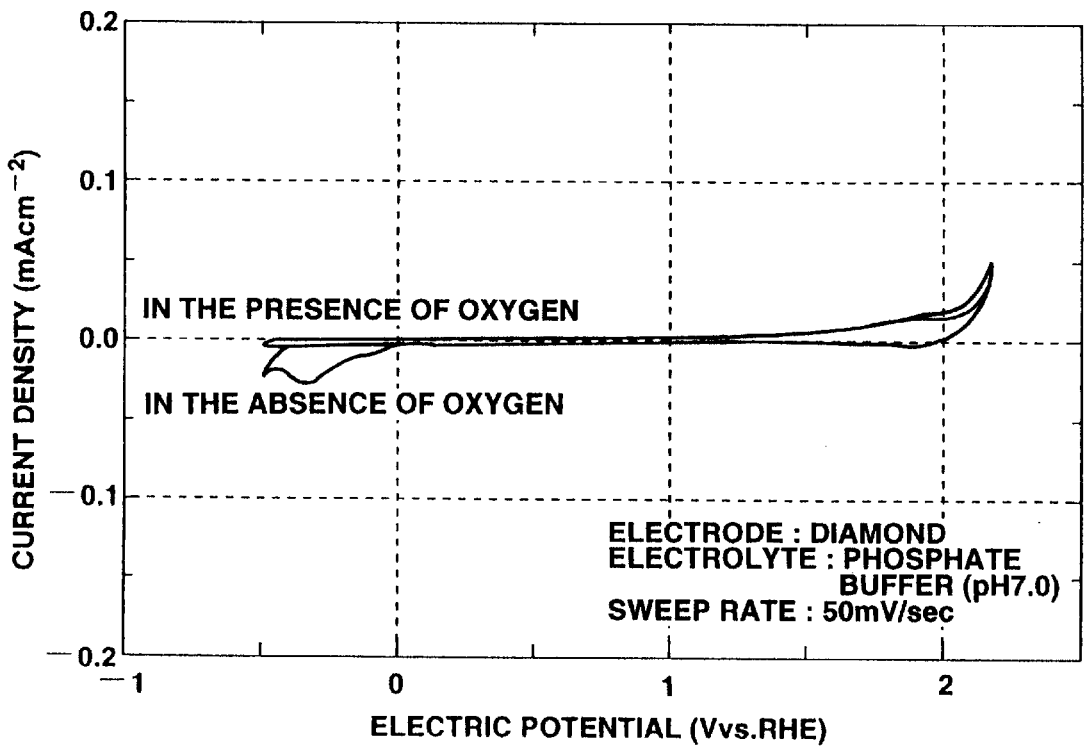
FIG. 44 is a current-potential graph showing relationship between an electric current on a diamond detection electrode and potential regarding an electrolyte containing oxygen and another electrolyte not containing oxygen.

FIG. 44 shows graphs showing the relationship between the electric current density and the electric potential where an electrolyte contains oxygenl and where an electrolyte contains no oxygen, with the conductive diamond detection electrode.

In all the results in graphs shown in FIGS. 33–44, not the electric current value but the electric current density is measured in order to avoid the influence of electrode size difference.

The current-potential curve may be obtained by using another type concentration sensor employing a rotational disk electrode such as shown in FIG. 19, some examples of which are shown in FIGS. 47–53. These examples are obtained with the concentration sensor of FIG. 19 using the rotating disc diamond detection electrode immersed in the phosphate buffer electrolyte (pH 7.0) containing the target substances. In the examples of FIGS. 47–51, the rotating disc electrode is rotated at 2000 rpm, whereas in the examples of FIGS. 52–53 at 1000 rpm.

Figure 47:
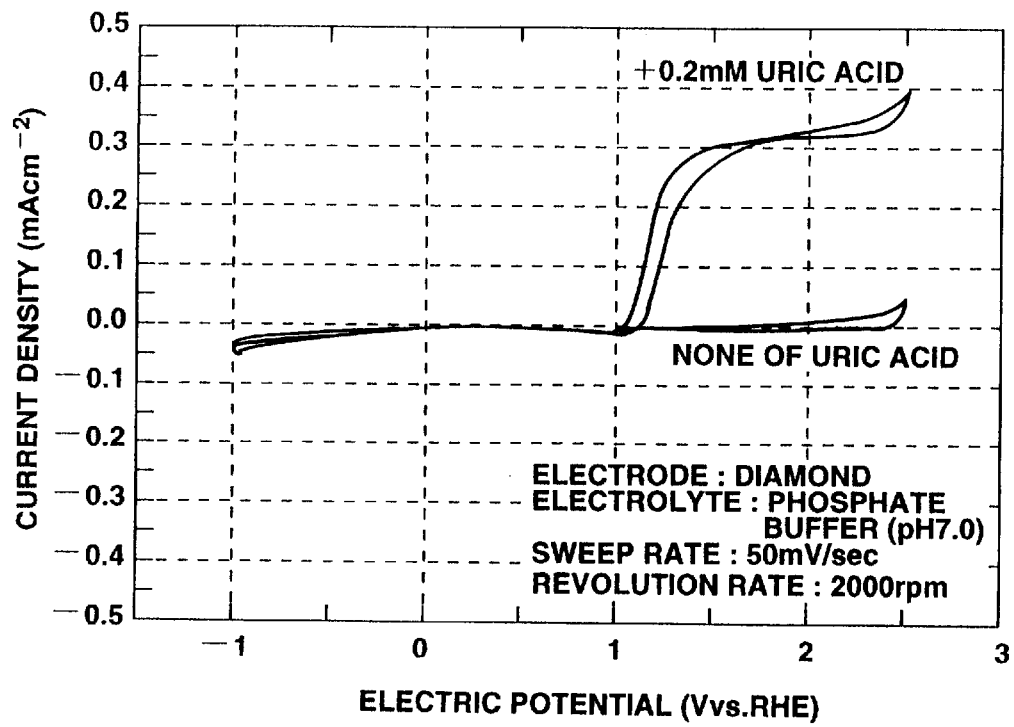
FIG. 47 shows relationship between electric current density and electric potential regarding an electrolyte containing +0.2 mM uric acid and another electrolyte not containing uric acid.

FIG. 47 shows graphs showing the relationship between the electric current density and the electric potential where the electrolyte contains +0.2 mM uric acid and where the electrolyte does not contain uric acid.

Figure 48:
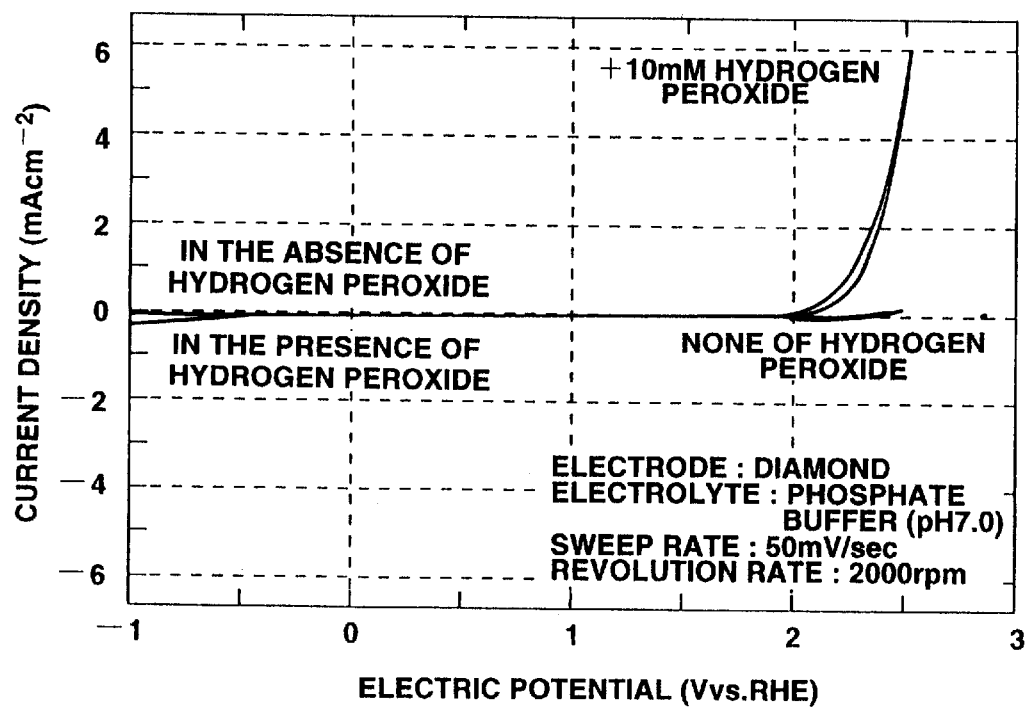
FIG. 48 shows relationship between electric current density and electric potential regarding an electrolyte containing +10 mM hydrogen peroxide and another electrolyte not containining hydrogen peroxide.

FIG. 48 shows graphs showing the relationship between the electric current density and the electric potential where the electrolyte contains +10 mM hydrogen peroxide and where the electrolyte does not contain hydrogen peroxide.

Figure 49:
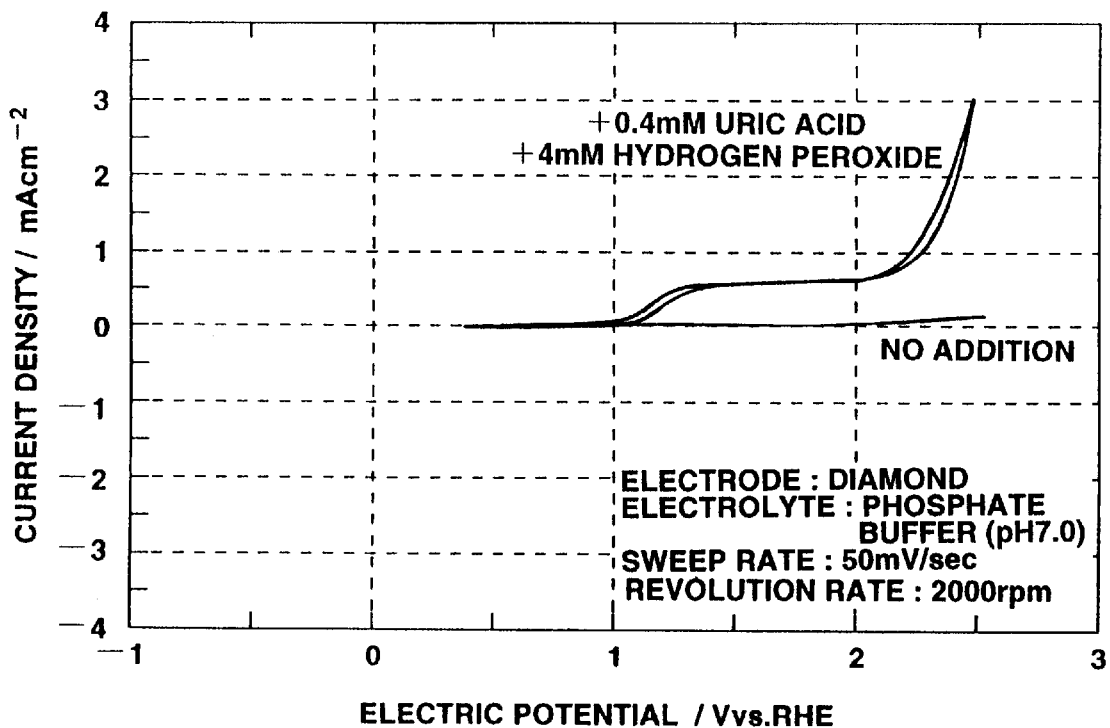
FIG. 49 shows relationship between electric current density and electric potential regarding an electrolyte containing +0.4 mM uric acid and +4 mM hydrogen peroxide and another electrolyte not containing uric acid and hydrogen peroxide.

FIG. 49 shows graphs showing the relationship between the electric current density and the electric potential where the electrolyte contains +0.4 mM uric acid and +4 mM hydrogen peroxide and where the electrolyte does not contain uric acid and hydrogen peroxide.

Figure 50:
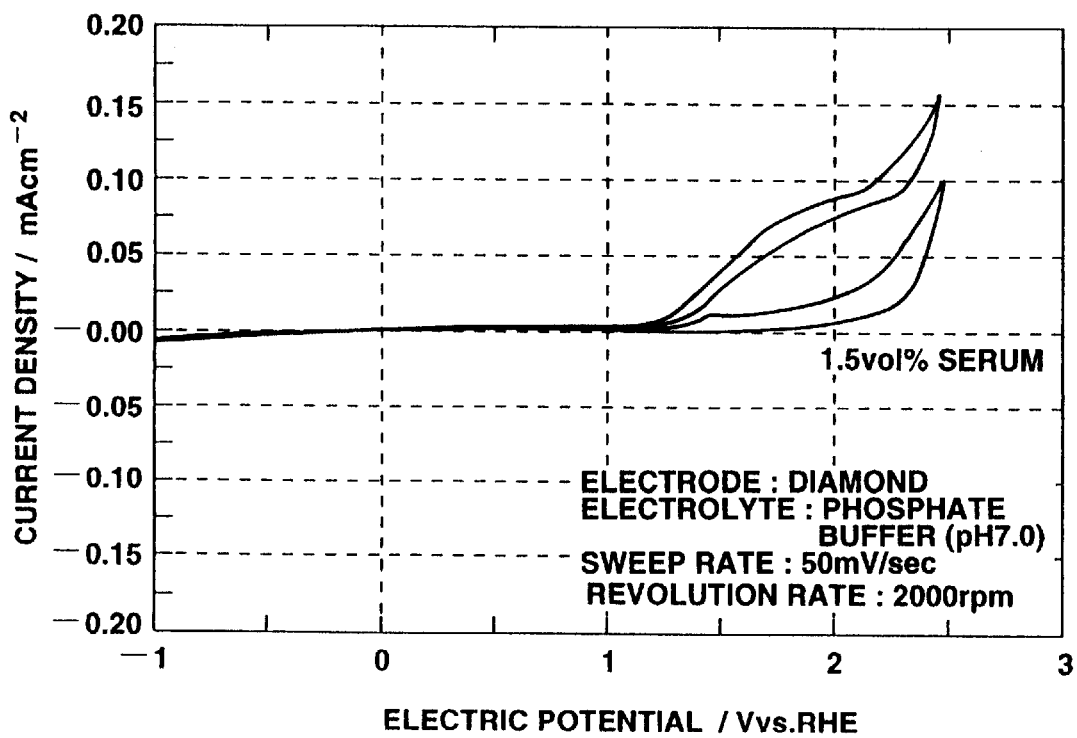
FIG. 50 shows relationship between electric current density and electric potential regarding an electrolyte containing 1.5 vol. % bovine serum and another electrolyte containing +0.08 mM uric acid in addition to 1.5 vol. % bovine serum.

FIG. 50 shows graphs showing the relationship between the electric current density and the electric potential where the electrolyte contains 1.5 vol. % bovine serum and where the electrolyte contains +0.08 mM uric acid in addition to 1.5 vol. % bovine serum.

Figure 51:
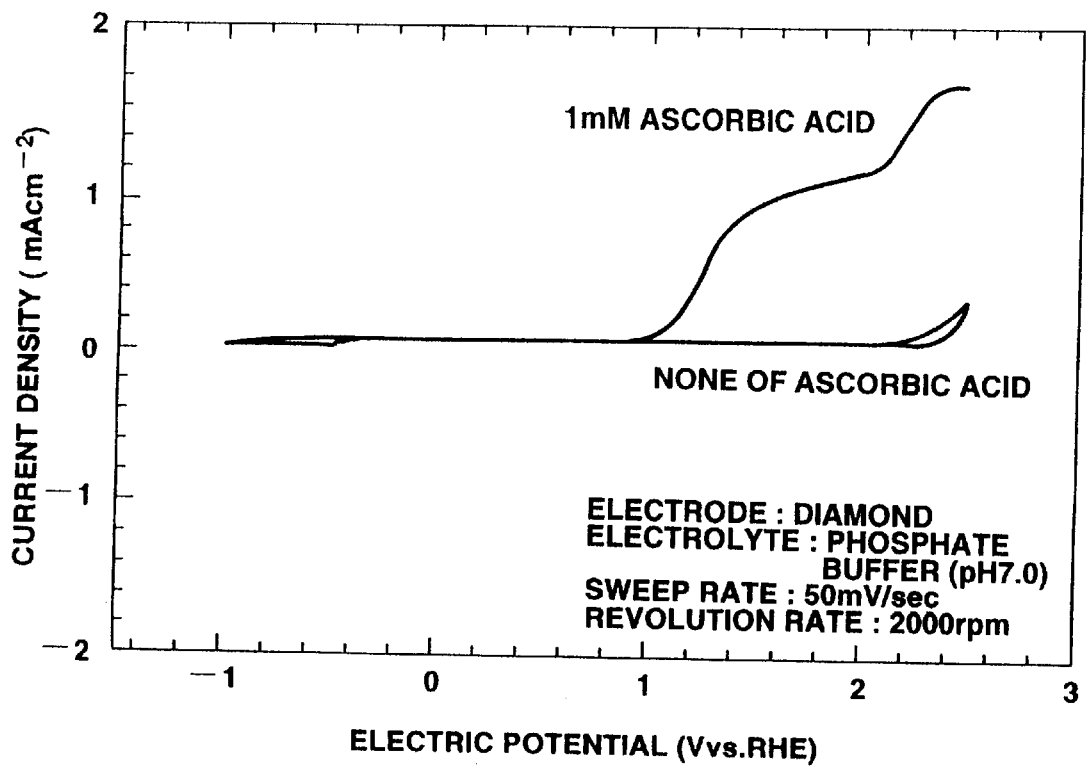
FIG. 51 shows relationship between electric current density and electric potential regarding an electrolyte containing +1 mM ascorbic acid and another electrolyte not containing ascorbic acid.

FIG. 51 shows graphs showing the relationship between the electric current density and the electric potential where the electrolyte contains +1 mM ascorbic acid and where the electrolyte does not contain ascorbic acid.

Figure 52:
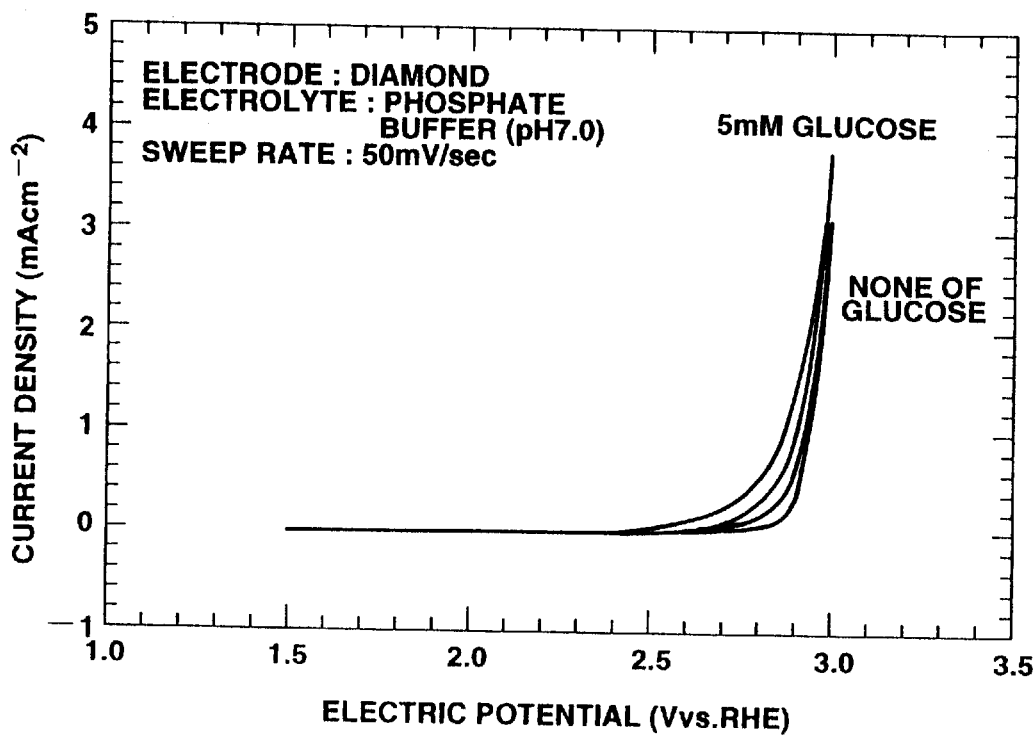
FIG. 52 shows relationship between electric current density and electric potential regarding an electrolyte containing +5 mM glucose and another electrolyte not containing glucose.

FIG. 52 shows graphs showing the relationship between the electric current density and the electric potential where the electrolyte contains +5 mM glucose and where the electrolyte does not contain glucose.

Figure 53:
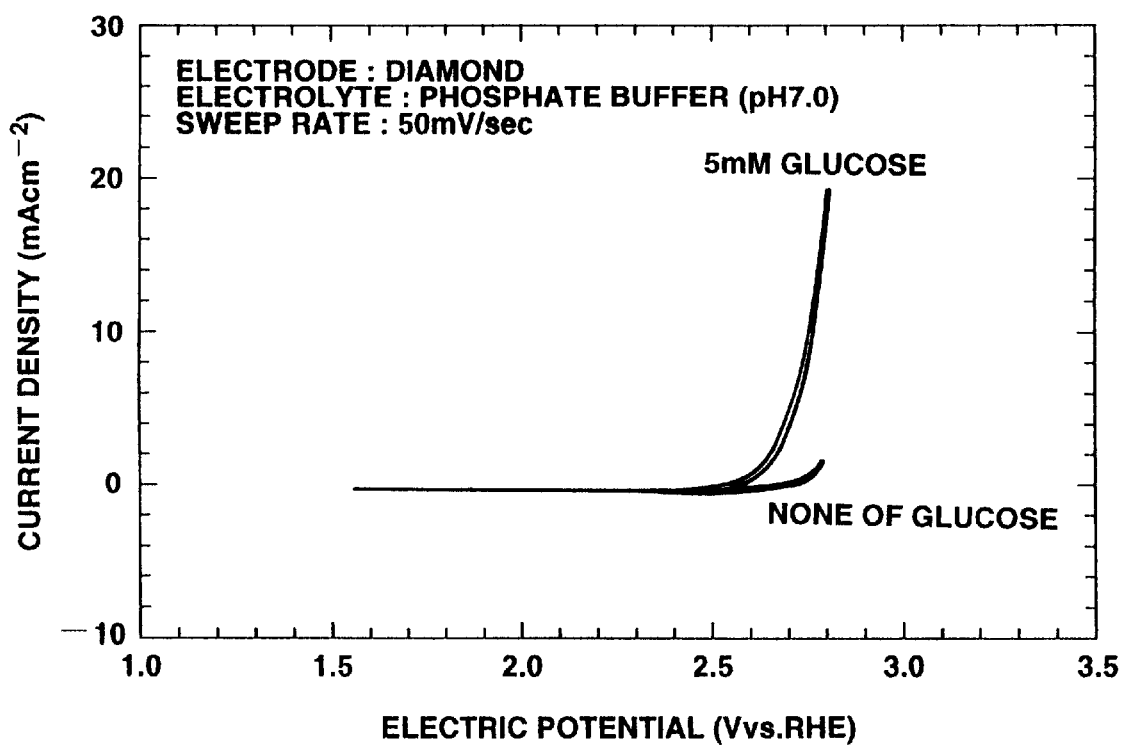
FIG. 53 shows relationship between electric current density and electric potential regarding an electrolyte containing +0.5M sulfuric and another electrolyte containing +0.5M sulfuric acid and +5 mM glucose.

FIG. 53 shows graphs showing the relationship between the electric current density and the electric potential where the electrolyte contains +0.5M sulfuric and where the electrolyte contains +0.5M sulfuric acid and +5 mM glucose.

Determination of Current-Concentration Relationship for Various Target Substances The relationship between each substance concentration and its response electric current at predetermined potential values is determined from the current-potential curves which have been prepared in the foregoing manner. The relational lines may be obtained at any potential values at which the target substance reacts. In a preferred embodiment, a potential value is selected to be within the region where diffusion of the target substance onto the surface of the electrode is not greatly changed so that the response electric current would be almost constant. This improves measurement accuracy. The potential value at which the relational line is prepared should be finally determined in further consideration of the effect of coexisting substances.

Figure 29:
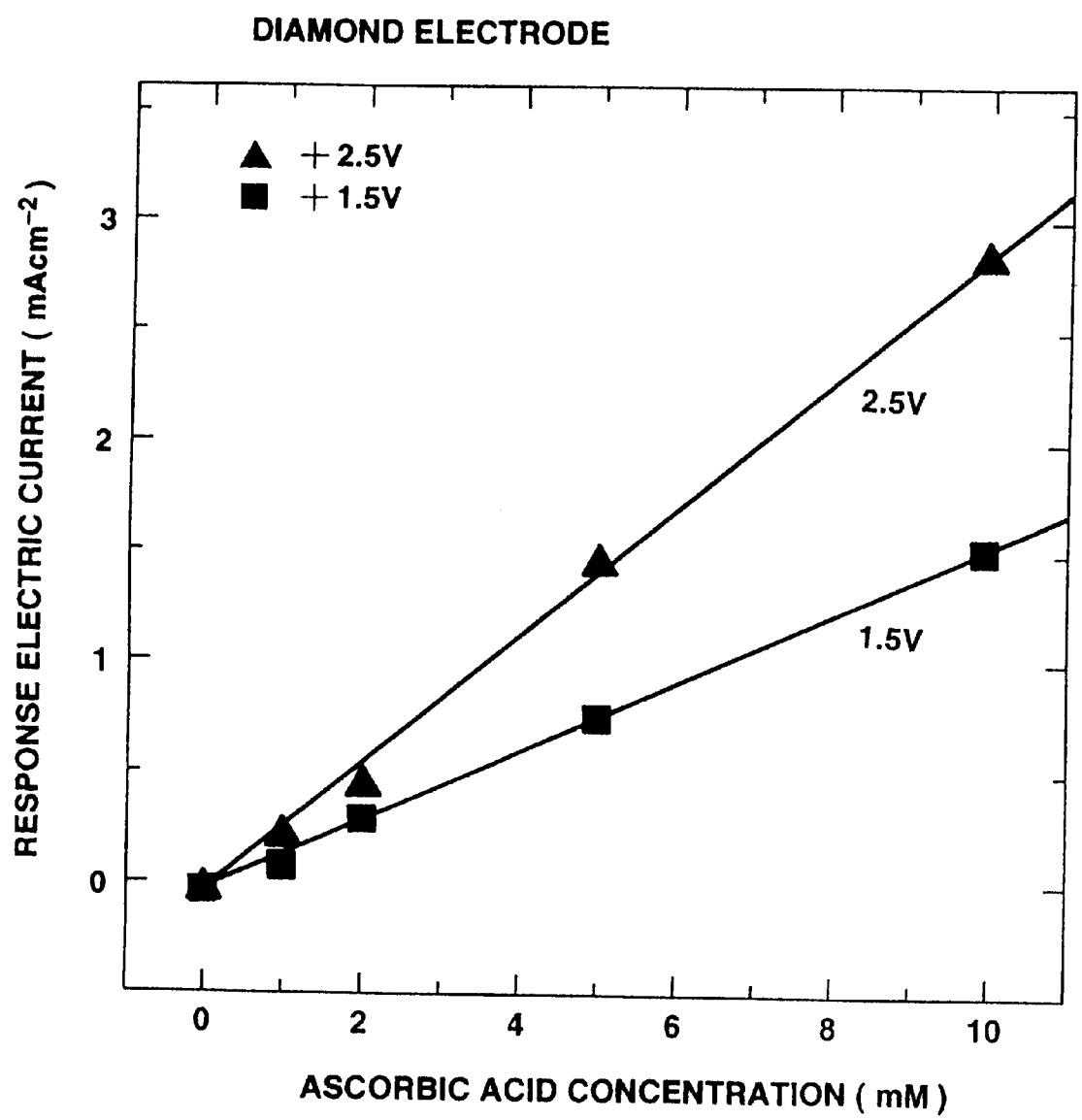
FIG. 29 shows relationship between response electric current on a diamond detection electrode and ascorbic acid concentration when potentials of +1.5V and +2.5V are applied to the electrode.

For example, as described before, the current-potential curves in FIG. 36 were prepared by using two samples containing and not containing 1 mM ascorbic acid in phosphate buffer (pH 7.0) with the diamond detection electrode, which show the facts that ascorbic acid begins oxidation at about +0.8 V on the diamond electrode and that an almost constant oxidation current flows in the potential region of 1–2V. This means that a response electric current varies depending on the concentration of ascorbic acid at a potential of 1–2V, say 1.5V so that a straight line connecting the measured plots ■ showing the proportional relationship between the response electric current and the ascorbic acid concentration (in a range of 1–10 mM) can be obtained as shown in FIG. 29. Further, assuming measurement in coexistence of hydrogen peroxide and glucose, the same relationship was determined at a potential of +2.5 V where hydrogen peroxide and glucose are oxidized, to prepare another straight line connecting the measured plots ▲, which is also shown in FIG. 29.

In the same manner as described above, the relationship between the response electric current and the concentration for various substances such as hydrogen peroxide, ascorbic acid, uric acid and glucose were determined on the platinum electrode and diamond electrode, respectively, which are shown in FIGS. 26–32.

Figure 26:
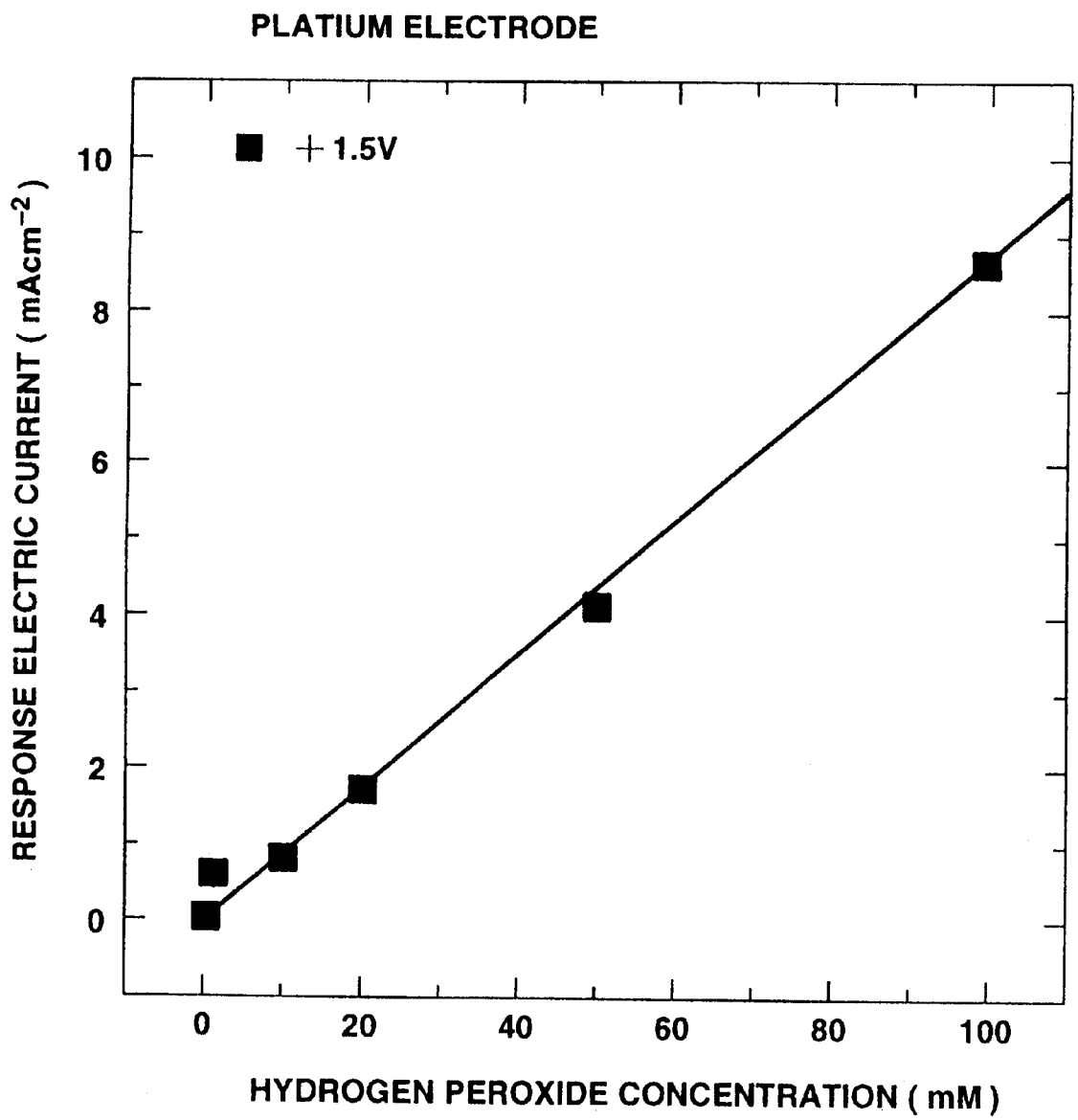
FIG. 26 shows relationship between response electric current on a platinum detection electrode and hydrogen peroxide concentration when a potential of +1.5V is applied to the electrode.

FIG. 26 shows the proportional relationship between the response electric current and the hydrogen peroxide concentration, which is obtained by determining the oxidation current values on a platinum detection electrode at +1.5V in an electrolyte of a phosphate buffer (pH 7.0) containing hydrogen peroxide at various concentrations.

Figure 27:
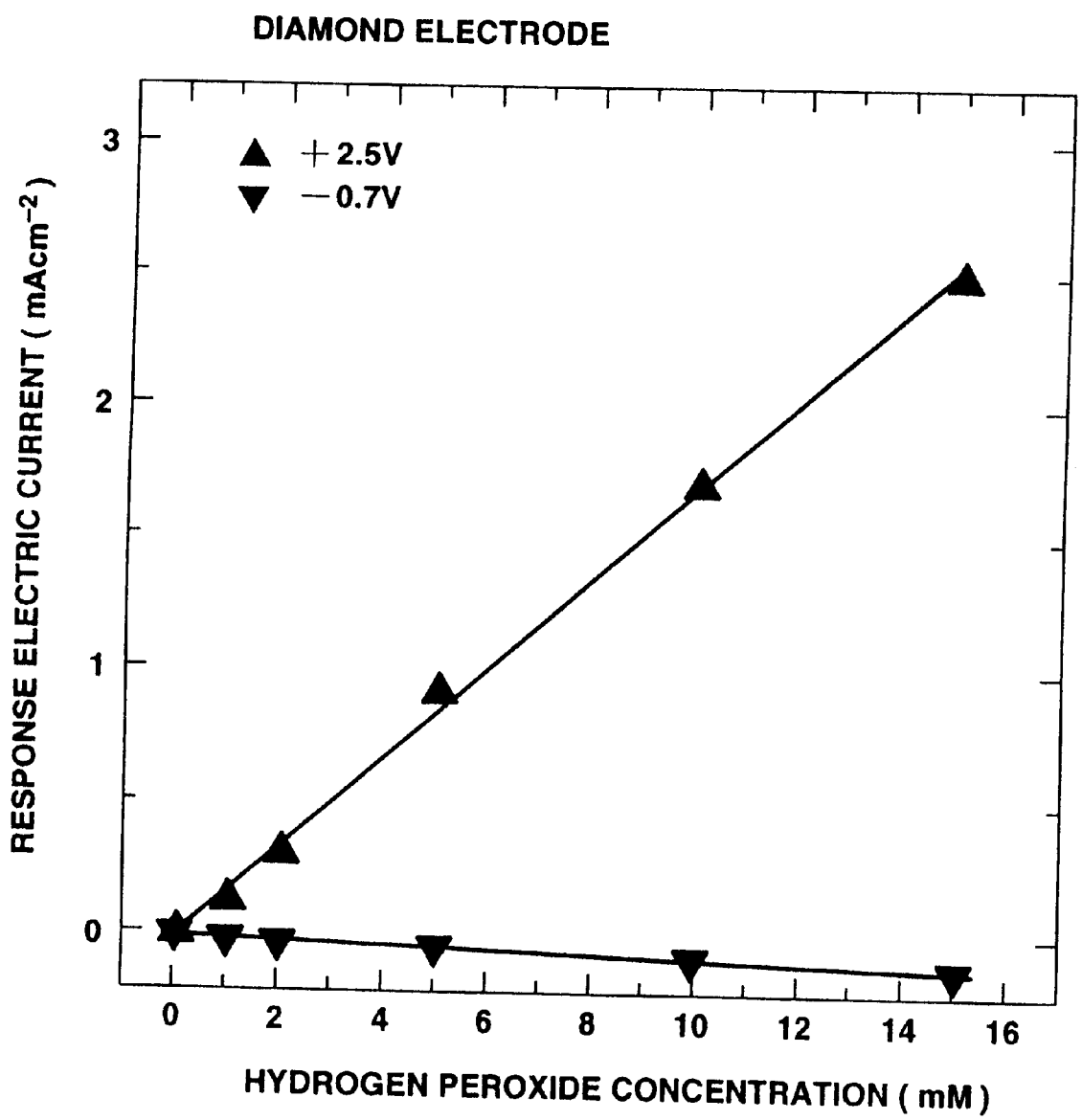
FIG. 27 shows relationship between response electric current on a diamond detection electrode and hydrogen peroxide concentration when potentials of +2.5V and –0.7V are applied to the electrode.

FIG. 27 shows the proportional relationship between the response electric current and the hydrogen peroxide concentration, which is obtained by determining the current values on the same electrode at −0.7V in an electrolyte of a phosphate buffer (pH 7.0) containing hydrogen peroxide at various concentrations.

Figure 28:
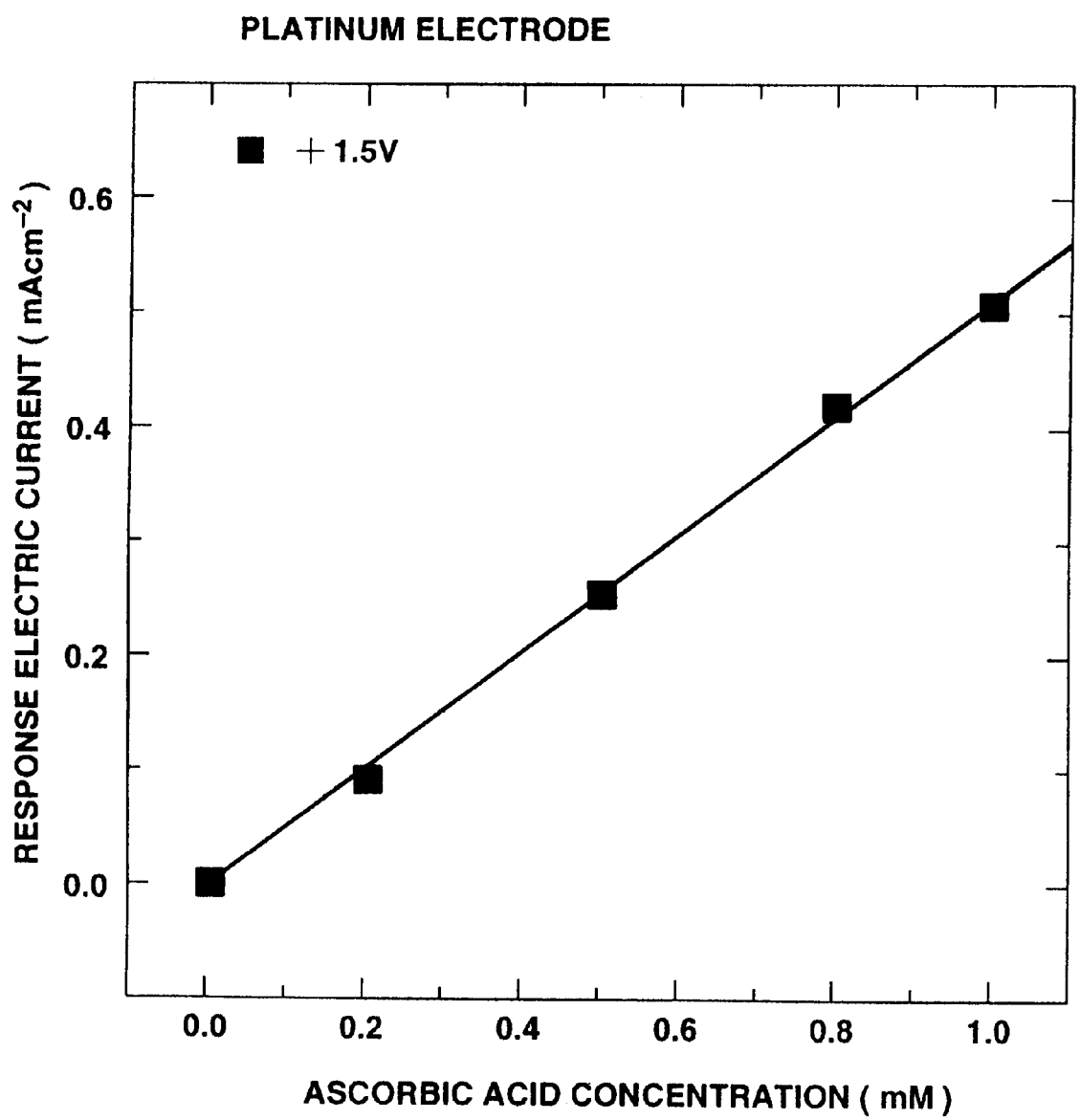
FIG. 28 shows relationship between response electric current on a platinum detection electrode and ascorbic acid concentration when a potential of +1.5V is applied to the electrode.

FIG. 28 shows the proportional relationship between the response electric current and the ascorbic acid concentration, which is obtained by determining the oxidation current values on a platinum detection electrode at +1.5V in an electrolyte of a phosphate buffer (pH 7.0) containing ascorbic acid at various concentrations.

FIG. 29 shows the proportional relationship between the response electric current and the ascorbic acid concentration, which is obtained by determining the oxidation current values on a diamond detection electrode at +1.5V and +2.5V in an electrolyte of a phosphate buffer (pH 7.0) containing ascorbic acid at various concentrations.

Figure 30:
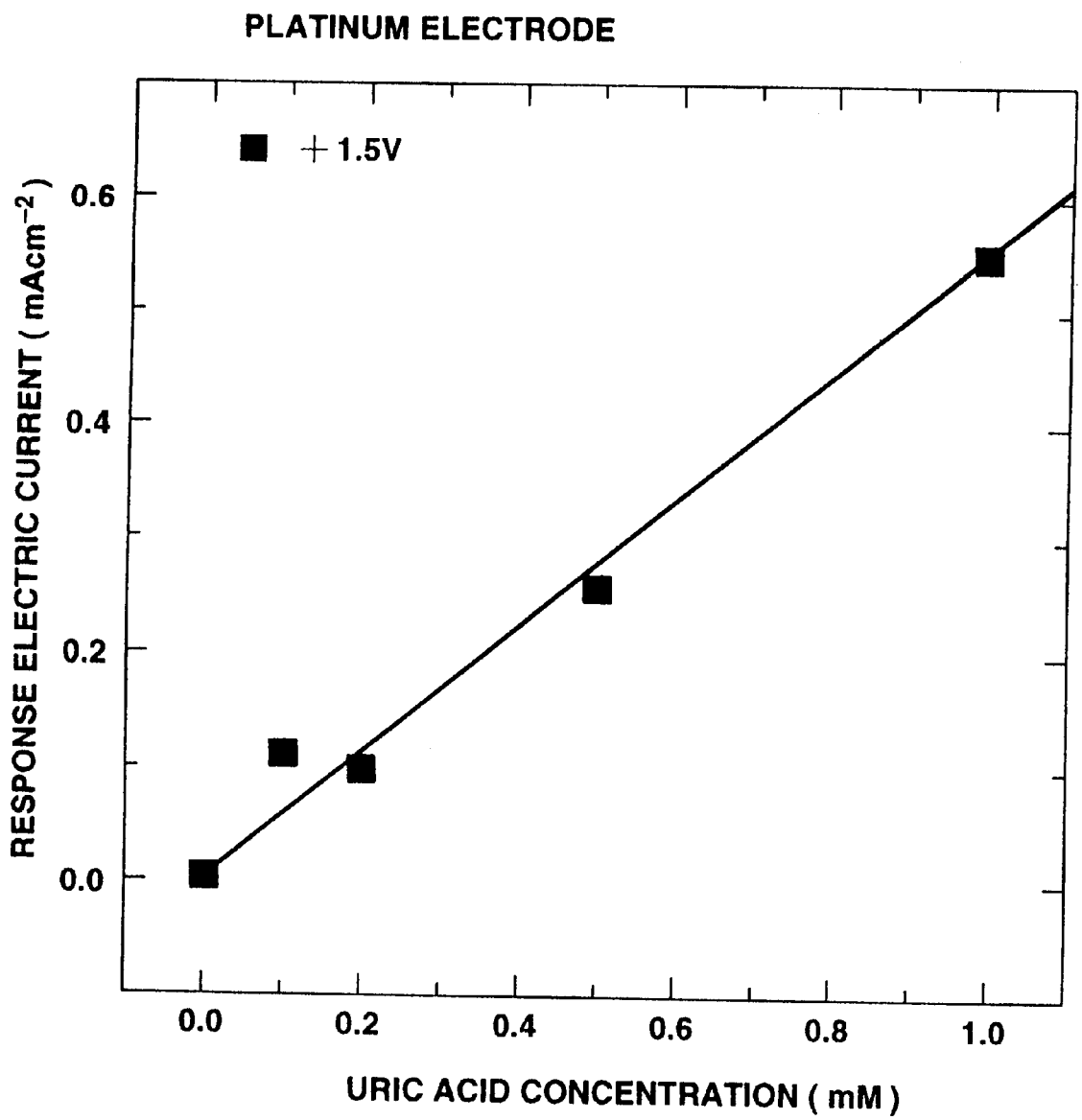
FIG. 30 shows relationship between response electric current on a platinum detection electrode and uric acid concentration when a potential of +1.5V is applied to the electrode.

FIG. 30 shows the proportional relationship between the response electric current and the uric acid concentration, which is obtained by determining the oxidation current values on a platinum detection electrode at +1.5V in an electrolyte of a phosphate buffer (pH 7.0) containing uric acid at various concentrations.

Figure 31:
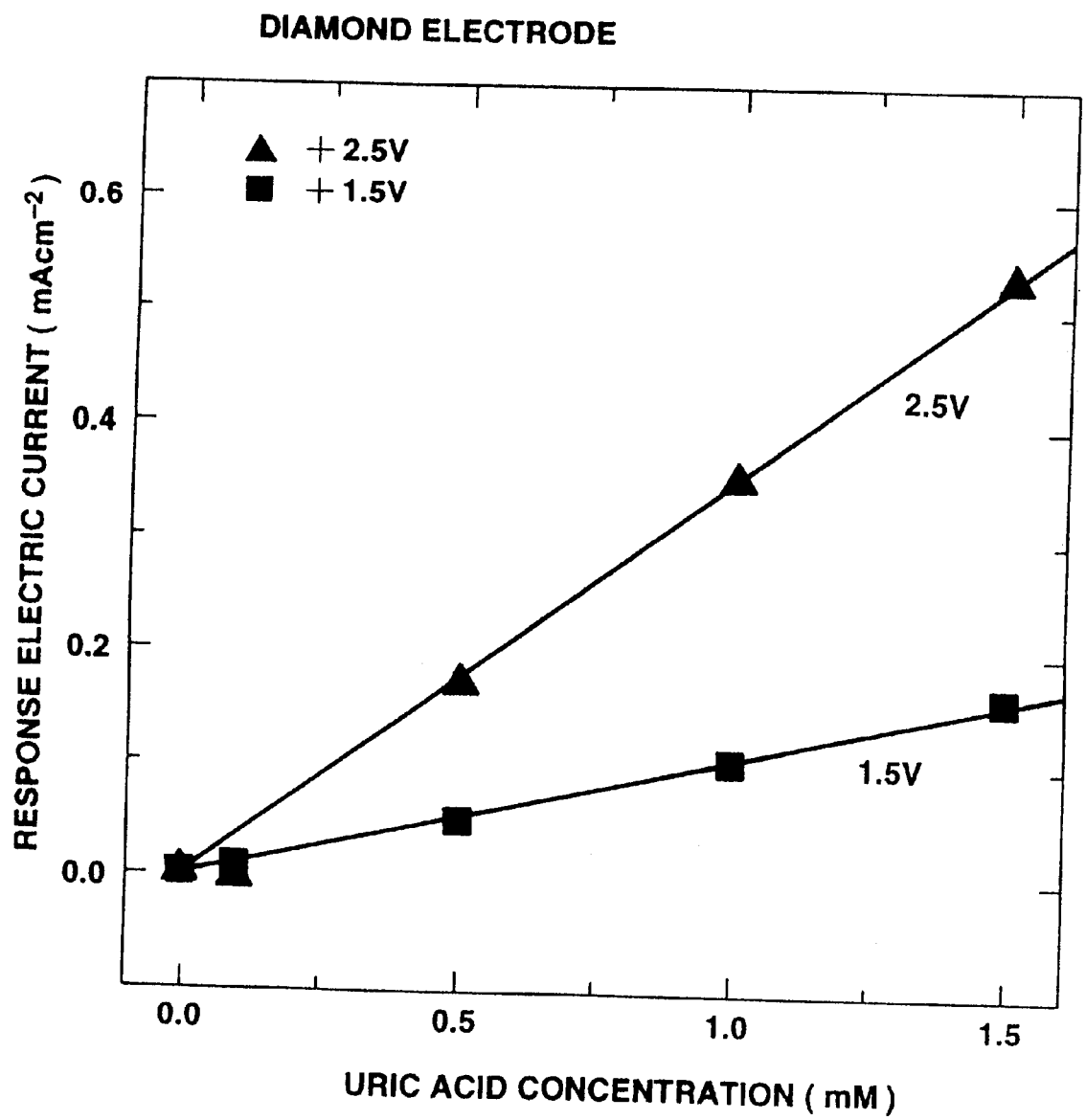
FIG. 31 shows relationship between response electric current on a diamond detection electrode and uric acid concentration when potentials of +1.5V and +2.5V are applied to the electrode.

FIG. 31 shows the proportional relationship between the response electric current and the uric acid concentration, which is obtained by determining the oxidation current values on a diamond detection electrode at +1.5V and +2.5V in an electrolyte of a phosphate buffer (pH 7.0) containing uric acid at various concentrations.

Figure 32:
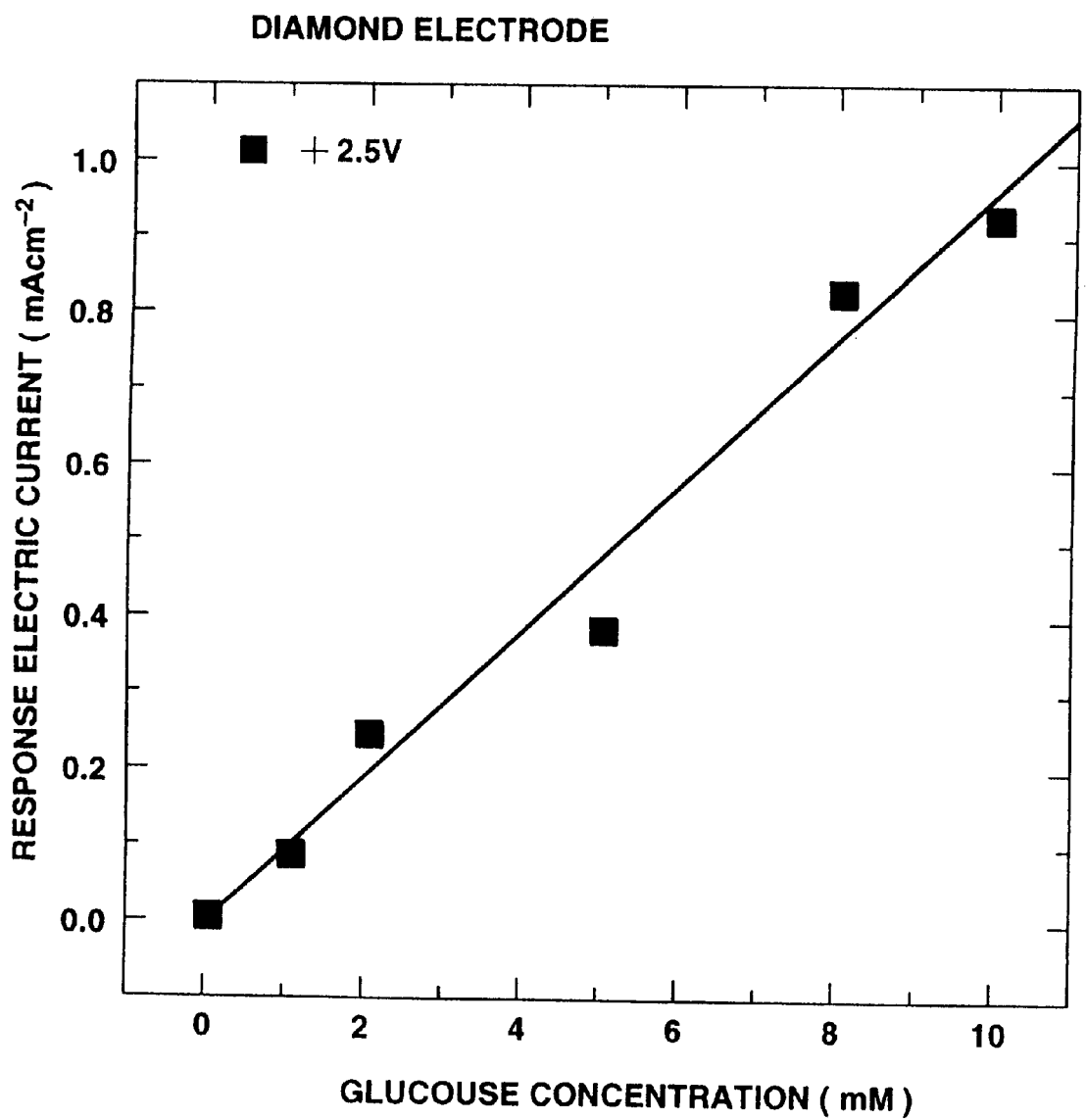
FIG. 32 shows relationship between response electric current on a diamond detection electrode and glucose concentration when a potential of +2.5V is applied to the electrode.

FIG. 32 shows the proportional relationship between the response electric current and the glucose concentration, which is obtained by determining the oxidation current values on a diamond detection electrode at +2.5V in an electrolyte of a phosphate buffer (pH 7.0) containing glucose at various concentrations.

In accordance with the concentration measuring method of the present invention, by applying any desired one or combination of the above-described fundamental principle, patterns I, II and III, it is possible to measure concentration of a single substance such as hydrogen peroxide, ascorbic acid, uric acid, glucose, methanol, enzyme, etc. but also any combination thereof, in reference to their response characteristics, that is the relationship between the electric current density and the electric potential shown by the graphs in FIGS. 33 to 44.

The current-concentration relationship may be determined by using the concentration sensor with a rotating disk electrode. When the concentration sensor with a rotating disk detection electrode is used, a response electric current is measured while the detection electrode is rotated at a constant rate of revolution to obtain the current-concentration relationship for a target substance. Except rotation of the rotating disk electrode, the current-concentration relationship may be obtained in the same manner as in, the case where the concentration sensor has a stationary detection electrode. The rotating detection electrode facilitates diffusion of the target substances onto the surface thereof, thus increasing the diffusion current of the target substances to improve the sensitivity of detection and measurement.

Figure 54:
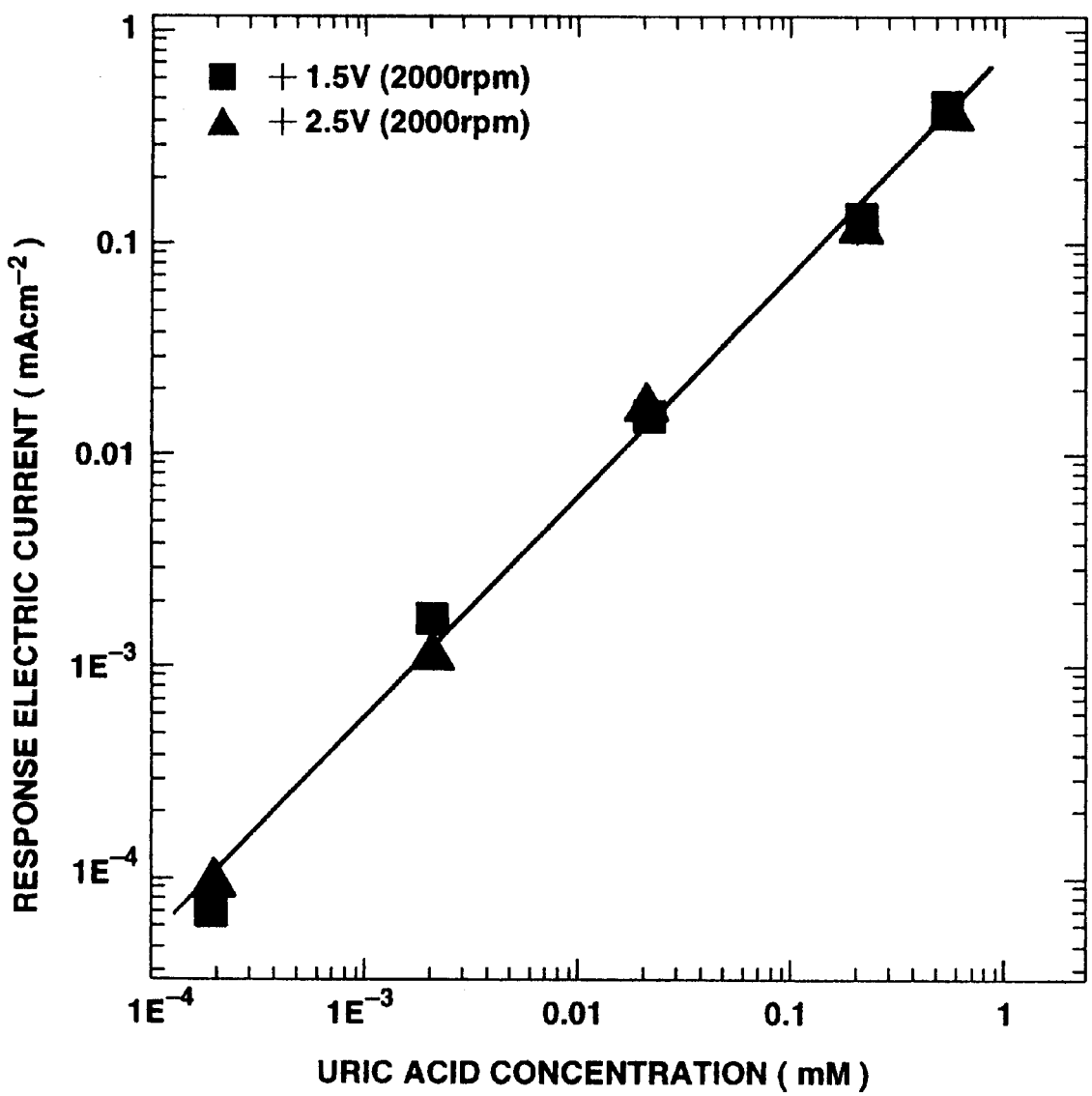
FIG. 54 shows proportional relationship between response electric current and uric acid concentration, which is obtained by determining the oxidation current values on a rotating disk diamond detection electrode at +1.5V and +2.5V in an electrolyte of a phosphate buffer (pH 7.0) containing uric acid at various concentrations.

FIG. 54 shows the proportional relationship between the response electric current and the uric acid concentration, which is obtained by determining the oxidation current values on a rotating disk diamond detection electrode at +1.5V and +2.5V in an electrolyte of a phosphate buffer (pH 7.0) containing uric acid at various concentrations.

Figure 55:
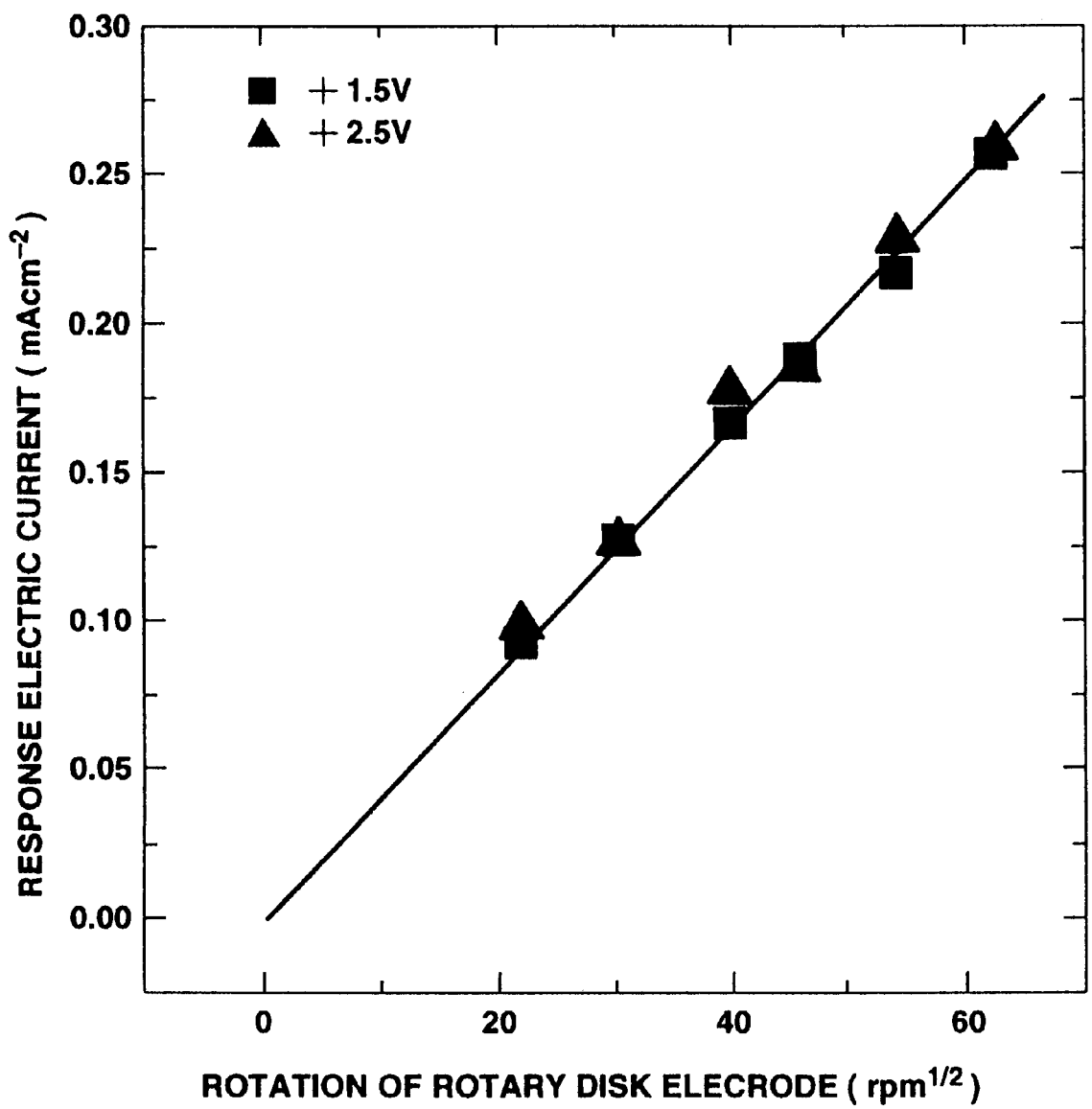
FIG. 55 shows relationship between response density and square root of the number of revolutions of the rotating detection electrode, where the uric acid concentration is 0.2 mM in FIG. 54.

FIG. 55 shows the relationship between the response density and the square root of the number of revolutions of the rotating detection electrode, where the uric acid concentration is 0.2 mM in FIG. 54.

Figure 56:
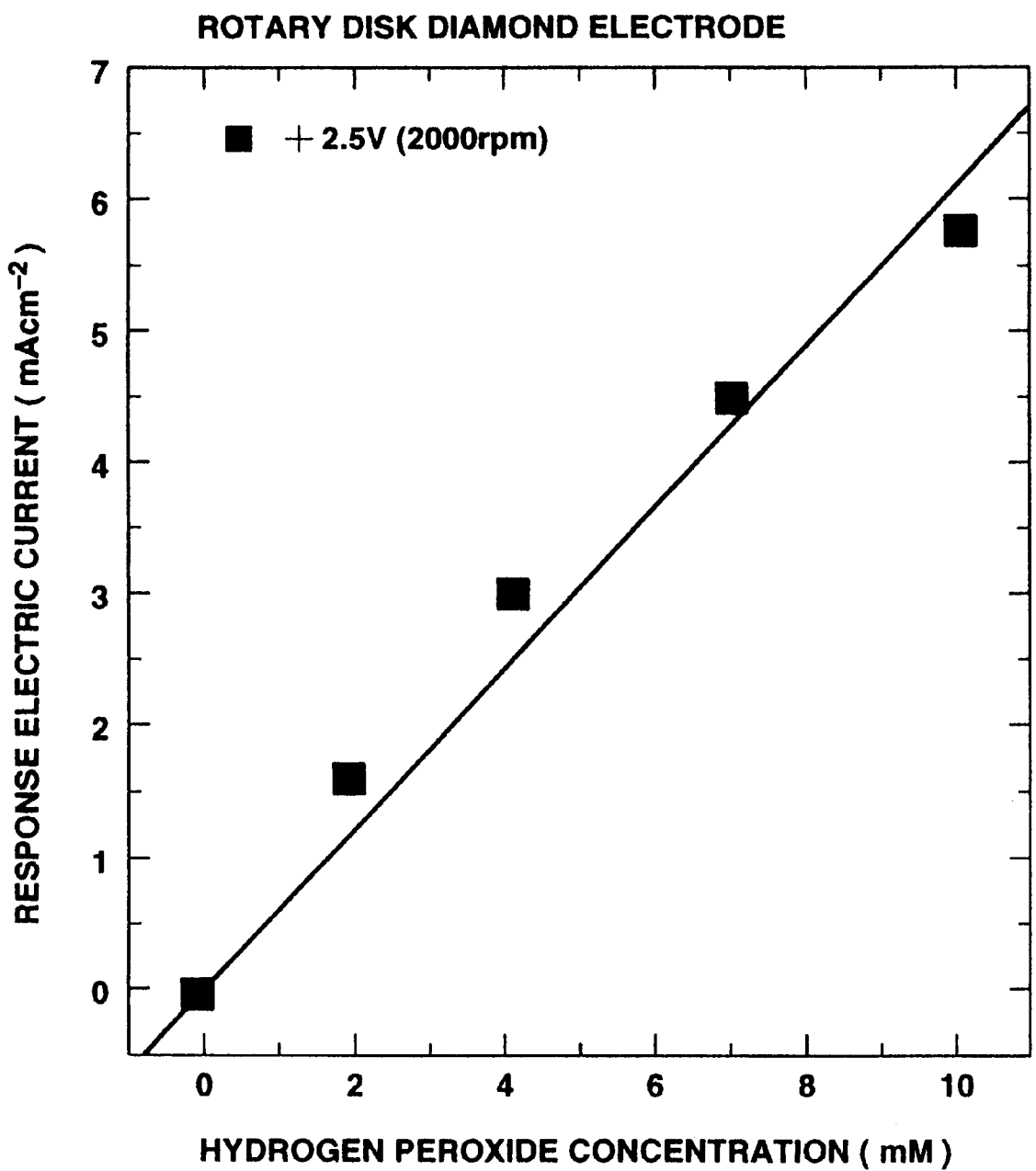
FIG. 56 shows proportional relationship between response electric current and hydrogen peroxide concentration, which is obtained by determining the oxidation current values on a rotating disk diamond detection electrode at +2.5V in an electrolyte of a phosphate buffer (pH 7.0) containing hydrogen peroxide at various concentrations.

FIG. 56 shows the proportional relationship between the response electric current and the hydrogen peroxide concentration, which is obtained by determining the oxidation current values on a rotating disk diamond detection electrode at +2.5V in an electrolyte of a phosphate buffer (pH 7.0) containing hydrogen peroxide at various concentrations.

Figure 57:
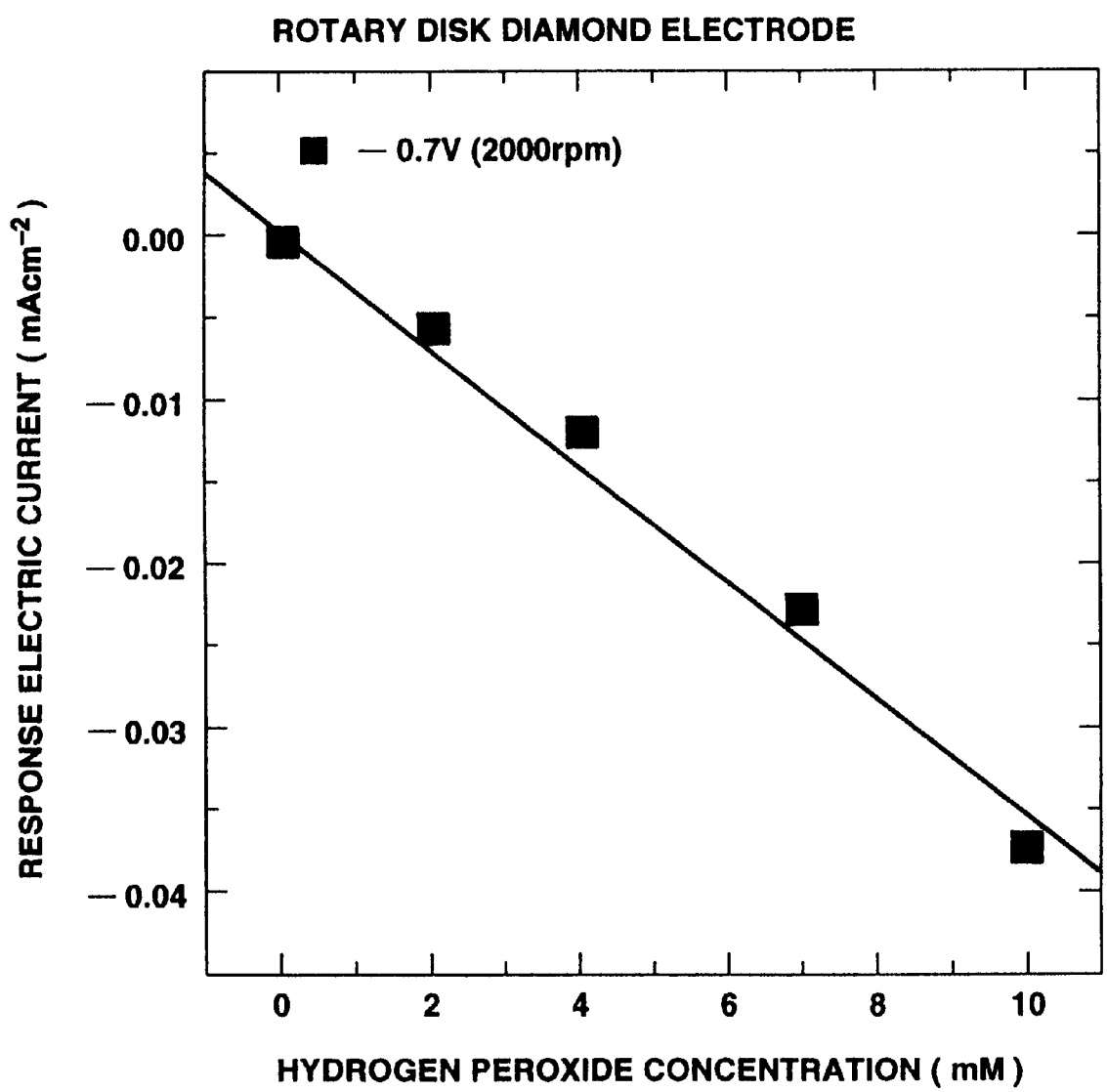
FIG. 57 shows proportional relationship between response electric current and hydrogen peroxide concentration, which is obtained by determining the reduction current values on a rotating disk diamond detection electrode at −0.7V in an electrolyte of a phosphate buffer (pH 7.0) containing hydrogen peroxide at various concentrations.

FIG. 57 shows the proportional relationship between the response electric current and the hydrogen peroxide concentration, which is obtained by determining the reduction current values on a rotating disk diamond detection electrode at −0.7V in an electrolyte of a phosphate buffer (pH 7.0) containing hydrogen peroxide at various concentrations.

Figure 58:
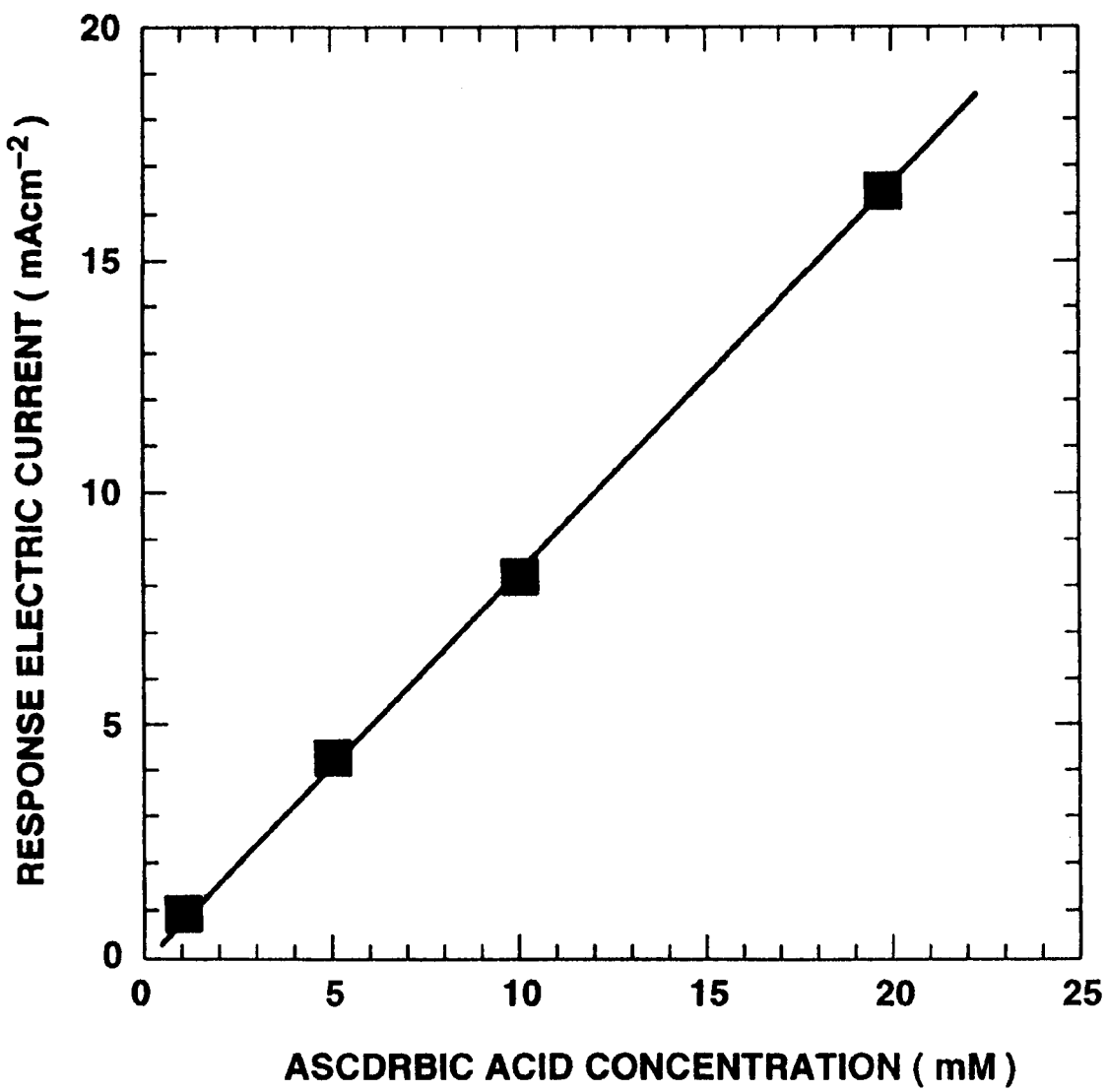
FIG. 58 shows proportional relationship between response electric current and ascorbic acid concentration, which is obtained by determining the oxidation current values on a rotating disk diamond detection electrode at +2.0V in an electrolyte of a phosphate buffer (pH 7.0) containing ascorbic acid at various concentrations.

FIG. 58 shows the proportional relationship between the response electric current and the ascorbic acid concentration, which is obtained by determining the oxidation current values on a rotating disk diamond detection electrode at +2.0V in an electrolyte of a phosphate buffer (pH 7.0) containing ascorbic acid at various concentrations.

Figure 59:
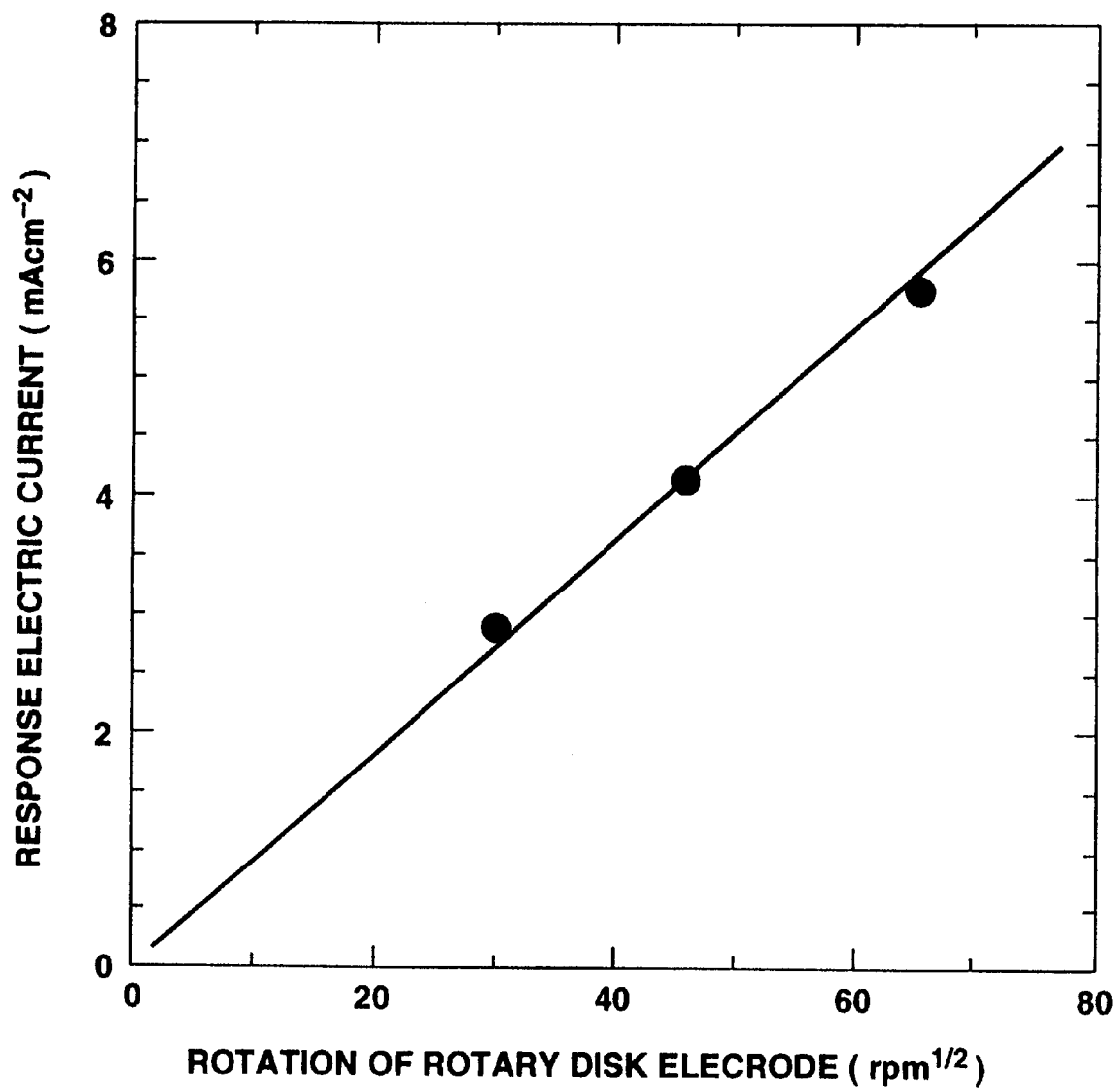
FIG. 59 shows relationship between response density and square root of the number of revolutions of the rotating detection electrode, where the ascorbic acid concentration is 20 mM in FIG. 58.

FIG. 59 shows the relationship between the response density and the square root of the number of revolutions of the rotating detection electrode, where the ascorbic acid concentration is 20 mM in FIG. 58.

EXAMPLES

The concentration of various target substances can be measured by applying one of the measurement patterns I–III in reference to their current-concentration relatioship shown in FIGS. 26–32.

Example 1

In this example a dual-component system containing hydrogen peroxide and ascorbic acid was subjected to measurement in accordance with the measurement pattern I.

As shown in the graphs showing the relationship between the electric current density and the potential in FIGS. 34 and 36, oxidation of hydrogen peroxide and ascorbic acid is initiated on the diamond electrode at +1.8V and +0.7V, respectively. In order to utilize this difference, the diamond electrode was working in a dual-component system to which 15 mM hydrogen peroxide and about 1 mM ascorbic acid had been added, and response electric currents $I_1$ and $I_2$ were observed at +1.5V and +2.5V, respectively. The results were 0.13 mAcm$^{-2}$ and 2.57 mAcm$^{-2}$, respectively.

Because $I_1$ comprises solely the electric current of ascorbic acid, its concentarion could be determined as 0.9 mM from the relationship shown in FIG. 29. FIG. 29 also shows that ascorbic acid of 0.9 mM concentration has a response current value of 0.24 mAcm$^{-2}$ at +2.5V. The oxidation currents $I_2$ is the sum of oxidation currents of ascorbic acid and hydrogen peroxide. Thus, the response current value of hydrogen peroxide at +2.5V was calculated by subtacting the current value of ascorbic acid (0.24 mAcm$^{-2}$) from the sum (2.57 mAcm$^{-2}$) to be determined as 2.33 mAcm$^{-2}$. Then, this electric current value of hydrogen peroxide at +2.5V is plotted on the ▲-▲ line in FIG. 27 showing the relationship between the electric current and hydrogen peroxide concentration at +2.5V, thereby determining its concentration to be 13.7 mM. It is to be noted that the ascorbic acid concentration (0.9 mM) and the hydrogen peroxide concentration (13.7 mM) which were determined in this example will almost agree with their real concentrations (about 1 mM and 15 mM). This confirms that the concentration measurement of the present invention provides high accuracy, sensitivity and reliability.

Example 2

In this example a dual-component system containing hydrogen peroxide and ascorbic acid is subjected to measurement in accordance with the measurement pattern II.

As shown by the graph in FIGS. 33 and 34 showing the relationship between the electric current density and the electric potential with respect to hydrogen peroxide, oxidation of hydrogen peroxide occurs at +0.8V on the platinum electrode and at +1.8V on the diamond electrode, respectively. On the other hand, as shown by the graphs in FIGS. 35 and 36, oxidation of ascorbic acid occurs at substantially the same potential, that is about 0.7V, irrespective of whether the electrode is of platinum or diamond.

In orter to utilize such difference in oxidation characteristics between hydrogen peroxide and ascorbic acid, the diamond electrode and the platinum electrode are made operative in the dual-component system containing hydrogen peroxide and ascorbic acid, and a voltage of +1.5V, for example, is applied to these electrodes to measure the response electric current values $I_{Pt}$ and $I_D$ flowing on the electrodes, respectively. Since $I_D$ comprises solely the electric current of ascorbic acid, the concentration of ascorbic acid can be determined from the previously prepared relationship (■-■ line at +1.5V at a diamond electrode) for ascorbic acid shown in FIG. 29. An electric current value corresponding to the above-determined concentration of ascorbic acid is determined from the relationship (■-■ line at +1.5V at a platinum electrode) for ascorbic acid shown in FIG. 28. The determined electric current value of ascorbic acid is subtracted from the electric current value $I_{Pt}$ that is the sum of the oxidation currents of ascorbic acid and hydrogen peroxide, to obtain an electric current value of hydrogen peroxide at +1.5V at a platinum electrode. Accordingly, the concentration of hydrogen peroxide can be determined by plotting this current value on the ■-■ line in FIG. 26.

Example 3

In this example, a dual-component system containing hydrogen peroxide and ascorbic acid is subjected to measurement in accordance with the measurement pattern III.

As shown in the graph in FIG. 34, reduction of hydrogen peroxide on the diamond electrode occurs at +0.2V or less. On the other hand, as shown in the graph in FIG. 36, reduction of ascorbic acid hardly occurs on the diamond electrode. In order to utilize such difference, the diamond electrode is operated in a dual-component system containing hydrogen peroxide and ascorbic acid, and response electric currents I+ and I−are measured where potentials of +1.5V and −0.7V, for example, are applied to the electrode, respectively. The current I⁺ is an oxidation current of ascorbic acid and the current I− is a reduction current of hydrogen peroxide, whereby their concentrations can be determined from the relational lines shown in FIG. 27 (for hydrogen peroxide) and in FIG. 29 (for ascorbic acid).

Example 4

In this example, a dual-component system containing hydrogen peroxide and uric acid is subjected to measurement in accordance with the measurement pattern I.

As shown in the respective graphs in FIGS. 34 and 38 showing the relationship between the electric current density and the electric potential, oxidation of hydrogen peroxide and uric acid is initiated at +1.8 V and +0.8 V, respectively, on the diamond electrode. In order to utilize this oxidation-initiating potential difference, the diamond electrode is made operative in the dual-component system, and potentials of +1.5V and +2.5V, for example, are applied thereto to observe response electric currents $I_1$ and $I_2$, respectively. The current $I_1$ is an oxidation current of uric acid so that its concentration can be determined from the previously prepared relational line in FIG. 31. An electric current corresponding to the above-determined concentration of uric acid can be known from the relationship in FIG. 31. This current value is subtracted from the sum current $I_2$ to obtain an electric current value of hydrogen peroxide. The concentration of hydrogen peroxide can be determined in the same manner from the relational line in FIG. 27.

Example 5

In this example, a dual-component system containing hydrogen peroxide and uric acid is subjected to measurement in accordance with the measurement pattern II.

As shown in FIGS. 33 and 34, the electric potentials at which oxidation of hydrogen peroxide on the platinum electrode and on the diamond electrode are quite different, that is, +0.8V and +1.8V, respectively. On the other hand, oxidation of uric acid occurs at about 0.8V on either of the platinum electrode and the diamond electrode. Such difference in oxidation characteristics between hydrogen peroxide and uric acid is utilized in this example.

More particularly, the dual-component system of hydrogen peroxide and uric acid is subjected to measurement with the platinum and diamond electrodes to which the potential of +1.5V, for example, is applied, thereby determining electric currents $I_{Pt}$ and $I_D$ are determined at both electrodes, respectively. Since the current value $I_D$ only originates from oxidation of uric acid, its concentration can be determined from the relationship shown in FIG. 31. An electric current corresponding to the above-determined concentration of uric acid on the platinum electrode can be known from the relational line in FIG. 30. This current value is subtracted from the sum current $I_{Pt}$ to obtain an electric current value of hydrogen peroxide at the platinum electrode. The concentration of hydrogen peroxide can be determined in the same manner from the relational line in FIG. 26.

Example 6

In this example, a dual-component system containing hydrogen peroxide and uric acid is subjected to measurement in accordance with the measurement pattern III.

As shown in FIG. 34, reduction of hydrogen peroxide occurs at +0.2 V or less on the diamond electrode. On the other hand, as shown in FIG. 38, reduction of uric acid hardly occurs on the diamond electrode. This example utilizes such difference for concentration measurement. More particularly, the diamond electrode is operative in the dual-component system of hydrogen peroxide and uric acid, and electric currents I⁺ and I⁻ are determined by applying potentials of +1.5V and −0.7V, for example, to the diamond electrode. The current value I⁺ is an electric current resulting from oxidation of uric acid, while I⁻ results from reduction of hydrogen peroxide, so that each concentration can be determined from the relationship in FIG. 31 for uric acid and from the relationship in FIG. 27 for hydrogen peroxide.

Example 7

In this example, a sample only containing glucose is subjected to measurement in accordance with the fundamental measurement principle.

As shown in FIG. 40, oxidation of glucose on the diamond electrode is initiated at about +2.2V. In order to utilize this fact, a sole-component system only containing glucose is subjected to measurement with the diamond electrode to which a potential of +2.5V, for example, is applied. An electric current I at the diamond electrode in this example originates from oxidation of glucose, so that the concentration of glucose can be determined from the relationship shown in FIG. 32 between glucose concentrations and response electric currents.

The measurable concentration range depends on sensitivity of the detector but would cover at least a range of 1 to 10 mM which includes normal blood sugar levels (about 5 to 6 mM). Accordingly, this method is useful to measure blood sugar levels. In addition, this method becomes capable of measuring a lower level of concentration by employing the rotating disk electrode to improve its sensitivity.

As shown in the graph of FIG. 39 showing the relationship between the electric current and the potential in the case of the platinum electrode, there can be seen no considerable flow of the electric current in the oxidation of glucose at the potential of about +1.6V or lower. At +1.6 Vor larger potential, a large amount of electric current flows due to generation of oxygen, which makes it difficult to measure the glucose concentration. As a conclusion, it is difficult or practically impossible to measure the glucose concentration whith the platinum electrode.

Example 8

In this Example 8, a dual-component system containing glucose and ascorbic acid is subjected to measurement in accordance with the measurement pattern I.

As shown in the graphs of FIGS. 40 and 36, oxidation of glucose and ascorbic acid on the diamond electrode is initiated at +2.2V and +0.7V, respectively. In order to utilize such difference, the diamond electrode is made operative in the dual component containing glucose and ascorbic acid, and response electric currents $I_1$ and $I_2$ are determined by applying the potentials of +1.5V and +2.5V, for example. Since the current value $I_1$ is equal to the oxidation electric current of ascorbic acid, the concentration of ascorbic acid can be determined from the previously prepared current-concentration relationship shown in FIG. 29.

An electric current corresponding to the above-determined concentration of ascorbic acid can be known from the relationship in FIG. 29. This current value is subtracted from the sum current $I_2$ to obtain an electric current value of glucose, which is plotted to the relational line in FIG. 32 to obtain its concentration.

The measurable concentration range depends on sensitivity of the detector, but would sufficiently cover a 1–10 mM range. Accordingly, this method is effectively applicable to measurement of normal blood sugar levels of the order of 5–6 mM. This method becomes capable of measuring a lower level of concentration by employing the rotating disk electrode to improve its sensitivity.

Example 9

In this example, a dual-component system containing glucose and uric acid is subjected to measurement in accordance with the measurement pattern I.

As shown in the graphs of FIGS. 40 and 38, oxidation of glucose and uric acid on the diamond electrode is initiated at +2.2V and +0.8V, respectively. In order to utilize such difference, the diamond electrode is made operative in the dual component containing glucose and uric acid, and response electric currents $I_1$ and $I_2$ are determined by applying the potentials of +1.5V and +2.5V, for example. Since the current value $I_1$ is equal to the oxidation electric current of uric acid, the concentration of uric acid can be determined from the previously prepared current-concentration relationship shown in FIG. 31.

An electric current corresponding to the above-determined concentration of uric acid can be known from the relationship in FIG. 31. This current value is subtracted from the sum current $I_2$ to obtaine an electric current value of glucose, which is plotted to the relational line in FIG. 32 to obtain its concentration.

The measurable concentration range depends on sensitivity of the detector, but would sufficiently cover a 1–10 mM range. Accordingly, this method is effectively applicable to measurement of normal blood sugar levels of the order of 5–6 mM. Applicability of this method may be broadened by employing the rotating disk electrode to improve its sensitivity.

Example 10

In this example, a tri-component system containing glucose, hydrogen peroxide and ascorbic acid is subjected to measurement in accordance with combination of the measurement patterns I and III.

As shown in the graphs of FIGS. 40, 34 and 36, oxidation of glucose, hydrogen peroxide and ascorbic acid on the diamond electrode is initiated at +2.2V, +1.8V and +0.7V, respectively. On the other hand, reduction of hydrogen occurs at +0.2V or less, but ascorbic acid and glucose will hardly be reduced at any potential.

In order to utilize such differences in oxidation- and reduction-initiating potentials of the respective components, the diamond electrode is made operative in the tri-component system containing glucose, hydrogen peroxide and ascorbic acid, and the response electric currents $I_1$, $I_2$ and $I-$ are determined by applying the potentials of +1.5V, +2.5V and −0.7V, for example, respectively. The current value $I_1$ comprises soley an oxidation electric current of ascorbic acid and, therefore, the concentration of ascorbic acid can be determined from the previously prepared current-concentration relationship shown in FIG. 29. The current value $I-$ is simply a reduction electric current of hydrogen peroxide and, therefore, the concentration of hydrogen peroxide can be determined from the previously prepared current-concentration relationship shown in FIG. 27. Once the concetrations of ascorbic acid and hydrogen peroxide are known in the above-described manner, their oxidation currents at 2.5V can be determined from the relationship in FIGS. 29 and 27. Then, these current values is subtracted from the current value $I_2$ representing the total sum of oxidation currents of glucose, hydrogen peroxide and ascorbic acid at 2.5V, to obtain a current value originating from oxidation of glucose at 2.5V, which is plotted to the current-concentration relationship shown in FIG. 32 to determine its concentration.

Example 11

In this example, a tri-component system containing glucose, hydrogen peroxide and uric acid is subjected to measurement in accordance with combination of the measurement patterns I and III.

As shown in the graphs of FIGS. 40, 34 and 38, oxidation of glucose, hydrogen peroxide and uric acid on the diamond electrode is initiated at +2.2V, +1.8V and +0.8V, respectively. On the other hand, reduction of hydrogen occurs at +0.2V or less, but uric acid and glucose will hardly be reduced at any potential.

In order to utilize such differences in oxidation- and reduction-initiating potentials of the respective components, the diamond electrode is made operative in the tri-component system containing glucose, hydrogen peroxide and uric acid, and the response electric currents $I_1$, $I_2$ and $I-$ are determined by applying the potentials of +1.5V, +2.5V and −0.7V, for example, respectively. The current value $I_1$ comprises soley an oxidation electric current of uric acid and, therefore, the concentration of uric acid can be determined from the previously prepared current-concentration relationship shown in FIG. 31. The current value $I-$ is simply a reduction electric current of hydrogen peroxide and, therefore, the concentration of hydrogen peroxide can be determined from the previously prepared current-concentration relationship shown in FIG. 27. Once the concetrations of uric acid and hydrogen peroxide are known in the above-described manner, their oxidation currents at 2.5V can be determined from the relationship in FIGS. 31 and 27. Then, these current values is subtracted from the current value $I_2$ representing the total sum of oxidation currents of glucose, hydrogen peroxide and uric acid at 2.5V, to obtain a current value originating from oxidation of glucose at 2.5V, which is plotted to the current-concentration relationship shown in FIG. 32 to determine its concentration.

Example 12

Figure 45:
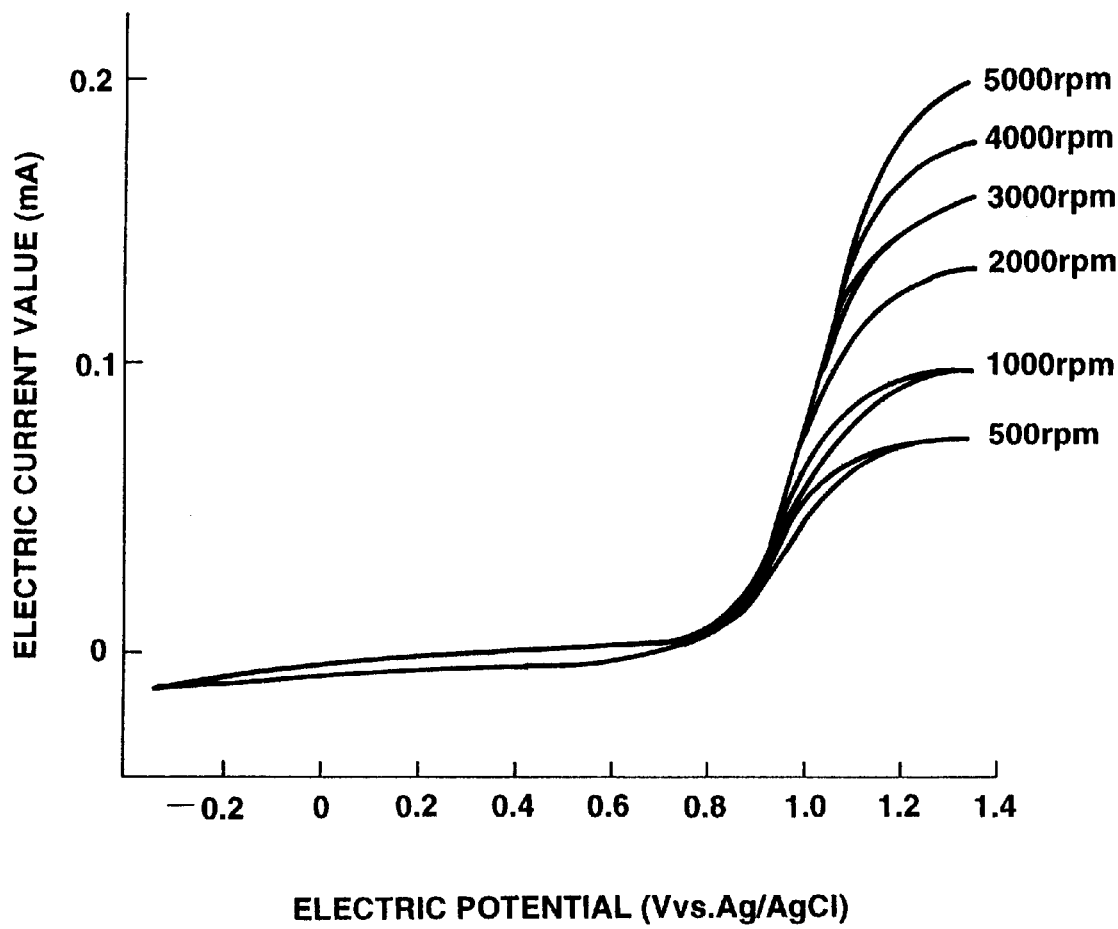
FIG. 45 is a current-potential graph showing relationship between an electric current on a rotating disk diamond detection electrode and potential when an electrolyte containing dopamine is subjected to measurement.

In this example, a 0.1M $HClO_4$ electrolyte containing 1 mM dopamine, which is known as one of neurotransmitters, is subjected to measurement in accordance with the fundamental measurement principle. The concentration sensor used in this example is of a type shown in FIG. 19 with a rotational disk electrode of conductive diamond, which is rotated at a high speed of 500 to 5,000 rpm to monitor the electrochemical reaction on the detection electrode at a steep rate of 50 mV/sec. As a result, the relationship between the electric current value and the potential is obtained as shown in FIG. 45. The potential is a value relative to a silver chloride electrode.

As shown in FIG. 45, it has been revealed that the oxidation current increases in proportion to the square root of the number of revolutions of the detection electrode. This implies that, the response electric current of the target substance can be increased with the speed of rotation of the rotating disk detection electrode.

Figure 46:
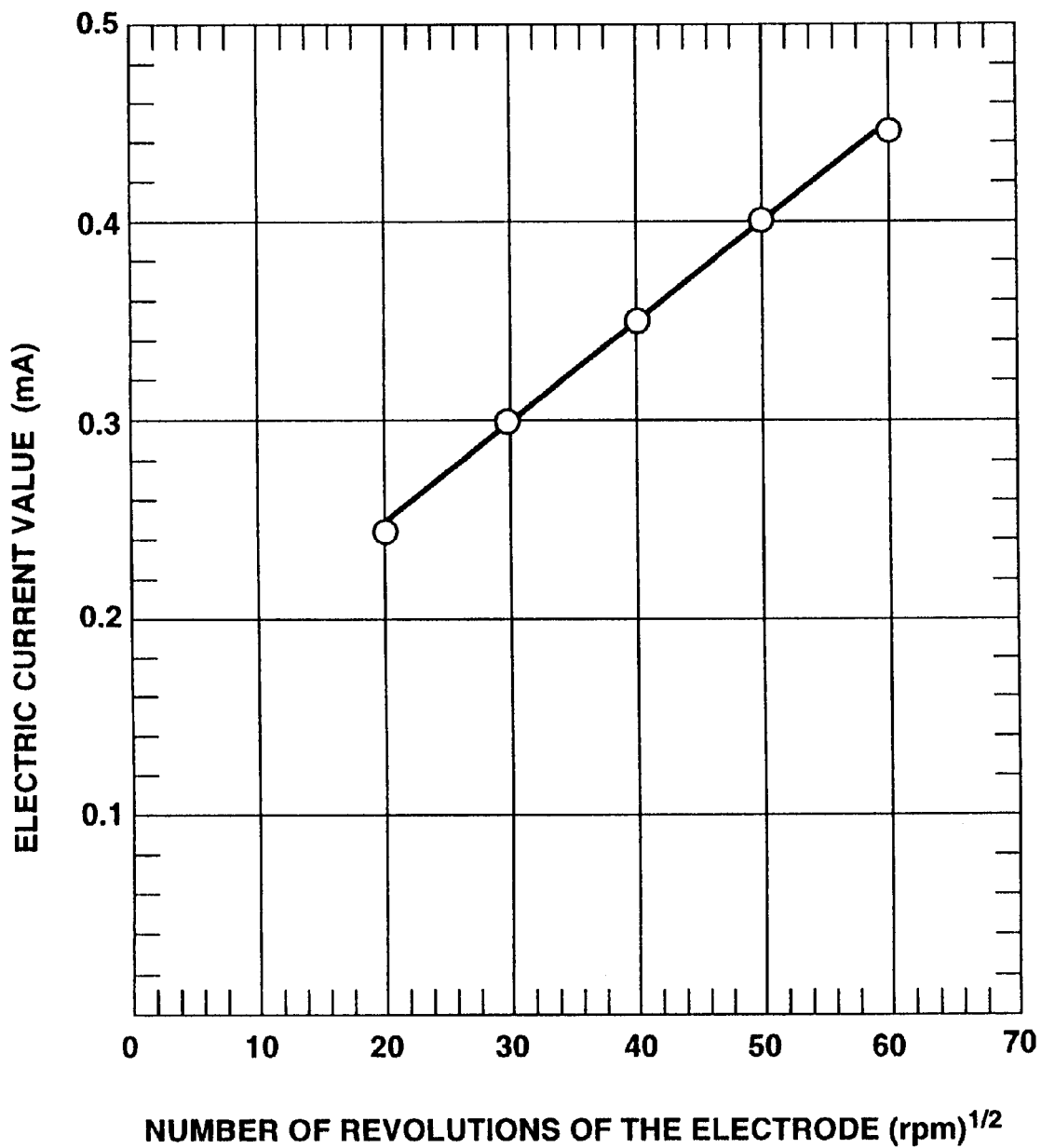
FIG. 46 shows relationship between the squre root of the number of revolutions of the rotating disk diamond detection electrode and the oxidation current, which is obtained from the results shown in FIG. 45.

From the results shown in FIG. 45 is prepared the proportional relationship between the square root of the number of revolutions of the detection electrode and the oxidation current, as shown in FIG. 46. The residual electric current is constant independent of the number of revolutions. Thus, the sensitivity in detection of dopamine can be improved by increasing the number of revolutions.

Example 13

In this example, a system only containing uric acid is subjected to measurement in accordance with the fundamental measurement principle, with the rotating disk diamond electrode.

As noted in Example 13 and as shown in FIG. 47, with the rotational disk diamond detection electrode, the response electric current is amplified to improve sensitivity of detection of uric acid, as well as other target components. More particularly, where the rotating disk diamond detection electrode is rotated at 2000 rpm, as shown in FIG. 54, the responsive diffusion electric current of uric acid oxidation increases linearly from $10^{-4}$ mM to 0.4 mM, which is a solubility limit of uric acid in water at room temperature, as its concentration increases.

In order to utilize this fact, the rotating disk diamond electrode is made operative in the system of uric acid, and the response electric current I is determined by applying a potential of +1.5 V, for example. The current value I is equal to an electric current originating from oxidation of uric acid, so that its concentration can be determined from the current-concentration relationship sown in FIG. 54. This example is particularly simple because of the proportional relationship between the response electric current and the uric acid concentration. The concentration of uric acid can be easily determined by multiplying the response electric current I by a proportional constant. In addition, if the applied potential is in the range of +1.5V to +2.5V, the substantially same relational line showing the current-concentration relationship can be applied, as shown in FIG. 54, so that the proportional constant does not depend on the potential as far as it ranges from +1.5V to +2.5V.

Example 14

In this example, a dual-component system containing hydrogen peroxide and uric acid is subjected to measurement with the rotating disk diamond detection electrode in accordance with the measurement pattern I.

The response electric currents of uric acid and hydrogen peroxide are respectively shown in FIGS. 47 and 48, and the sum of which is shown in FIG. 49. FIG. 49 shows the electric current of 0.4 mA at +1.5V. At this potential, hydrogen peroxide does not provide the response electric current (see FIG. 48), so that this current value of 0.4 mA results only from oxidation of uric acid. From the current-concentration relationship shown in FIG. 54, it is understood that the uric acid concentration is 0.4 mM. FIG. 54 also shows that uric acid has the substantially same current-concentration relationship at different potentials of +1.5V and 2.5V so that the oxidation electric current (I₁) of uric acid should be 0.4 mM. The current value I=2.8 mA at +2.5V is the sume of the oxidation electric current of uric acid (I₁) and that of hydrogen peroxide (I₂). Accordingly, the electric current I₂ resulting from oxidation of hyrogen peroxide at +2.5V should be determined by the equation of (I−I₁), that is 2.4 mA. This is plotted to the proportional current-concentration relationship of FIG. 56 to determine the concentration of hydrogen peroxide to be 4 mM.

Example 15

In this example, a dual-component system containing hydrogen peroxide and uric acid is subjected to measurement with the rotating disk diamond detection electrode in accordance with the measurement pattern I.

The response electric currents of uric acid and hydrogen peroxide are respectively shown in FIGS. 47 and 48, the sum of which is shown in FIG. 49. FIG. 49 shows the electric current of 0.4 mA at +1.5V. At this potential, hydrogen peroxide does not provide an oxidation electric current (see FIG. 48), so that this current value of 0.4 mA results only from oxidation of uric acid. From the current-concentration relationship shown in FIG. 54, it is understood that the uric acid concentration is 0.4 mM.

On the contrary, at −0.7V, uric acid does not provide a reduction electric current (see FIG. 48), so that the current value thereat of +0.015 mA results only from reduction of hydrogen peroxide, which is plotted to the current-concentration relationship shown in FIG. 57 to determine its concentration to be 4 mM.

Example 16

This example relates to measurement according to the fundamental measurement principle applied to a sample containing a bovine serum and uric acid.

The sum of the response electric currents of uric acid (see FIG. 47) and various components in a bovine serum is shown in FIG. 50. The difference (I₂−I₁) between the response electric current I₁ at +2.0V of the sample containing 1.5 vol. % bovine serum and the response electric current I₂ of the sample containing 1.5 vol. % bovine serum and uric acid will result from the uric acid concentration of the latter sample. FIG. 50 shows that the difference (I₂−I₁) is 0.07 mA. Since the uric acid concentration is proportional to the response electric current as shown in FIG. 54, it is understood that the current difference of 0.07 mA corresponds to the concentration difference of 0.08 mM. Thus, the uric acid concentration of the latter sample is determined to be 0.08 mM.

Example 17

In this example, a sample containing ascorbic acid is subjected to measurement with the rotating disk diamond detection electrode in accordance with the fundamental measurement principle.

As shown in FIG. 59, use of a rotational disk diamond electrode increases the response electric current and improves detection sensitivity. Further, as shown in FIG. 58, the relationship between the response electric current and ascorbic acid concentration at the same number of revolutions of the rotating disk electrode is proportional, so that determination of the concentration of ascorbic acid is easy. This is utilized in this example. More particularly, the rotating disk diamond electrode is made operative in this sample, and the response electric current I is determined by applying the potential of +2.0V, for example. The current value I results only from oxidation of ascorbic acid, so that the concentration of ascorbic acid can be determined from the current-concentration relationship shown in FIG. 58. In this example, the relationship between the response electric current and ascorbic acid concentration is proportional. Thus, the ascorbic acid concentration can be obtained simply by multiplying the response electric current I by a proportional constant.

Example 18

In this example, a sample containing glucose is subjected to measurement in accordance with the fundamental measurement principle.

More particularly, the conductive diamond detection electrode is immersed in an electrolyte comprising a glucose-containing neutral phosphate buffer solution to monitor the response electric current resulting from oxidation of glucose as shown in FIG. 52. The response electric current resulting from oxidation of glucose become greater where the electrolyte is replaced by a glucose-containing acidic sulfuric acid solution, as shown in FIG. 53 for comparison with FIG. 52. For example, the response electric current of 5 mM glucose at +3.0V in the neutral sample is +0.7 mA/cm$^2$ (FIG. 52), while the response electric current of 5 mM glucose at +3.0 V in the acidic sample is +18 mA/cm$^2$ (FIG. 53) which is 25.7 times higher than that in the former case. Accordingly, even when a sample to be measured for its glucose concentration is neutral, it may be diluted at a dilution ratio of 1/25.7 or less with acidic acid such as sulfuric acid such that the electrolyte becomes acidic, and then subjected to measurement with the diamond detection electrode. In such a manner, the response electric current can be amplified to improve the sensitivity for detection in measurement of concentration of glucose.

What is claimed is:

1. A method of measuring a concentration of a target substance in a sample electrolyte containing plural substances responsive to applied potentials, comprising providing a concentration sensor with a detection electrode of conductive diamond;

directly contacting said sample electrolyte with said detection electrode of conductive diamond;

applying to said detection electrode a specific potential selected to generate a response electric current proportional to the concentration of said target substance by reaction of said target substance on said detection electrode;

said specific potential further selected so that the response electric current does not vary with varying concentration of the plural substances other than said target substance; and determining a concentration of said target substance with reference to a predetermined relationship between the response electric current and a concentration of said target substance at said specific potential.

2. A method of measuring concentrations of plural target substances in a sample electrolyte, comprising:

providing a concentration sensor with a detection electrode of conductive diamond;

directly contacting said sample electrolyte with said detection electrode of conductive diamond;

applying to said detection electrode at least two different specific potentials to thereby generate respective response electric currents proportional to concentrations of one or more of said plural target substances by reaction of said target substances on said detection electrode at said different potentials;

at least one of said different specific potentials selected so that one of said plural target substances does not contribute to the corresponding response electric current; and determining concentrations of said target substance with reference to predetermined relationships between the response electric currents and concentrations of the plural target substances.

3. A method according to claim 2 wherein at a first potential of said different specific potentials only a first of said plural target substances provides its own response electric current proportional to concentration of said first target substance, and at a second potential different from said first potential of said different specific potentials only a second of said plural target substances provides its own response electric current proportional to concentration of said second target substance.

4. A method according to claim 2 wherein a first and a second of said plural target substances provide a first response electric current proportional to concentrations of said first and second target substances at a first specific potential of said different specific potentials, and wherein only one of the first and second target substances provides a second response electric current proportional only to concentration of said one of the first and second target substances at a second specific potential of said different specific potentials.

5. A method according to claim 2 wherein at a predetermined positive potential only a first of said plural target substances provides its own response electric current proportional to oxidation thereof, whereas at a predetermined negative potential only a second of said plural target substances provides its own response electric current proportional to reduction thereof.

6. A method according to claim 2 wherein, at a predetermined positive potential, first and second target substances of said plural target substances provide a first response electric current proportional to oxidation of said first and second target substances, and at a predetermined negative potential only one of said first and second target substances provides a second response electric current proportional to reduction of said one of said first and second target substances.

7. A method according to claim 2 wherein, at a predetermined negative potential, first and second target substances of said plural target substances provide a first response electric current proportional to oxidation of said first and second target substances, and at a predetermined positive potential only one of said first and second target substances provides a second response electric current proportional to reduction of said one of said first and second target substances.

8. A method of measuring concentrations of plural target substances in a sample electrolite, comprising:

providing a concentration sensor with a first detection electrode of a conductive diamond and a second detection electrode of a material other than conductive diamond;

directly contacting said sample electrolite with said first and second detection electrodes;

applying to said first and second detection electrodes respective potentials to thereby generate respective first and second response electric currents by reactions of first and second of said plural target substances on said first and second detection electrodes;

at least one of said first and second potentials being selected to produce its corresponding electric current which does not vary with varying concentration of one of said plural target substances; and determining concentrations of said first and second target substances with reference to predetermined relationships between electric current and concentration for said first and second target substances.

9. A method according to claim 8 wherein oxidation/reduction characteristics of said plural target substances are substantially the same on said second detection electrode but are different on said first detection electrode.

10. A method according to claim 9 wherein said plural target substances initiate oxidation/reduction at different potentials on said first detection electrode.

11. A method according to claim 8 wherein a first of said plural target substances provides its own response electric currents at different potentials on said first and second detection electrodes, respectively, and a second one of said plural target substances provides its own response electric currents at substantially the same potential on said first and second detection electrodes.

* * * * *